US011479773B2

(12) United States Patent
Obika et al.

(10) Patent No.: US 11,479,773 B2
(45) Date of Patent: Oct. 25, 2022

(54) ANTISENSE NUCLEIC ACID FOR INHIBITING BIOSYNTHESIS OF CHONDROITIN SULFATE

(71) Applicants: Aichi Medical University, Nagakute (JP); National Institutes of Biomedical Innovation, Health and Nutrition, Ibaraki (JP)

(72) Inventors: Satoshi Obika, Osaka (JP); Yuya Kasahara, Osaka (JP); Kosei Takeuchi, Aichi (JP)

(73) Assignees: Aichi Medical University, Aichi (JP); National Institutes of Biomedical Innovation, Health and Nutrition, Osaka (JP)

(*) Notice: Subject to any disclaimer, the term of this patent is extended or adjusted under 35 U.S.C. 154(b) by 179 days.

(21) Appl. No.: 16/498,102

(22) PCT Filed: Feb. 20, 2018

(86) PCT No.: PCT/JP2018/005909
§ 371 (c)(1),
(2) Date: Sep. 26, 2019

(87) PCT Pub. No.: WO2018/180005
PCT Pub. Date: Oct. 4, 2018

(65) Prior Publication Data

US 2021/0102214 A1 Apr. 8, 2021

(30) Foreign Application Priority Data

Mar. 31, 2017 (JP) ............................ JP2017-072315

(51) Int. Cl.

| | |
|---|---|
| ***C12N 15/113*** | (2010.01) |
| ***A61P 25/00*** | (2006.01) |
| ***A61K 31/7115*** | (2006.01) |

(52) U.S. Cl.
CPC ...... *C12N 15/1137* (2013.01); *A61K 31/7115* (2013.01); *A61P 25/00* (2018.01); *C12Y 204/01174* (2013.01)

(58) Field of Classification Search
CPC ............ C12N 15/1137; A61K 31/7115; C12Y 204/01174
See application file for complete search history.

(56) References Cited

U.S. PATENT DOCUMENTS

2015/0141320 A1* 5/2015 Krieg .................. C12N 15/113 514/1.1
2015/0152410 A1* 6/2015 Krieg ..................... C07H 21/00 514/44 R

FOREIGN PATENT DOCUMENTS

WO WO-2011/146527 A2 11/2011

OTHER PUBLICATIONS

Dziedzic et al., "Simultaneous siRNA-mediated silencing of pairs of genes coding for enzymes involved in glycosaminoglycan synthesis," Acta Biochimica Polonica, May 14, 2012, 59(2):293-298.

(Continued)

*Primary Examiner* — J. E. Angell
(74) *Attorney, Agent, or Firm* — Foley & Lardner LLP

(57) ABSTRACT

The present invention provides an antisense oligonucleotide for inhibiting biosynthesis of chondroitin sulfate. The antisense oligonucleotide comprises at least one modified nucleotide, wherein the antisense oligonucleotide suppresses expression of one or both of the chondroitin sulfate N-acetylgalactosaminyltransferase-1 (CSGalNAcT1) gene and the chondroitin sulfate N-acetylgalactosaminyltransferase-2 (CSGalNAcT2) gene.

15 Claims, 13 Drawing Sheets

Specification includes a Sequence Listing.

(56) References Cited

OTHER PUBLICATIONS

Supplementary European Search Report dated Nov. 20, 2020 in EP 18775819.8.

Zhang et al., "Chondroitin Sulfate N-acetylgalactosaminyltransferase-2 Contributes to the Replication of Infectious Bursal Disease Virus via Interaction with the Capsid Protein VP2," Viruses, Mar. 23, 2015, 7(3):1474-1491.

International Search Report dated May 22, 2018, in PCT/JP2018/005909.

Holmborn et al,. "On the Roles and Regulation of Chondroitin Sulfate and Heparan Sulfate in Zebrafish Pharyngeal Cartilage Morphogenesis," Journal of Biological Chemistry, Sep. 28, 2012, 287(40):33905-33916.

Takeuchi, Kosei, "Amelioration of neuronal injury by the expressional regulation of the glycosaminoglycan," H. Jpn. Biochem. Soc., 2015, 87:744-748, with partial English translation of indicated portion.

Takeuchi et al., "Chondroitin sulphate N-acetylgalactosaminyl-transferase-1 inhibits recovery from neural injury," Nature Communications, 2013, 4(2740):1-11, with 27 pages of Supplementary Information.

Takeuchi et al., "In vivo regulation of chondroitin sulfate gene to recovery from spinal cord injury and brain infarction," Journal of Neurochemistry, Aug. 2017, 142(Suppl):118, MTU05-16.

Watanabe et al., "Chondroitin sulfate N-acetylgalactosaminyltransferase-1 is required for normal cartilage development," Biochem. J., 2010, 432:47-55.

Kohiga et al., "Design Strategy of Antisense Nucleic Acid Medicine," New Trends of Drug Discovery Research 5, Drug Discovery Series (8), 2016, 148:100-104, with English translation.

* cited by examiner

A

B

A

B

A

B

A

B

A

B

ANTISENSE NUCLEIC ACID FOR INHIBITING BIOSYNTHESIS OF CHONDROITIN SULFATE

CROSS-REFERENCE TO RELATED APPLICATIONS

This application is the U.S. National Stage of PCT/JP2018/005909, filed Feb. 20, 2018, which claims priority to JP 2017-072315, filed Mar. 31, 2017.

Please add the following on page 1 of the specification after the title:

The instant application contains a Sequence Listing which has been submitted in ASCII format via EFS-WEB and is hereby incorporated by reference in its entirety. Said ASCII copy, created on Sep. 25, 2019, is named sequence.txt and is 63,518 bytes.

TECHNICAL FIELD

The present invention relates to an antisense nucleic acid for inhibiting biosynthesis of chondroitin sulfate.

BACKGROUND ART

The spinal cord injury (SCI) is a disease state in which the spinal cord is injured typically by application of strong pressure to the spinal column. Once injured, the central nervous system including the spinal cord is never restored and regenerated, and therefore patients having spinal cord injury often suffer from severe motor function disorders.

Chondroitin sulfate (CS) is a type of glycosaminoglycan which is widely distributed in extracellular matrixes of animals. Chondroitin sulfate has a structure in which sulfuric acid is bonded to a sugar chain in which two sugars: D-glucuronic acid (GlcA) and N-acetyl-D-galactosamine are repeated. It is known that after injury of the spinal cord, chondroitin sulfate is produced in the spinal cord, and the produced chondroitin sulfate is a potent inhibitor of axon regeneration.

Chondroitin sulfate N-acetylgalactosaminyltransferase-1 (CSGalNAcT1) and chondroitin sulfate N-acetylgalactosaminyltransferase-2 (CSGalNAcT2) are enzymes which are involved in biosynthesis of chondroitin sulfate.

The present inventors have reported that in CSGalNAcT1 knockout mice, chondroitin sulfate synthesis after injury of the spinal cord declined, and recovery from spinal cord injury is promoted (Non Patent Literatures 1 and 2)

CITATION LIST

Non Patent Literature

Non Patent Literature 1: Watanabe, Y., et al., Chondroitin sulfate N-acetylgalactosaminyltransferase-1 is required for normal cartilage development. Biochem. J., 2010, 432: 47-55

Non Patent Literature 2: Takeuchi, K., et al., Chondroitin sulphate N-acetylgalactosaminyltransferase-1 inhibits recovery from neural injury. Nature Communication, 2013, 4: 2740

SUMMARY OF INVENTION

Technical Problem

It is an object of the present invention to provide an antisense oligonucleotide for inhibiting biosynthesis of chondroitin sulfate.

Solution to Problem

The present inventors have extensively conducted studies for achieving the above-described object, and resultantly found that an antisense oligonucleotide which suppresses one or both of the CSGalNAcT1 gene and the CSGalNAcT2 gene inhibits biosynthesis of chondroitin sulfate, reduces the amount of chondroitin sulfate, and can be used for treatment of diseases or conditions related to an increase in chondroitin sulfate, such as spinal cord injury, leading to completion of the present invention.

That is, the present invention includes the following.

[1] An antisense oligonucleotide comprising at least one modified nucleotide, wherein the antisense oligonucleotide suppresses expression of one or both of the chondroitin sulfate N-acetylgalactosaminyltransferase-1 (CSGalNAcT1) gene and the chondroitin sulfate N-acetylgalactosaminyltransferase-2 (CSGalNAcT2) gene.

[2] The antisense oligonucleotide according to [1], wherein the antisense oligonucleotide comprises a nucleotide sequence of 11 to 15 contiguous nucleic acid bases of a sequence selected from the group consisting of SEQ ID NOS: 1 to 3, 5 to 111, 113, 115, 116, 119 to 123, 125, 131 to 137, 139 to 145, 148 to 151, 153, 154, 161 and 162, or a nucleotide sequence derived therefrom by substitution, deletion or insertion of one or two nucleic acid bases.

[3] The antisense oligonucleotide according to [2], wherein the antisense oligonucleotide comprises a nucleotide sequence of 11 to 15 contiguous nucleic acid bases of sequence selected from the group consisting of SEQ ID NOS: 1, 9, 16, 18, 21 to 30, 35, 37, 39, 40, 49 to 52, 54, 55, 57 to 59, 62, 63, 67, 88, 89, 102, 107, 108, 113, 115, 134, 140, 141, 144, 154, 161 and 162, or a nucleotide sequence derived therefrom by substitution, deletion or insertion of one or two nucleic acid bases.

[4] The antisense oligonucleotide according to [1], wherein the antisense oligonucleotide comprises a nucleotide sequence of 11 to 15 contiguous nucleic acid bases of a sequence selected from the group consisting of SEQ ID NOS: 18, 35, 52, 57, 88, 108, 113, 115, 134, 140, 141, 142, 154, 155, 156, 161 and 162, or a nucleotide sequence derived therefrom by substitution, deletion or insertion of one or two nucleic acid bases.

[5] The antisense oligonucleotide according to [1], wherein the antisense oligonucleotide consists of a nucleotide sequence having no mismatch or 1 to 4 mismatches with part of CSGalNAcT1 mRNA, and no mismatch or 1 to 4 mismatches with part of CSGalNAcT2 mRNA.

[6] The antisense oligonucleotide according to [5], wherein the antisense oligonucleotide consists of a nucleotide sequence having no mismatch with part of CSGalNAcT1 mRNA, and 1 to 4 mismatches with part of CSGalNAcT2 mRNA.

[7] The antisense oligonucleotide according to [5], wherein the antisense oligonucleotide consists of a nucleotide sequence having 1 to 4 mismatches with part of CSGalNAcT1 mRNA, and no mismatch with part of CSGalNAcT2 mRNA.

[8] The antisense oligonucleotide according to [5], wherein the antisense oligonucleotide consists of a nucleotide sequence having no mismatch with part of CSGalNAcT1 mRNA, and no mismatch with part of CSGalNAcT2 mRNA.

[9] The antisense oligonucleotide according to [2], comprising a nucleotide sequence of 11 to 15 contiguous nucleic acid bases of a sequence selected from the group consisting of SEQ ID NOS: 1 to 3, 5 to 58, 108 to 111, 113, 115, 116, 119 to 123, 125, 161 and 162, or a nucleotide sequence derived therefrom by substitution, deletion or insertion of one or two nucleic acid bases, and consists of a nucleotide sequence having no mismatch or 1 to 4 mismatches with part of a sequence as set forth in SEQ ID NO: 164.

[10] The antisense oligonucleotide according to [2], wherein the antisense oligonucleotide comprises a nucleotide sequence of 11 to 15 contiguous nucleic acid bases of a sequence selected from the group consisting of SEQ ID NOS: 49 to 107, 131 to 137, 139 to 145, 148 to 151, 153 and 154, or a nucleotide sequence derived therefrom by substitution, deletion or insertion of one or two nucleic acid bases, and consists of a nucleotide sequence having no mismatch or 1 to 4 mismatches with part of a sequence as set forth in SEQ ID NO: 165.

[11] The antisense oligonucleotide according to any one of [1] to [10], wherein the antisense oligonucleotide suppresses expression of one or both of the CSGalNAcT1 gene and the CSGalNAcT2 gene by 20% or more.

[12] The antisense oligonucleotide according to any one of [1] to [11], wherein the antisense oligonucleotide is 11 to 20 bases in length.

[13] The antisense oligonucleotide according to any one of [1] to [12], wherein the modified nucleotide comprises a bicyclic sugar.

[14] The antisense oligonucleotide according to any one of [1] to [13], wherein at least one internucleoside bond is a phosphorothioate bond.

[15] The antisense oligonucleotide according to any one of [1] to [14], wherein the modified nucleotide comprises 5-methylcytosine.

[16] The antisense oligonucleotide according to any one of [1] to [15], wherein the antisense oligonucleotide is a gapmer.

[17] A pharmaceutical composition for treating a disease or a condition related to an increase in chondroitin sulfate, the pharmaceutical composition comprising the antisense oligonucleotide according to any one of [1] to [16].

[18] The pharmaceutical composition according to [17], wherein the disease or the condition is spinal cord injury.

The disclosure of JP Patent Application No. 2017-072315 which forms the basis for priority for the present specification is herein incorporated.

Advantageous Effects of Invention

According to the present invention, an antisense oligonucleotide for inhibiting biosynthesis of chondroitin sulfate is provided.

DESCRIPTION OF EMBODIMENTS

Figure 1:
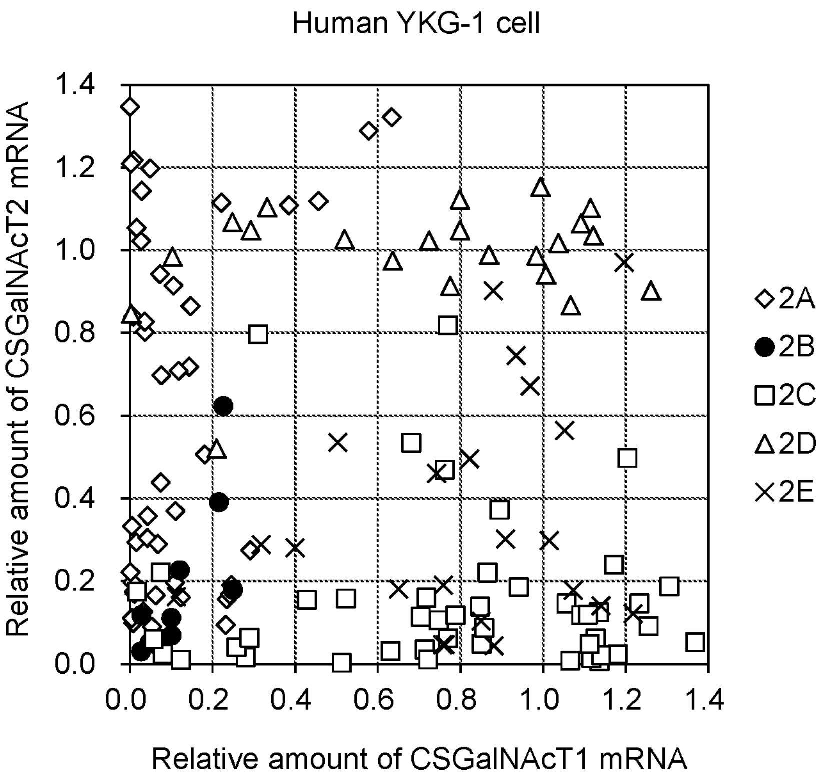
FIG. 1 is a graph showing expression suppressive activity of antisense oligonucleotides on the CSGalNAcT1 and CSGalNAcT2 genes in human YKG-1 cells.
Figure 2:
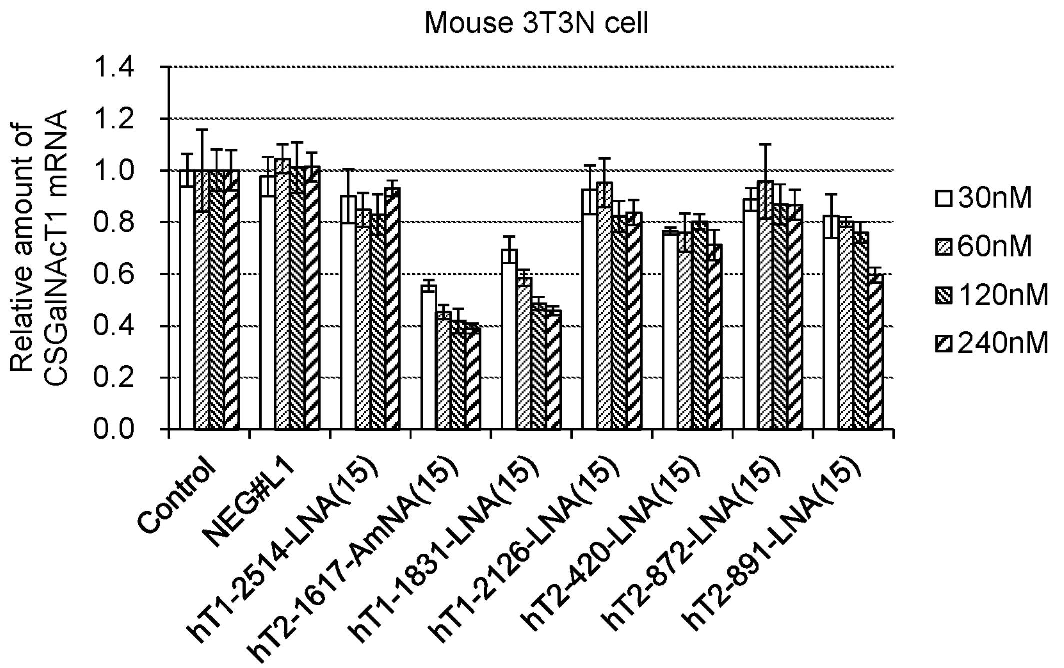
FIG. 2 is a graph showing concentration-dependent expression suppressive activity of antisense oligonucleotides on the CSGalNAcT1 and CSGalNAcT2 genes in mouse 3T3N cells.
Figure 2:
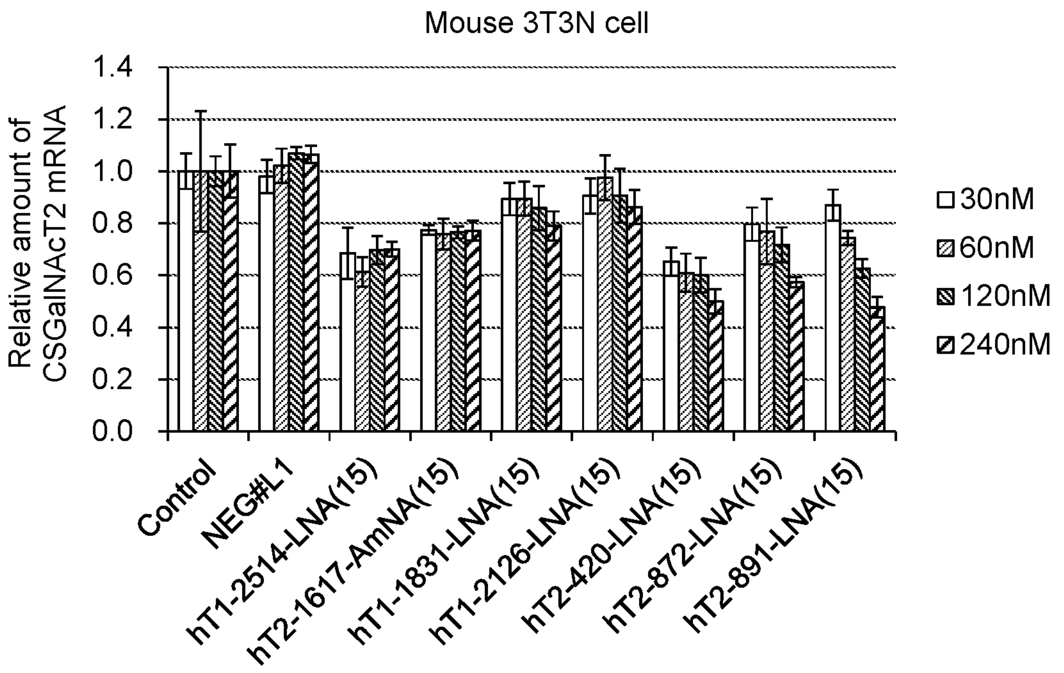
Figure 3:
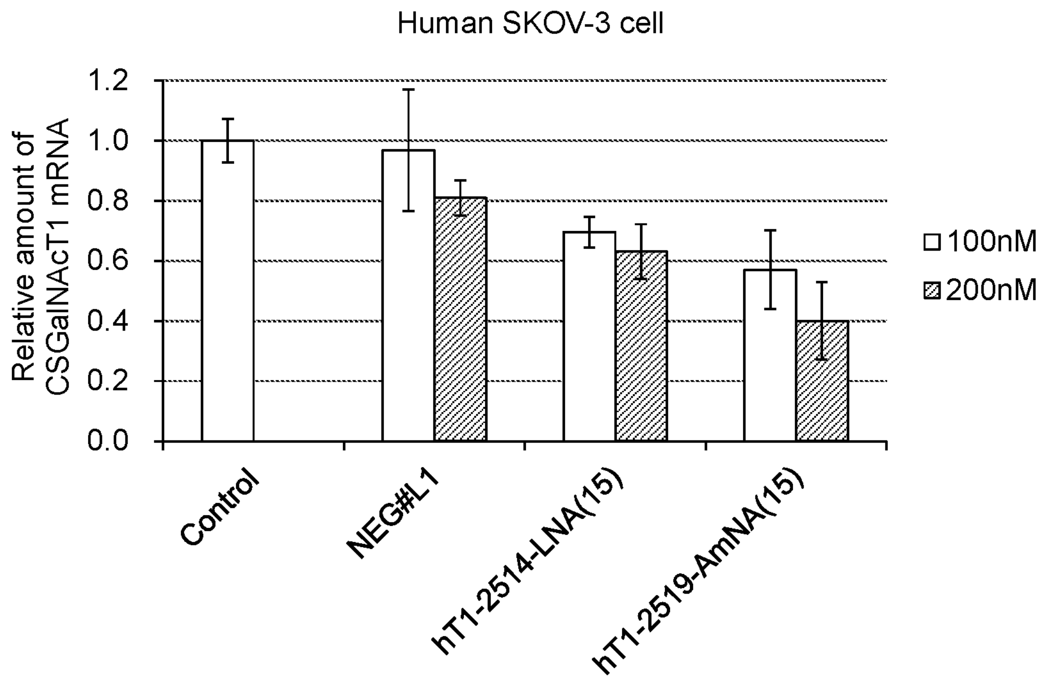
FIG. 3 is a graph showing concentration-dependent expression suppressive activity of antisense oligonucleotides on CSGalNAcT1 and CSGalNAcT2 genes in human SKOV-3 cells.
Figure 3:
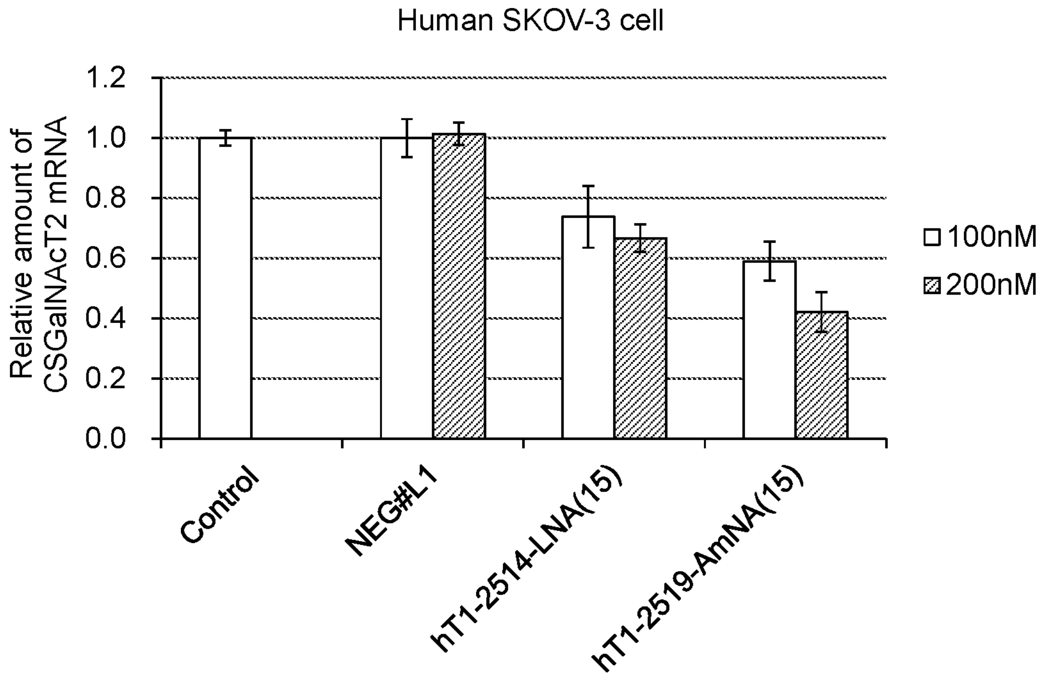
Figure 4:
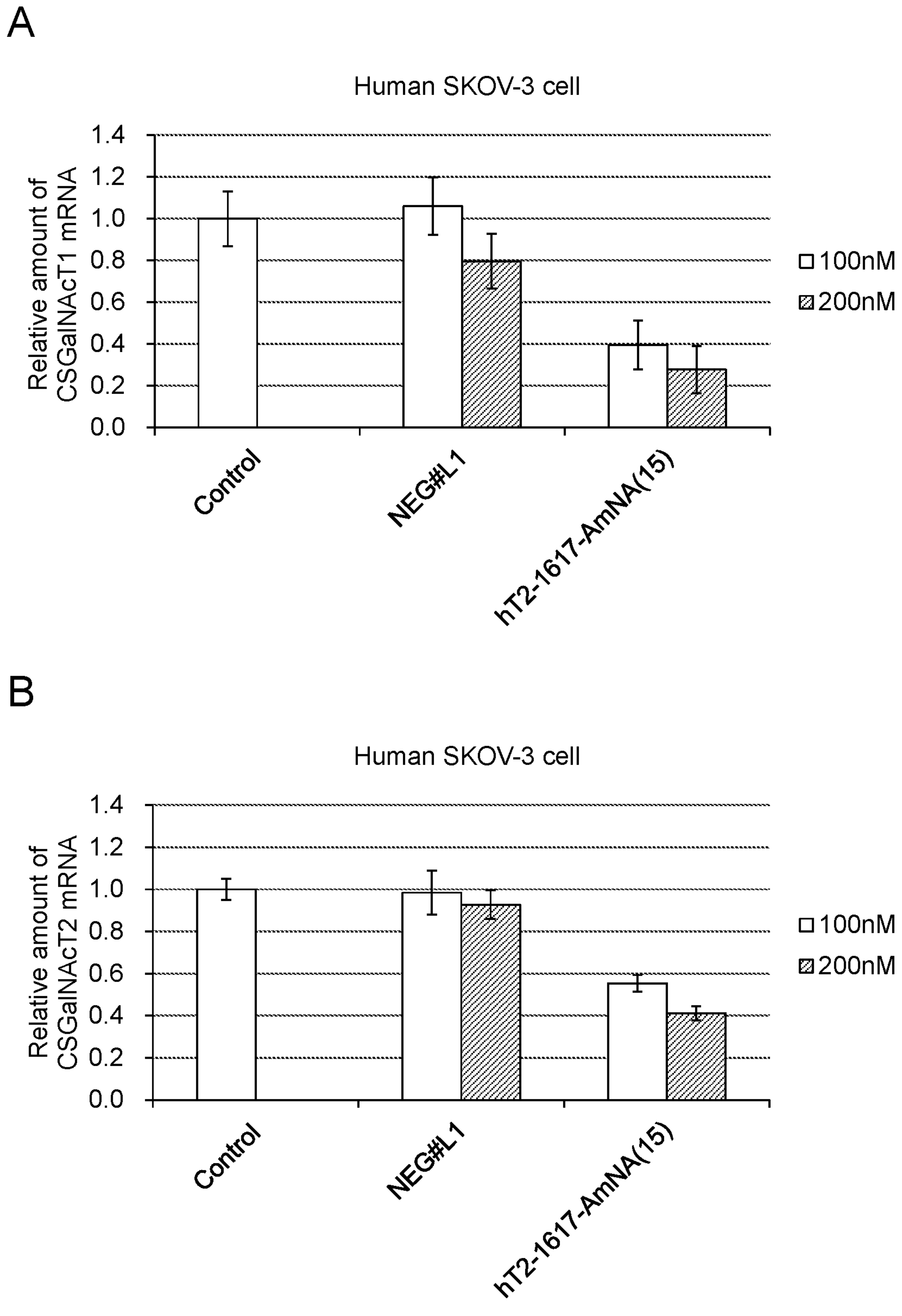
FIG. 4 is a graph showing concentration-dependent expression suppressive activity of antisense oligonucleotides on the CSGalNAcT1 and CSGalNAcT2 genes in human SKOV-3 cells.
Figure 5:
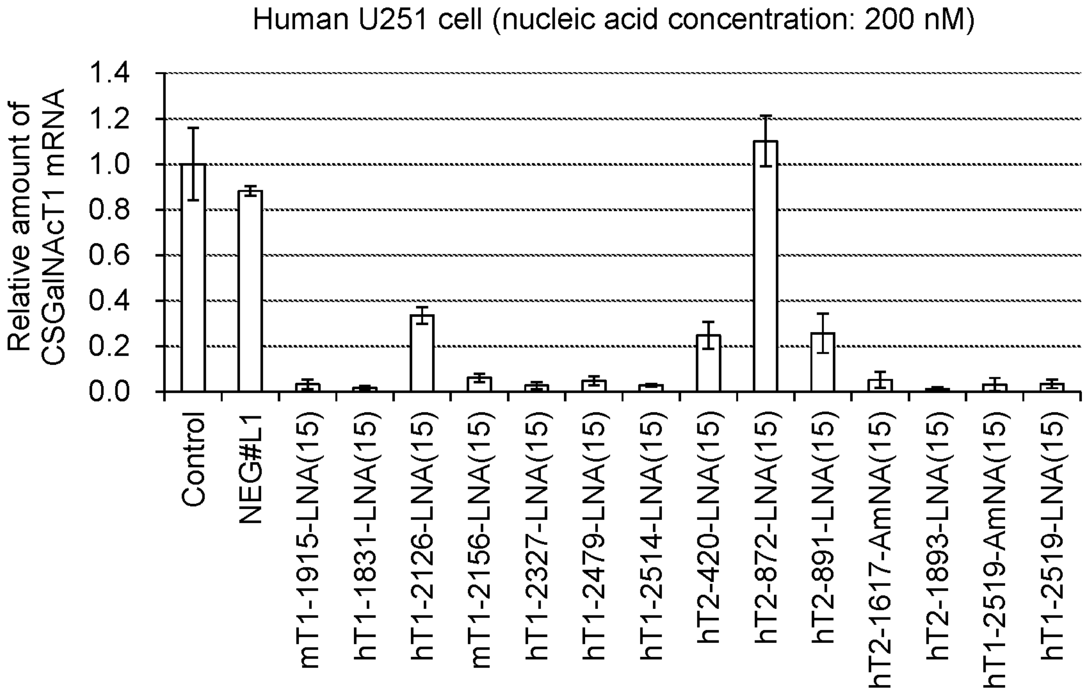
FIG. 5 is a graph showing expression suppressive activity of antisense oligonucleotides on the CSGalNAcT1 and CSGalNAcT2 genes in human U251 cells.
Figure 5:
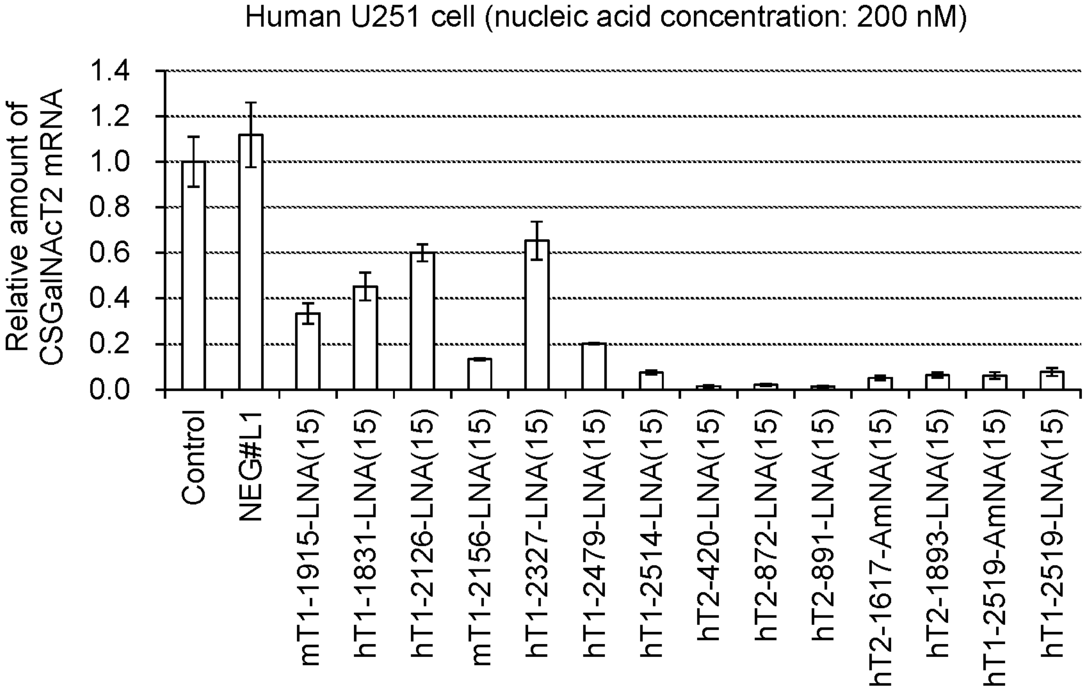
Figure 6:
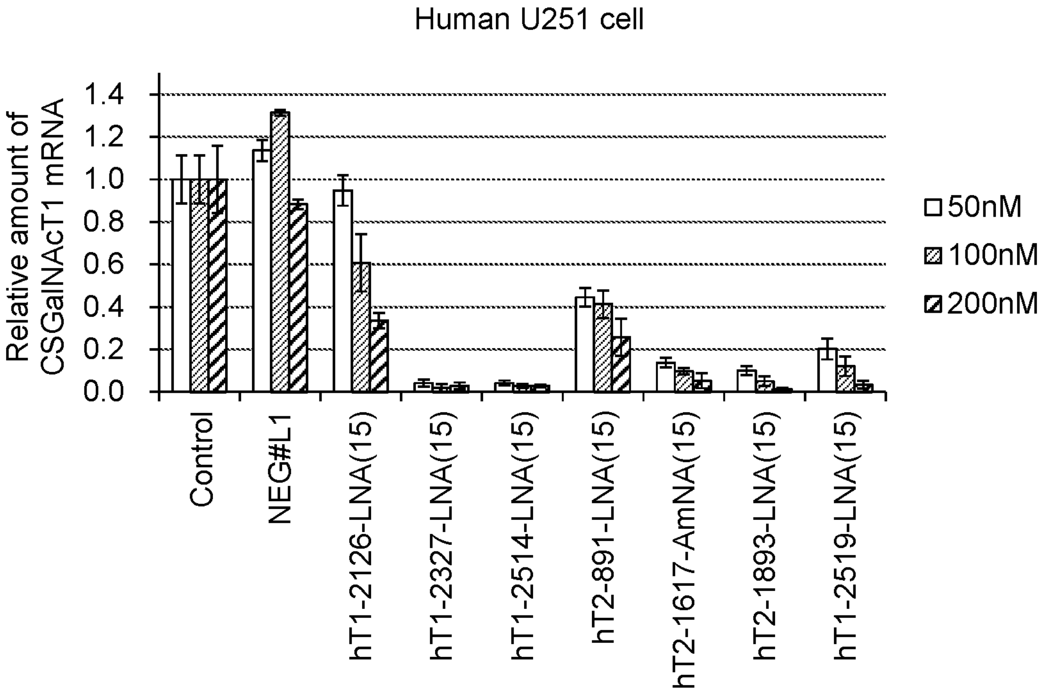
FIG. 6 is a graph showing concentration-dependent expression suppressive activity of antisense oligonucleotides on the CSGalNAcT1 and CSGalNAcT2 genes in human U251 cells.
Figure 6:
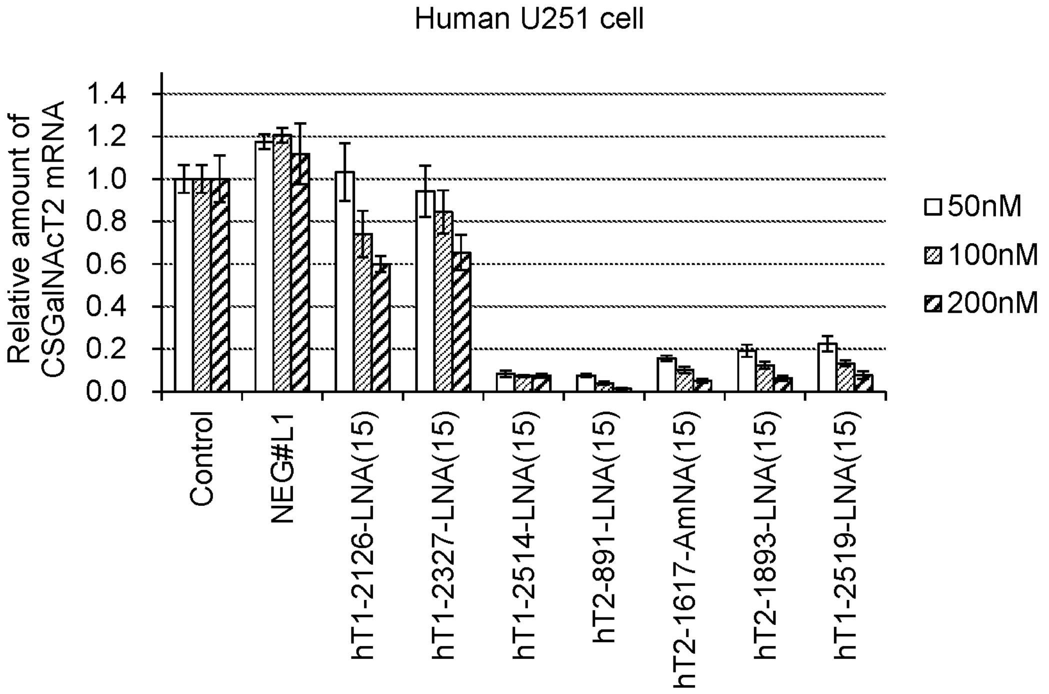
Figure 7:
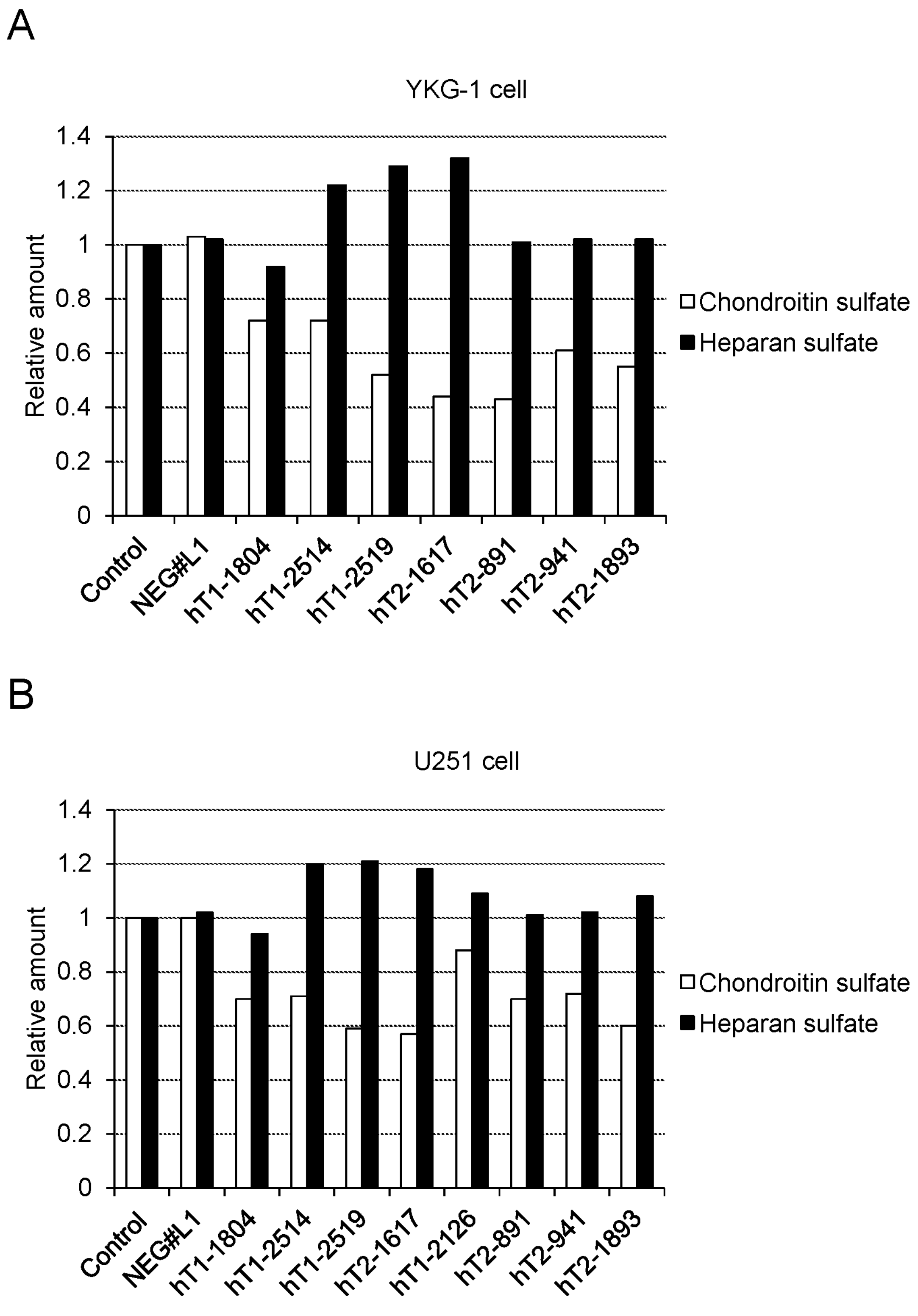
FIG. 7 is a graph showing the effects of antisense oligonucleotides on the amounts of chondroitin sulfate and heparan sulfate.

Hereinafter, the present invention will be described in detail.

(Antisense Oligonucleotide)

The present invention relates to an antisense oligonucleotide. More specifically, the present invention relates to an antisense oligonucleotide for inhibiting biosynthesis of chondroitin sulfate, particularly an antisense oligonucleotide which suppresses one or both of the chondroitin sulfate N-acetylgalactosaminyltransferase-1 (CSGalNAcT1) gene and the chondroitin sulfate N-acetylgalactosaminyltransferase-2 (CSGalNAcT2) gene.

Herein, the CSGalNAcT1 gene and the CSGalNAcT2 gene refer to genes encoding enzymes having an activity that transfers N-acetylgalactosamine (GalNAc) from UDP-GalNAc to the non-reducing end of glucuronic acid. The CSGalNAcT1 gene and the CSGalNAcT2 gene each refer to a gene which is not present in animals (in which central nerve regeneration occurs) more primitive than vertebrate phyla, and came into existence only with vertebrate phyla which can be subject to central nerve injury. The CSGalNAcT1 gene is considered paralogous to the CSGalNAcT1 gene. Origins of the CSGalNAcT1 gene and the CSGalNAcT2 gene are not particularly limited, and are, for example, mammals such as primates (for example crab-eating monkeys, chimpanzees and humans) and nonprimates (for example cattle, pigs, sheep, horses, cats, dogs, guinea pigs, rats and mice), more preferably humans. The CSGalNAcT1 gene and the CSGalNAcT2 gene which are targeted by one antisense oligonucleotide can be derived from the same biological species. The nucleotide sequences of the CSGalNAcT1 gene and the CSGalNAcT2 gene can be obtained from the database in National Center for Biotechnology Information (NCBI). The human CSGalNAcT1 mRNA sequence is set forth in SEQ ID NO: 164 (where the sequence of RNA is set forth as the sequence of DNA). The human CSGalNAcT2 mRNA sequence is set forth in SEQ ID NO: 165 (where the sequence of RNA is set forth as the sequence of DNA). The mouse CSGalNAcT1 mRNA sequence is set forth in SEQ ID NO: 166 (where the sequence of RNA is set forth as the sequence of DNA). The mouse CSGalNAcT2 mRNA sequence is set forth in SEQ ID NO: 167 (where the sequence of RNA is set forth as the sequence of DNA). The rat CSGalNAcT1 mRNA sequence is set forth in SEQ ID NO: 168 (where the sequence of RNA is set forth as the sequence of DNA). The rat CSGalNAcT2 mRNA sequence is set forth in SEQ ID NO: 169 (where the sequence of RNA is set forth as the sequence of DNA). In the present invention, genes encoding modifications of the above-described sequences also fall within the range of the CSGalNAcT1 gene and the CSGalNAcT2 gene as long as translated proteins have similar activity.

Herein, the "antisense nucleic acid" or the "antisense oligonucleotide" refers to a single-stranded oligonucleotide including a nucleotide sequence which can be hybridized to (that is, complementary to) part of mRNA of one or both of CSGalNAcT1 and CSGalNAcT2 that are target genes. Without being bound by theory, in the present invention, the antisense nucleic acid or the antisense oligonucleotide forms a DNA-RNA hybrid with target RNA, and is cleaved by RNase H to break down target RNA, and as a result, expression of the target gene can be suppressed. The region of mRNA of the target gene which can be hybridized by the antisense oligonucleotide can include 3'UTR, 5'UTR, exon, intron, a coding region, a translation initiation region, a translation termination region or other nucleic acid regions.

In an embodiment, the antisense oligonucleotide can suppress expression of the CSGalNAcT1 gene. In another embodiment, the antisense oligonucleotide can suppress expression of the CSGalNAcT2 gene. In still another embodiment, the antisense oligonucleotide can suppress expression of both of the CSGalNAcT1 gene and the CSGalNAcT2 gene. Suppression of both of the CSGalNAcT1 gene and the CSGalNAcT2 gene is preferable because biosynthesis of chondroitin sulfate is efficiently inhibited.

Herein, the "suppression" related to expression of a gene means that the amount (abundance) of mRNA produced by transfer of the gene is reduced. The suppression includes suppression of the amount of mRNA by 20% or more, 30% or more or 40% or more, preferably 50% or more, more preferably 80% or more, 90% or more or 95% or more in comparison with a control. The suppression of expression of a gene may be determined by any of methods known in the art, and in particular, the suppression of expression of a gene can be determined by a method based on PCR such as real-time PCR using cells such as human or mouse cells.

The antisense oligonucleotide according to the present invention can reduce the amount of chondroitin sulfate. The reduction of the amount of chondroitin sulfate can be determined by, for example, the In Cell ELISA assay using an anti-chondroitin sulfate antibody as described in Examples below. The antisense oligonucleotide according to the present invention can reduce the amount of chondroitin sulfate by 10% or more, 20% or more, 30% or more, 40% or more or 50% or more in comparison with a control.

In a preferred embodiment, the antisense oligonucleotide according to the present invention does not reduce the amount of heparan sulfate. Heparan sulfate has been reported to promote axon regeneration (Takeuchi, K., et al., 2013, described above). The heparan sulfate can be determined by, for example, the In Cell ELISA assay using an anti-heparan sulfate antibody as described in Examples below. The antisense oligonucleotide according to the present invention may increase the amount of heparan sulfate (for example by 10% or more) in comparison with a control.

In an embodiment, the antisense oligonucleotide may contain a nucleotide sequence as set forth in one of SEQ ID NOS in Tables 1A to 1G (SEQ ID NOS: 1 to 163) in Example 1 below.

Herein, the "nucleic acid base" or the "base" is a base component of a nucleic acid, and refers to a heterocyclic ring moiety which can be paired with a base of another nucleic acid. Herein, the "nucleotide sequence" means a sequence of contiguous nucleic acid bases in which a sugar forming the nucleic acid, an internucleoside bond or a nucleic acid base modification is not taken into account.

In an embodiment, the nucleotide sequence of the antisense oligonucleotide may be selected from the group consisting of SEQ ID NOS: 1 to 163.

In a preferred embodiment, the nucleotide sequence may be selected from the group consisting of SEQ ID NOS: 1 to 3 and 5 to 48 in Table 1A; SEQ ID NOS: 49 to 58 in Table 1B; SEQ ID NOS: 59 to 107 in Table 1C; SEQ ID NOS: 108 to 111, 115, 116, 119 to 123 and 125 in Table 1D; and SEQ ID NOS: 131 to 137, 139 to 145, 148 to 151 and 153 and 154 in Table 1E below. The antisense oligonucleotides consisting of these nucleotide sequences are shown to suppress expression of one or both of the CSGalNAcT1 gene and the CSGalNAcT2 gene by 20% or more in Example 2 below (Tables 2A to 2E).

In a more preferred embodiment, the nucleotide sequence may be selected from the group consisting of SEQ ID NOS: 1 to 3, 5 to 30, 32, 33 and 35 to 48 in Table 1A; SEQ ID NOS: 49 to 58 in Table 1B; SEQ ID NOS: 59 to 79, 81 to 91 and 93 to 107 in Table 1C; SEQ ID NOS: 108, 111, 115, 121, 122 and 125 in Table 1D; and SEQ ID NOS: 131 to 134, 136, 137, 139 to 145, 148, 149 and 154 in Table 1E. The antisense oligonucleotides consisting of these nucleotide sequences are shown to suppress expression of one or both of the CSGalNAcT1 gene and the CSGalNAcT2 gene by 50% or more in Example 2 (Tables 2A to 2E).

In a still more preferred embodiment, the nucleotide sequence may be selected from the group consisting of SEQ ID NOS: 1 to 3, 5 to 7, 9 to 30, 32 and 35 to 48 in Table 1A; SEQ ID NOS: 49 to 58 in Table 1B; SEQ ID NOS: 59, 60, 62 to 65, 67 to 79, 82 to 91 and 94 to 107 in Table 1C; SEQ ID NOS: 108, 111, 115, 121 and 122 in Table 1D; and SEQ ID NOS: 131 to 134, 136, 137, 140 to 142, 144, 145, 149 and 154 in Table 1E. The antisense oligonucleotides consisting of these nucleotide sequences are shown to suppress expression of one or both of the CSGalNAcT1 gene and the CSGalNAcT2 gene by 70% or more in Example 2 (Tables 2A to 2E).

In a still more preferred embodiment, the nucleotide sequence may be selected from the group consisting of SEQ ID NOS: 1, 9, 16, 18, 21 to 30, 35, 37, 39 and 40 in Table 1A; SEQ ID NOS: 49 to 52, 54, 55, 57 and 58 in Table 1B; SEQ ID NOS: 59, 62, 63, 67, 88, 89, 102 and 107 in Table 1C; and SEQ ID NO: 144 in Table 1E. The antisense oligonucleotides consisting of these nucleotide sequences are shown to suppress expression of both of the CSGalNAcT1 gene and the CSGalNAcT2 gene by 70% or more in Example 2 (Tables 2A to 2E).

In another embodiment, the nucleotide sequence may be selected from SEQ ID NOS: 18 and 35 in Table 1A; SEQ ID NOS: 52 and 57 in Table 1B; SEQ ID NO: 88 in Table 1C; SEQ ID NOS: 108, 113 and 115 in Table 1D; SEQ ID NOS: 134, 140, 141, 142 and 154 in Table 1E; SEQ ID NOS: 155 and 156 in Table 1F; and SEQ ID NOS: 161 and 162 in Table 1G. The antisense oligonucleotides consisting of these nucleotide sequences are shown to suppress expression of one or both of the CSGalNAcT1 gene and the CSGalNAcT2 gene significantly and/or reduce the amount of chondroitin sulfate in Examples 3 to 7 (FIGS. 2 to 7) and the like. More specifically, the nucleotide sequence may be SEQ ID NO: 52 or 155. The antisense oligonucleotide consisting of a nucleotide sequence as set forth in SEQ ID NO: 52 or 155 is shown to promote recovery from of motor function in spinal cord injury in Examples 13 and 14.

In an embodiment, the antisense oligonucleotide may contain a nucleotide sequence of 11 to 15 contiguous nucleic acid bases of the above-described nucleotide sequence. The number of contiguous nucleic acid bases of the nucleotide sequence may be 11 or more, 12 or more, 13 or more, 14 or more, or 15. The antisense oligonucleotide may consist of a nucleotide sequence of 11 to 15 contiguous nucleic acid bases of the above-described nucleotide sequence.

In another embodiment, the antisense oligonucleotide may contain a nucleotide sequence derived from the nucleotide sequence of 11 to 15 contiguous nucleic acid bases of the above-described nucleotide sequence by substitution, deletion or insertion (particularly, substitution) of one or two nucleic acid bases.

In the present invention, the nucleotide sequence of the antisense oligonucleotide may have no mismatch or 1 to 4 (or 1 to 3 or 1 to 2) mismatches with part of CSGalNAcT1 mRNA. In the present invention, the nucleotide sequence of the antisense oligonucleotide may have no mismatch or 1 to 4 (or 1 to 3 or 1 to 2) mismatches with part of CSGalNAcT2 mRNA. The “part” of mRNA refers to a target region in mRNA, to which the antisense oligonucleotide can be hybridized by base pairing, and the target region can be identical in the number of bases in length to the antisense oligonucleotide. The “mismatch” means that a nucleic acid base of a first nucleic acid cannot be base-paired with (is not complementary to) a nucleic acid base corresponding to a second nucleic acid.

In a preferred embodiment, the nucleotide sequence of the antisense oligonucleotide has no mismatch or 1 to 4 (or 1 to 3 or 1 to 2) mismatches with part of CSGalNAcT1 mRNA, and no mismatch or 1 to 4 (or 1 to 3 or 1 to 2) mismatches with part of CSGalNAcT2 mRNA. Such a nucleotide sequence can be designed by selecting a region having high homology between CSGalNAcT1 mRNA and CSGalNAcT2 mRNA. Sequence homology can be analyzed by, for example, BLAST analysis using an algorism known in the art (see, for example, Altschul, S. F., et al., Basic local alignment search tool. 1990, J. Mol. Biol. 215: 403-410).

The nucleotide sequence of the antisense oligonucleotide may have no mismatch with part of CSGalNAcT1 mRNA, and 1 to 4 (or 1 to 3 or 1 to 2) mismatches with part of CSGalNAcT2 mRNA. Examples of such nucleotide sequences are shown in Table 1A in Example 1 below.

The nucleotide sequence of the antisense oligonucleotide may have 1 to 4 (or 1 to 3 or 1 to 2) mismatches with part of CSGalNAcT1 mRNA, and no mismatch with part of CSGalNAcT2 mRNA. Examples of such nucleotide sequences are shown in Table 1C in Example 1 below.

In a still more preferred embodiment, the nucleotide sequence of the antisense oligonucleotide has no mismatch with part of CSGalNAcT1 mRNA, and no mismatch with part of CSGalNAcT2 mRNA. Table 1B in Example 1 below shows nucleotide sequences having no mismatch with part of human CSGalNAcT1 mRNA, and no mismatch with part of human CSGalNAcT2 mRNA. The antisense oligonucleotides having these nucleotide sequences are shown to suppress both of the CSGalNAcT1 gene and the CSGalNAcT2 gene significantly in Example 2 (FIG. 1 and Table 2B).

In an embodiment, the antisense oligonucleotide containing a nucleotide sequence of 11 to 15 contiguous nucleic acid bases of a nucleotide sequence as set forth in one of nucleotide sequences in Table 1A (SEQ ID NOS: 1 to 48), Table 1B (SEQ ID NOS: 49 to 58) and Table 1D (SEQ ID NOS: 108 to 130) in Example 1 below, or a nucleotide sequence derived therefrom by substitution, deletion or insertion of one or two nucleic acid bases may have no mismatch or 1 to 4 (or 1 to 3 or 1 to 2) mismatches with part of human CSGalNAcT1 mRNA (SEQ ID NO: 164).

In another embodiment, the antisense oligonucleotide containing a nucleotide sequence of 11 to 15 contiguous nucleic acid bases of a nucleotide sequence as set forth in one of nucleotide sequences in Table 1B (SEQ ID NOS: 49 to 58), Table 1C (SEQ ID NOS: 59 to 107) and Table 1E (SEQ ID NOS: 131 to 154) in Examples below, or a nucleotide sequence derived therefrom by substitution, deletion or insertion of one or two nucleic acid bases may have no mismatch or 1 to 4 (or 1 to 3 or 1 to 2) mismatches with part of human CSGalNAcT2 mRNA (SEQ ID NO: 165).

In an embodiment, the antisense oligonucleotide containing a nucleotide sequence of 11 to 15 contiguous nucleic acid bases of a nucleotide sequence selected from SEQ ID NOS: 159 to 162 in Table 1G in Examples below, or a nucleotide sequence derived therefrom by substitution, deletion or insertion of one or two nucleic acid bases may have no mismatch or 1 to 4 (or 1 to 3 or 1 to 2) mismatches with part of mouse CSGalNAcT1 mRNA (SEQ ID NO: 166) or human CSGalNAcT1 mRNA (SEQ ID NO: 164).

In another embodiment, the antisense oligonucleotide containing a nucleotide sequence of 11 to 15 contiguous nucleic acid bases of a nucleotide sequence as set forth in SEQ ID NO: 163 in Table 1G in Examples below, or a nucleotide sequence derived therefrom by substitution, deletion or insertion of one or two nucleic acid bases may have no mismatch or 1 to 4 (or 1 to 3 or 1 to 2) mismatches with part of mouse CSGalNAcT2 mRNA (SEQ ID NO: 167) or human CSGalNAcT2 mRNA (SEQ ID NO: 165).

The antisense oligonucleotide of the present invention may be 11 to 20 bases in length, 12 to 19 bases in length, 13 to 18 bases in length, 14 to 17 bases in length or 14 to 16 bases in length.

In the present invention, the antisense oligonucleotide can contain natural (nonmodified) nucleotide (deoxyribonucleotide, ribonucleotide or both) and/or unnatural (modified) nucleotide.

In general, the “nucleoside” is a combination of a sugar and a nucleic acid base. The “nucleotide” further contains a phosphate group covalently bonded to a sugar moiety of the nucleoside. In general, the phosphate group forms an internucleoside bond of oligonucleotides. The oligonucleotide is formed by covalent bonding of nucleotides adjacent to each other, and forms a linear polymer oligonucleotide.

Herein, the “modified nucleoside” means a nucleoside having a modified sugar and/or a modified base moiety independently. The “modified nucleotide” means a nucleotide having a modified internucleoside bond, a modified sugar and/or a modified base moiety independently. An oligonucleotide containing a modified nucleotide is more preferable in comparison with a nonmodified type because of desired properties such as enhanced affinity for target nucleic acids and increased nuclease resistance.

Herein, the “modified internucleoside bond” refers to an internucleoside bond in which a naturally occurring internucleoside bond (that is, phosphodiester bond) is substituted or subjected to some change. Examples of the modified internucleoside bond include, but are not limited to, a phosphorothioate bond, a phosphorodithioate bond, a phosphorodiamidate bond and a phosphoroamidate bond. The phosphorothioate bond refers to an internucleoside bond in which the non-bridged oxygen atom of a phosphodiester bond is replaced by a sulfur atom. The modified internucleoside bond is preferably a bond having nuclease resistance higher than that of a naturally occurring internucleoside bond.

Herein, the "modified base moiety" refers to any nucleic acid base other than adenine, cytosine, guanine, thymine or uracil. The "nonmodified base moiety" or the "natural nucleic acid base" refers to adenine (A) and guanine (G) which are purine bases, and thymine (T), cytosine (C) and uracil (U) which are pyrimidine bases. Examples of the modified base moiety include, but are not limited to, 5-methylcytosine, 5-fluorocytosine, 5-bromocytosine or 5-iodocytosine; 5-fluorouracil, 5-bromo uracil, 5-iodouracil or 5-hydroxyuracil; 2-thiothymine; N6-methyladenine or 8-bromoadenine; and N2-methylguanine or 8-bromoguanine.

Herein, the "modified sugar" refers to a sugar in which a natural sugar moiety (that is, a sugar moiety present in DNA (2'-H) or RNA (2'-OH)) is substituted or subjected to some change. The modified sugar can impart enhanced affinity for target nucleic acids, increased nuclease resistance, and the like to an oligonucleotide. Examples of the modified sugar include bicyclic sugars, 5'-vinyl, 5'-methyl, 4'-S, 2'-F, 2'-$OCH_3$ (2'-methoxy or 2'-O-methyl group) and 2'-$O(CH_2)_2OCH_3$ substituents.

Herein, the "bicyclic sugar" refers to a sugar having two rings. A nucleic acid containing a bicyclic sugar moiety is generally referred to as a bridged nucleic acid (BNA). The bicyclic sugar may be a sugar in which the 2'-position carbon atom and the 4'-position carbon atom are bridged by two or more atoms. Examples of the bicyclic sugar include, but are not limited to, sugars having a methyleneoxy (4'-$CH_2$—O-2') bridge (LNA™, also known as 2',4'-BNA), sugars having an ethyleneoxy (4'-$(CH_2)_2$—O-2') bridge (also known as ENA), sugars having a 4'-$CH(CH_3)$—O-2 bridge (cEt, constrained ethyl), sugars having a 4'-$CH(CH_2OCH_3)$—O-2' bridge (cMOE, constrained MOE), and sugars having an amide bridge (AmNA, Amido-bridged nucleic acid). Examples of the sugar having an amide bridge include sugars having a 4'-C(O)—$N(CH_3)$-2' bridge. For the structures of sugars having an amide bridge and methods for preparing the sugars, see, for example, Yahara, A., et al., Amido-bridged nucleic acids (AmNAs): synthesis, duplex stability, nuclease resistance, and in vitro antisense potency, ChemBioChem, 2012, 13(7): 2513-2516, Yamamoto, T., et al., Amido-bridged nucleic acids with small hydrophobic residues enhance hepatic tropism of antisense oligonucleotides in vivo, Org. Biomol. Chem., 2015, 13: 3757-3765, and International Publication No. WO 2011/052436. For sugars having a 4'-$CH(CH_3)$—O-2' bridge (cEt) and sugars having a 4'-$CH(CH_2OCH_3)$—O-2' bridge (cMOE), see Punit, P. S., et al., Short antisense oligonucleotides with novel 2'-4' conformationally restricted nucleoside analogues show improved potency without increased toxicity in animals, J. Med. Chem., 2009, 52(1): 10-13.

In the present invention, the antisense oligonucleotide may contain a mimic nucleotide such as a peptide nucleic acid or a morpholino nucleic acid.

In general, different nucleotides in the same chain can be subjected to different modifications independently. Further, for example, for increasing nuclease resistance, identical nucleotides may have a modified internucleoside bond (for example a phosphorothioate bond), and further, a modified sugar (for example a bicyclic sugar). In addition, identical nucleotides may have a modified base moiety (for example 5-methylcytosine), and further, a modified sugar (for example a bicyclic sugar).

In an embodiment, the antisense oligonucleotide may contain at least one modified nucleotide. The modified nucleotide can contain a modified internucleoside bond, a modified sugar moiety and/or a modified base moiety.

In an embodiment, at least one of internucleoside bonds in the antisense oligonucleotide may be a modified internucleoside bond. At least 70%, at least 80%, at least 90% or 100% of internucleoside bonds in the antisense oligonucleotide may be modified internucleoside bonds. The modified internucleoside bond may be a phosphorothioate bond.

In an embodiment, at least one of sugar moieties in the antisense oligonucleotide may be bicyclic sugar. The bicyclic sugar may have a methyleneoxy (4'-$CH_2$—O-2') bridge or an amide bridge (for example a 4'-C(O)—$N(CH_3)$-2' bridge).

In an embodiment, at least one of nucleic acid bases in the antisense oligonucleotide may be a modified base moiety. The modified base moiety may be 5-methylcytosine.

In a certain embodiment, the antisense oligonucleotide may be a gapmer. Herein, the "gapmer" refers to an oligonucleotide including a central region containing at least four contiguous deoxyribonucleosides (DNA gap region), and regions positioned on the 5'-end side and the 3'-end side of the central region and containing an unnatural nucleoside (5'-wing region and 3'-wing region). The DNA gap region may be 4 to 16 bases in length, 5 to 14 bases in length, 6 to 12 bases in length, or 8 to 10 bases in length. The 5'-wing region and the 3'-wing region may be each independently 1 to 6 bases in length, 1 to 5 bases in length, or 2 to 4 bases in length. The 5'-wing region and the 3'-wing region are only required to contain at least one unnatural nucleoside, and may contain a natural nucleoside. The 5'-wing region and the 3'-wing region may each contain one or more types of unnatural nucleosides. All nucleosides in the 5'-wing region and 3'-wing region may be unnatural nucleosides. Alternatively, the nucleosides at one or both of the 5'-end and the 3'-end (particularly 3'-end) of the gapmer may be natural nucleosides (particularly deoxyribonucleosides). The unnatural nucleosides present in the 5'-wing region and the 3'-wing region may be nucleosides having a bicyclic sugar. The bicyclic sugar may be a sugar having a methyleneoxy (4'-$CH_2$—O-2') bridge, or a sugar having an amide bridge (for example a 4'-C(O)—$N(CH_3)$-2' bridge). The unnatural nucleosides present in the 5'-wing region and the 3'-wing region may contain a modified base moiety (for example 5-methylcytosine).

The antisense oligonucleotide of the present invention can be produced by a method known in the art. The antisense oligonucleotide can be produced by, for example, synthesis using a commercially available automatic nucleic acid synthesis apparatus, followed by purification using a reversed phase column or the like. Alternatively, the antisense oligonucleotide can be obtained by specifying a nucleotide sequence, a modified moiety and a type, and ordering from a maker (for example, GeneDesign, Inc.).

The antisense oligonucleotide of the present invention suppresses expression of one or both of the CSGalNAcT1 gene and the CSGalNAcT2 gene to inhibit biosynthesis of chondroitin, and as a result, the amount of chondroitin sulfate can be reduced. An increase in chondroitin sulfate after injury of the spinal cord inhibits axon regeneration, and hinders recovery from spinal cord injury. Spinal cord injury can be treated (recovery from spinal cord injury can be promoted) by reducing the amount of chondroitin sulfate using the antisense oligonucleotide of the present invention. On the other hand, heparan sulfate has been reported to promote axon regeneration (Takeuchi, K., et al., 2013, described above). The antisense oligonucleotide of the present invention can reduce the amount of chondroitin sulfate without reduction of the amount of heparan sulfate, so that spinal cord injury can be effectively treated.

(Pharmaceutical Composition)

The present invention provides a pharmaceutical composition containing an antisense oligonucleotide according to an embodiment of the present invention. The pharmaceutical composition can be used for treating a disease or a condition related to an increase in chondroitin sulfate.

Examples of the disease or condition related to an increase in chondroitin sulfate include, but are not limited to, spinal cord injury, cerebral vascular disorders (for example, cerebral injury and cerebral ischemia), digestive system diseases (for example inflammatory colitis), and cutaneous injury or inflammation.

Herein, the spinal cord injury is a disease state in which the spinal cord is injured. The cause of spinal cord injury does not matter. The spinal cord injury may be traumatic spinal cord injury. The spinal cord injury includes complete spinal cord injury and incomplete spinal cord injury. The complete spinal cord injury refers to a state in which the spinal cord is transversely discontinued. The incomplete spinal cord injury refers to a state in which the spinal cord is partially injured. The spinal cord injury develops various disorders such as motor function disorders, sensory disorders and autonomic nerve disorders.

Herein, the "treatment" can include alleviation or cure of symptoms (for example motor function disorders) caused by spinal cord injury in subjects having spinal cord injury.

Scars formed as a result of restoration of tissues after injury of the spinal cord are generally considered to inhibit regeneration of nerves. Thus, recovery from spinal cord injury can be promoted by suppressing formation of scars. The pharmaceutical composition according to the present invention may be used for suppressing or reducing formation of scars after injury of the spinal cord.

The pharmaceutical composition may further contain any pharmaceutical aid that is usually used in the field of preparations. Herein, examples of the pharmaceutical aid that can be used include various carriers and additives such as pharmaceutically acceptable carriers (solid or liquid carriers), excipients, stabilizers, disintegrating agents, surfactants, binding agents, lubricants, emulsifiers, suspensions, antioxidants, fragrances, fillers, solubilizing agents, coating agents, colorants, flavoring agents, preservatives and buffers. Specific examples of the pharmaceutical aid include water, physiological saline, other aqueous solvents, pharmaceutical acceptable organic solvents, mannitol, lactose, starch, microcrystalline cellulose, glucose, calcium, polyvinyl alcohol, collagen, polyvinyl pyrrolidone, carboxyvinyl polymers, sodium alginate, water-soluble dextran, water-soluble dextrin, carboxymethyl starch sodium, pectin, gum Arabic, xanthan gum, casein, gelatin, agar, propylene glycol, polyethylene glycol, petroleum jerry, paraffin, glycerin, stearyl alcohol, stearic acid and sorbitol. The pharmaceutical aids can be selected appropriately or in combination according to the dosage form of a preparations.

The pharmaceutical composition can be orally or parenterally administered to a subject. Examples of the parenteral administration include, but are not limited to, intramedullary administration and local administration. It is preferable to locally administer the pharmaceutical composition directly to the site of injury for efficiently obtaining a treatment effect. Further, the pharmaceutical composition can be continually administered to the site of injury using a continual injection pump. Further, the pharmaceutical composition may be retained on the site of injury with the pharmaceutical composition carried in a sponge. The pharmaceutical composition may be formed into preparations such as injections and drops. Those skilled in the art can produce these preparations by conventional methods.

The pharmaceutical composition may be administered in a therapeutically effective amount. The specific dosage of the pharmaceutical composition is determined for each subject at the discretion of, for example, a physician, depending on the patient's severity, systemic health condition, age, sex, weight, tolerance to treatment and the like. For example, the pharmaceutical composition may be administered in an amount such that the dosage of the antisense oligonucleotide is 0.000001 mg/kg of weight/day to 1000 mg/kg of weight/day, or 0.001 mg/kg of weight/day to 1 mg/kg of weight/day, or 0.005 mg/kg of weight/day to 0.5 mg/kg of weight/day, or 0.01 mg/kg of weight/day to 0.1 mg/kg of weight/day. The pharmaceutical composition can be administered in a single dose or a plurality of doses, and for example, the pharmaceutical composition may be administered to the subject several times or some dozen times at fixed time intervals, for example intervals of 1 day, 2 days, 3 days, 4 days, 5 days, 6 days, 1 week, 2 weeks, 3 weeks, 1 month or the like. Alternatively, the pharmaceutical composition may be continually administered using a continual injection pomp as described above. When the pharmaceutical composition is continually administered, the dosage (rate), the period and the like can be appropriately set by those skilled in the art.

The subjects to be given the pharmaceutical composition are mammals such as primates (for example crab-eating monkeys, chimpanzees and humans) and nonprimates (for example cattle, pigs, sheep, horses, cats, dogs, guinea pigs, rats and mice), more preferably humans. The subject may be a subject having spinal cord injury.

The present invention also provides a method for treating a disease or a condition related to an increase in chondroitin sulfate, the method including administering to a subject in need thereof an antisense oligonucleotide according to an embodiment of the present invention, or a pharmaceutical composition.

The present invention also provides use of an antisense oligonucleotide according to an embodiment of the present invention in production of a pharmaceutical product for treating a disease or a condition related to an increase in chondroitin sulfate.

EXAMPLES

Hereinafter, the present invention will be described in further detail by way of Examples. However, the technical scope of the present invention is not limited to these Examples.

Example 1

(Design and Synthesis of Antisense Oligonucleotides)

Antisense oligonucleotides capable of suppressing expression of both of the CSGalNAcT1 gene and the CSGalNAcT2 gene were designed. A region having high homology was selected between human CSGalNAcT1 mRNA (SEQ ID NO: 164) and CSGalNAcT2 mRNA (SEQ ID NO: 165) by BLAST analysis. Subsequently, within this region, higher-structures were predicted with the mfold program (M. Zuker, Mfold web server for nucleic acid folding and hybridization prediction. Nucleic Acids Res. 31 (13), 3406-15, (2003)), or toxicity-developing sequences were excluded, and consequently, 107 types of nucleotide sequences were designed (Tables 1A, 1B and 1C). The sequences shown in Table 1A are sequences having no mismatch with part of human CSGalNAcT1 mRNA (these sequences are completely complementary to human CSGalNAcT1 mRNA), and 1 to 4 mismatches with part of human CSGalNAcT2 mRNA. The sequences shown in Table 1B are sequences having no mismatch with part of human CSGalNAcT1 mRNA, and no mismatch with part of human CSGalNAcT2 mRNA. The sequences shown in Table 1C are sequences having 1 to 4 mismatches with part of human CSGalNAcT1 mRNA, and no mismatch with part of human CSGalNAcT2 mRNA.

Next, without regard for homology between CSGalNAcT1 mRNA and CSGalNAcT2 mRNA, antisense oligonucleotides capable of suppressing expression of one of the CSGalNAcT1 gene or the CSGalNAcT2 gene were designed (Tables 1D and 1E). The sequences shown in Table 1D are sequences having no mismatch with part of human CSGalNAcT1 mRNA. The sequences shown in Table 1E are sequences having no mismatch with part of human CSGalNAcT2 mRNA.

The antisense oligonucleotides shown in Tables 1A to 1E were synthesized. GeneDesign, Inc. synthesized the antisense oligonucleotides to order. Each of the antisense oligonucleotides shown in Tables 1A to 1E was a gapmer 15 bases in length, which included a 5'-wing region including 3 LNA nucleotides, a DNA gap region including 9 deoxyribonucleosides, and a 3'-wing region including 2 LNA nucleosides and 1 deoxyribonucleoside at the 3'-end. The LNA nucleoside is a nucleoside having a sugar having a methyleneoxy (4'-$CH_2$—O-2') bridge. All the internucleoside bonds of the antisense oligonucleotides shown in Tables 1A to 1E were phosphorothioate bonds. The cytosine in the LNA nucleoside of each of the antisense oligonucleotides shown in Tables 1A to 1E was 5-methylcytosine.

TABLE 1A

Antisense oligonucleotides having nucleotide sequences having no mismatch with part of human CSGaINAcT1 mRNA, and 1 to 4 mismatches with part of human CSGaINAcT2 mRNA

| Name | Nucleotide sequence (5'→3') | SEQ ID NO: | Number of mismatch |
|---|---|---|---|
| hT1-1475-LNA(15) | TCTGTGGCCAGCTTG | 1 | 4 |
| hT1-1483-LNA(15) | CTGCATACTCTGTGC | 2 | 4 |
| hT1-1509-LNA(15) | TAGAGTAAAGCTATC | 3 | 4 |
| hT1-1547-LNA(15) | TGGCGGGTAACGCCA | 4 | 4 |
| hT1-1556-LNA(15) | TCCTCGGGGTGGCGG | 5 | 4 |
| hT1-1593-LNA(15) | CACCAACTCATCCCG | 6 | 2 |
| hT1-1595-LNA(15) | TCCACCAACTCATCC | 7 | 2 |
| hT1-1596-LNA(15) | TTCCACCAACTCATC | 5 | 1 |
| hT1-1597-LNA(15) | CTTCCACCAACTCAT | 9 | 1 |
| hT1-1603-LNA(15) | CAATGGCTTCCACCA | 10 | 1 |

TABLE 1A -continued

Antisense oligonucleotides having nucleotide sequences having no mismatch with part of human CSGaINAcT1 mRNA, and 1 to 4 mismatches with part of human CSGaINAcT2 mRNA

| Name | Nucleotide sequence (5'→3') | SEQ ID NO: | Number of mismatch |
|---|---|---|---|
| hT1-1613-LNA(15) | AAGGCTGATTCAATG | 11 | 4 |
| hT1-1614-LNA(15) | CAAGGCTGATTCAAT | 12 | 3 |
| hT1-1789-LNA(15) | GGCCGAATGGTCGAA | 13 | 4 |
| hT1-1800-LNA(15) | TTTCATGATGGGGCC | 14 | 3 |
| hT1-1801-LNA(15) | CTTTCATGATGGGGC | 15 | 3 |
| hT1-1302-LNA(15) | ACTTTCATGATGGGG | 16 | 3 |
| hT1-1803-LNA(15) | CACTTTCATGATGGG | 17 | 2 |
| hT1-1804-LNA(15) | TCACTTTCATGATGG | 18 | 2 |
| hT1-1807-LNA(15) | TTTTCACTTTCATGA | 19 | 1 |
| hT1-1865-LNA(15) | CTTTTTGCTAGAGGC | 20 | 4 |
| hT1-1959-LNA(15) | TTTCCCAAAGTAAAC | 21 | 3 |
| hT1-2125-LNA(15) | CATCACAGAAAAAGA | 22 | 1 |
| hT1-2141-LNA(15) | GTGAAGTAGATGTCC | 23 | 4 |
| hT1-2156-LNA(15) | TTGAGGAATTCAGAT | 24 | 3 |
| hT1-2158-LNA(15) | TATTGAGGAATTCAG | 25 | 3 |
| hT1-2210-LNA(15) | AAAAGAACTGGATAA | 26 | 4 |
| hT1-2227-LNA(15) | CAGGATTGTACTGAC | 27 | 2 |
| hT1-2228-LNA(15) | CCAGGATTGTACTGA | 23 | 3 |
| hT1-2278-LNA(15) | CCAGCTGCTGTTCCA | 29 | 1 |
| hT1-2279-LNA(15) | ACCASCTGCTGTTCC | 30 | 1 |
| hT1-2320-LNA(15) | CAAATCCAAAGTCTC | 31 | 2 |
| hT1-2321-LNA(15) | CCAAATCCAAAGTCT | 32 | 2 |
| hT1-2323-LNA(15) | TCCCLAATCCAAAGT | 33 | 3 |
| hT1-2324-LNA(15) | ATCCCAAATCCAAAG | 34 | 3 |
| hT1-2327-LNA(15) | GTCATCCCAAATCCA | 35 | 2 |
| hT1-2331-LNA(15) | ACACGTCATCCCAAA | 36 | 2 |
| hT1-2332-LNA(15) | GACACGTCATCCCAA | 37 | 2 |
| hT1-2337-LNA(15) | ATACTGACACGTCAT | 33 | 1 |
| hT1-2338-LNA(15) | GATACTGACACGTCA | 39 | 1 |
| hT1-2339-LNA(15) | CGATACTGACACGTC | 40 | 1 |
| hT1-2341-LNA(15) | ACCGATACTGACACG | 41 | 2 |
| hT1-2343-LNA(15) | TCACCCATACTGACA | 47 | 1 |
| hT1-2344-LNA(15) | CTGACCCATACTGAC | 43 | 1 |
| hT1-2345-LNA(15) | TCTGACCGATACTGA | 44 | 1 |
| hT1-2386-LNA(15) | AGCCTTTGATGTCCA | 45 | 4 |

TABLE 1A -continued

Antisense oligonucleotides having nucleotide sequences having no mismatch with part of human CSGaINAcT1 mRNA, and 1 to 4 mismatches with part of human CSGaINAcT2 mRNA

| Name | Nucleotide sequence (5'→3') | SEQ ID NO: | Number of mismatch |
|---|---|---|---|
| hT1-2446-LNA(15) | GTACCACTATGAGGT | 46 | 3 |
| hT1-2450-LNA(15) | GTCCGTACCACTATG | 47 | 3 |
| hT1-2549-LNA(15) | TTCATGGCCTTGGAC | 48 | 2 |

The number of mismatch is the number of mismatch with human CSGaINAcT2 mRNA.

TABLE 1B

Antisense oligonucleotides having nucleotide sequences having no mismatch with part of human CSGaINAcT1 mRNA, and no mismatch with part of human CSGaINAcT2 mRNA

| Name | Nucleotide sequence (5'→3') | SEQ ID NO: |
|---|---|---|
| hT1-2481-LNA(15) | ATGCCAGAGGTGGAA | 49 |
| hT1-2482-LNA(15) | CATGCCAGAGGTGGA | 50 |
| hT1-2483-LNA(15) | TCATGCCAGAGGTGG | 51 |
| hT1-2514-LNA(15) | CTCGGGGGTCAGCTC | 52 |
| hT1-2515-LNA(15) | GCTCGGGGGTCAGCT | 53 |
| hT1-2516-LNA(15) | TGCTCGGGGGTCAGC | 54 |
| hT1-2517-LNA(15) | CTGCTCGGGGGTCAG | 55 |
| hT1-2518-LNA(15) | ACTGCTCGGGGGTCA | 56 |
| hT1-2519-LNA(15) | TACTGCTCGGGGGTC | 57 |
| hT1-2520-LNA(15) | GTACTGCTCGGGGGT | 58 |

TABLE 1C

Antisense oligonucleotides having nucleotide sequences having I to 4 mismatches with part of human CSGaINAcT1 mRNA, and no mismatch with part of human CSGaINAcT2 mRNA

| Name | Nucleotide sequence (5'→3') | SEQ ID NO: | Number of mismatch |
|---|---|---|---|
| hT2-767-LNA(15) | TCACTCGGTAGTTTG | 59 | 4 |
| hT2-795-LNA(15) | CCCCATACTCACTGG | 60 | 4 |
| hT2-821-LNA(15) | TAAGGTAAAACTTTC | 51 | 4 |
| hT2-859-LNA(15) | TGGCGAGTGAGACCC | 62 | 4 |
| hT2-868-LNA(15) | TCTTCAGGATGGCGA | 63 | 4 |
| hT2-905-LNA(15) | CACCAATTCATCT(G | 64 | 2 |
| hT2-907-LNA(15) | TCCACCAATTCATCT | 65 | 2 |
| hT2-908-LNA(15) | TTCCACCAATTCATC | 66 | 1 |

TABLE 1C -continued

Antisense oligonucleotides having nucleotide sequences having I to 4 mismatches with part of human CSGaINAcT1 mRNA, and no mismatch with part of human CSGaINAcT2 mRNA

| Name | Nucleotide sequence (5'→3') | SEQ ID NO: | Number of mismatch |
|---|---|---|---|
| hT2-909-LNA(15) | CTTCCACCAATTCAT | 67 | 1 |
| hT2-915-LNA(15) | CAATAACTTCCACCA | 68 | 1 |
| hT2-925-LNA(15) | AAGCCCGCTTCAATA | 69 | 4 |
| hT2-926-LNA(15) | CAAGCCCGCTTCAAT | 70 | 2 |
| hT2-1128-LNA(15) | GTCCAAAAGGGCGGA | 71 | 4 |
| hT2-1139-LNA(15) | TTTCATGAGAGGTCC | 72 | 3 |
| hT2-1140-LNA(15) | CTTTCATGAGAGGTC | 73 | 3 |
| hT2-1141-TNA(15) | ACTTTCATGAGAGGT | 74 | 3 |
| hT2-1142-LNA(15) | CACTTTCATGAGAGG | 75 | 2 |
| hT2-1143-TNA(15) | TCACTTTCATGAGAG | 76 | 2 |
| hT2-1146-LNA(15) | TCITCACTTTCATGA | 77 | 1 |
| h12-1204-LNA(15) | CTTTCAGCAAGTGGC | 78 | 4 |
| hT2-1298-LNA(15) | TTTACCAAAATACAC | 79 | 2 |
| hT2-1464-LNA(15) | CATCACAGAAAAACA | 80 | 1 |
| hT2-146-LNA(15) | ACATCACAGAAAAAC | 81 | 1 |
| hT2-1480-LNA(15) | GAGAAATAGATATCA | 82 | 4 |
| hT2-1495-LNA(15) | TTAAGGAATTCGGCT | 83 | 3 |
| hT2-1497-LNA(15) | TGTTAAGGAATTCGG | 84 | 3 |
| hT2-1549-LNA(15) | AACACCACAGGGTAA | 85 | 4 |
| hT2-1366-LNA(15) | CAGGATTGTAAAGAC | 86 | 2 |
| hT2-1567-LNA(15) | GCAGGATTGTAAAGA | 87 | 2 |
| hT2-1617-LNA(15) | CCAGCTGCTGCTCCA | 88 | 1 |
| hT2-1618-LNA(15) | ACCAGCTGCTGCTCC | 89 | 1 |
| hT2-1653-LNA(15) | CAAAGCCAAAATCTC | 30 | 2 |
| hT2-1660-LNA(15) | CCAAAGCCAAAATCT | 91 | 2 |
| hT2-1662-LNA(15) | TTCCAAAGCCAAAAT | 92 | 3 |
| hT2-1663-LNA(15) | ATTCCAAAGCCAAAA | 93 | 3 |
| hT2-1666-LNA(15) | GTCATTCCAAAGCCA | 94 | 2 |
| hT2-1670-LNA(15) | ACAAGTCATTCCAAA | 95 | 2 |
| hT2-1671-LNA(15) | GACAAGTCATTCCAA | 96 | 2 |
| hT2-1676-TNA(15) | ATACTGACAAGTCAT | 97 | 1 |
| hT2-1677-LNA(15) | GATACTGACAAGTCA | 98 | 1 |
| hT2-1678-LNA(15) | CGATACTGACAAGTC | 99 | 1 |
| hT2-1680-LNA(15) | AACGATACTGACAAG | 100 | 2 |
| hT2-1682-LNA(15) | TGAACGATACTGACA | 101 | 1 |

TABLE 1C -continued

| Antisense oligonucleotides having nucleotide sequences having I to 4 mismatches with part of human CSGaINAcT1 mRNA, and no mismatch with part of human CSGaINAcT2 mRNA | | | |
|---|---|---|---|
| Name | Nucleotide sequence (5'→3') | SEQ ID NO: | Number of mismatch |
| hT2-1683-LNA(15) | CTGAACGATACTGAC | 102 | 1 |
| hT2-1684-TNA(15) | TCTGAACGATACTGA | 103 | 1 |
| hT2-1725-LNA(15) | AACCTTTCACTTCCA | 104 | 4 |
| hT2-1785-TNA(15) | GAATCACAATGAGGT | 105 | 3 |
| hT2-1789-LNA(15) | GTCCGAATCACAATG | 106 | 3 |
| hT2-1888-LNA(15) | TTCATCGCTTTAGAC | 107 | 2 |

The number of mismatch is the number of mismatch with human CSGaINAcT1 mRNA.

TABLE 1D

| Antisense oligonucleotides having nucleotide sequences having no mismatch with part of human CSGaINAcTI mRNA | | | |
|---|---|---|---|
| Name | Nucleotide sequence (5'→3') | SEQ ID NO: | Number of mismatch |
| hT1-1831-LNA(15) | TGTTGGCCATGTTGA | 108 | 8 |
| hT1-1847-LNA(15) | ATAACA7TGATAAGC | 109 | 5 |
| hT1-1971-LNA(15) | ATTTATTTCTTCTTT | 110 | 5 |
| hT1-1974-LNA(15) | TTCATTTATTTCTTC | 111 | 6 |
| hT1-1806-LNA(15) | TTTCACTTTCATGAT | 112 | 2 |
| hT1-2126-LNA(15) | ACATCACAGAAAAAG | 113 | 1 |
| hT1-2390-LNA(15) | CCCCAGCCTTTGATG | 114 | 4 |
| hT1-2479-LNA(15) | GCCAGAGGTCGAAGA | 115 | 1 |
| hT1-3716-LNA(15) | GCTTTATTTAAACAG | 116 | 15 |
| hT1-3717-LNA(15) | TGGTTTATTTAAACA | 117 | 15 |
| hT1-3719-LNA(15) | TTTCGTTTATTTAAA | 118 | 15 |
| hT1-3720-LNA(15) | CTTTCCTTTATTTAA | 119 | 15 |
| hT1-3723-LNA(15) | ATACTTTCGTTTATT | 120 | 15 |
| hT1-3745-LNA(15) | GAGATTGTTTGGTTC | 121 | 15 |
| hT1-3748-LNA(15) | AAAGAGATTGTTTGG | 122 | 15 |
| hT1-3751-LNA(15) | TGAAAAGAGATTGTT | 123 | 15 |
| hT1-3754-LNA(15) | TTTTGAAAAGAGATT | 124 | 15 |
| hT1-4197-LNA(15) | TTTCATAAACTACCA | 125 | 15 |
| hT1-4200-LNA(15) | AAATTTCATAAACTA | 126 | 15 |
| hT1-4203-LNA(15) | ATTAAATTTCATAAA | 127 | 15 |
| hT1-4206-LNA(15) | TTAATTAAATTTCAT | 128 | 15 |

TABLE 1D-continued

| Antisense oligonucleotides having nucleotide sequences having no mismatch with part of human CSGaINAcTI mRNA | | | |
|---|---|---|---|
| Name | Nucleotide sequence (5'→3') | SEQ ID NO: | Number of mismatch |
| hT1-4210-LNA(15) | TGTTTTAATTAAATT | 129 | 15 |
| hT1-4213-LNA(15) | CTGTGTTTTAATTAA | 130 | 15 |

The number of mismatch is the number of mismatch with human CSGaINAcT2 mRNA.

TABLE 1E

| Antisense oligonucleotides having nucleotide sequences having no mismatch with part of human CSGaINAcT2 mRNA | | | |
|---|---|---|---|
| Name | Nucleotide sequence (5'→3') | SEQ ID NO: | Number of mismatch |
| hT2-175-LNA(15) | TGTTACCATGATATC | 131 | 15 |
| hT2-173-LNA(15) | TATTGTTACCATGAT | 132 | 15 |
| hT2-222-LNA(15) | AGTCATGACTACTTG | 133 | 15 |
| hT2-420-LNA(15) | CAAGGCCCAACAGCA | 134 | 15 |
| hT2-524-LNA(15) | TTTACCATAATTTTC | 135 | 15 |
| hT2-630-LNA(15) | TCATTTCTTGTAATT | 136 | 15 |
| nT2-639-LNA(15) | TCTTCTCACTCATTT | 137 | 15 |
| hT2-735-LNA(15) | GAAGAAACTCTAAAA | 138 | 15 |
| hT2-813-LNA(15) | AACTTTCAAAGGGAA | 139 | 5 |
| hT2-872-LNA(15) | CTTTTCTTCAGGATG | 140 | 4 |
| hT2-891-LNA(15) | GTTTGTCTTTTCTAA | 141 | 4 |
| hT2-941-LNA(15) | ATTATTAATGACCTC | 142 | 6 |
| hT2-947-LNA(15) | ATCAGGATTATTAAT | 143 | 15 |
| hT2-1004-LNA(15) | ATTAAATATCACTTT | 144 | 15 |
| hT2-1113-LNA(15) | AGAGGGTCACATGTC | 145 | 15 |
| hT2-1183-DNA(15) | ATATTAATAATTGAT | 146 | 6 |
| hT2-1188-LNA(15) | CAATGATATTAATAA | 147 | 4 |
| hT2-1261-LNA(15) | TCTTGATGAATACAA | 148 | 5 |
| hT2-1372-LNA(15) | ACCAAGGTGTAATTG | 149 | 6 |
| hT2-1460-LNA(15) | ACAGAAAAACATCAA | 150 | 4 |
| hT2-1561-LNA(15) | TTGTAAAGACTGAAC | 151 | 3 |
| hT2-1750-LNA(15) | TAAAGATGAACATCT | 152 | 3 |
| hT2-1814-LNA(15) | GAGGTGGAAAAGACC | 153 | 2 |
| hT2-1893-LNA(15) | CCTCATTCATGGCTT | 154 | 2 |

The number of mismatch is the number of mismatch with human CSGaINAcT1 mRNA.

Subsequently, antisense oligonucleotides shown in Table 1F were synthesized. These antisense oligonucleotides have AmNA nucleosides. The nucleotide sequences of hT2-1617-AmNA(15), hT1-2519-AmNA(15), hT1-1831-AmNA(15) and hT1-2514-AmNA(15) were identical, respectively, to the nucleotide sequences of hT2-1617-LNA(15), hT1-2519-LNA(15), hT1-1831-LNA(15) and hT1-2514-LNA(15) shown in Tables 1A to 1E. GeneDesign, Inc. synthesized the antisense oligonucleotides to order. Each of the antisense oligonucleotides shown in Table 1F was a gapmer 15 bases in length, which included a 5'-wing region including 3 AmNA nucleotides, a DNA gap region including 9 deoxyribonucleosides, and a 3'-wing region including 2 AmNA nucleosides and 1 deoxyribonucleoside at the 3'-end. All the intemucleoside bonds of the antisense oligonucleotides shown in Table 1F were phosphorothioate bonds. The cytosine in the AmNA nucleoside of each of the antisense oligonucleotides shown in Table 1F was 5-methylcytosine. The AmNA nucleoside is a modified nucleoside having a sugar having a 4'-C(O)—N($CH_3$)-2' bridge.

TABLE 1F

Antisense oligonucleotide having AmNA nucleoside

| Name | Nucleotide sequence (5'→3') | SEQ ID NO: |
|---|---|---|
| hT2-1617-AmNA(15) | CCAGCTGCTGCTCCA | 155 |
| hT1-2519-AmNA(15) | TACTGCTCGGGGGTC | 156 |
| hT1-1831-AmNA(15) | TGTTGGCCATGTTGA | 157 |
| hT1-2514-AmNA(15) | CTCGGGGGTCAGCTC | 158 |

Subsequently, antisense oligonucleotides shown in Table 1G were synthesized. These antisense oligonucleotides target the mouse CSGalNAcT1 gene and the mouse CSGalNAcT2 gene. mT1-2120-LNA(15), mT1-2151-LNA(15), mT1-2156-LNA(15) and mT1-1915-LNA(15) have nucleotide sequences having no mismatch with mouse CSGalNAcT1 mRNA (SEQ ID NO: 166). mT2-1623-LNA(15) has a nucleotide sequence having no mismatch with mouse CSGalNAcT2 mRNA (SEQ ID NO: 167). The nucleotide sequence of mT1-2156-LNA(15) (SEQ ID NO: 161) is a nucleotide sequence derived from the nucleotide sequence of hT1-2519-LNA(15) (SEQ ID NO: 57) by substitution of one nucleic acid base. The nucleotide sequence of mT1-1915-LNA(15) (SEQ ID NO: 162) is a nucleotide sequence derived from the nucleotide sequence of hT1-2278-LNA (15) (SEQ ID NO: 29) by substitution of two nucleic acid bases. GeneDesign, Inc. synthesized the antisense oligonucleotides to order. Each of the antisense oligonucleotides shown in Table 1G was a gapmer 15 bases in length, which consisted of a 5'-wing region consisting of 3 LNA nucleotides, a DNA gap region consisting of 9 deoxyribonucleosides, and a 3'-wing region consisting of 2 LNA nucleosides and 1 deoxyribonucleoside at the 3'-end. All the internucleoside bonds of the antisense oligonucleotides shown in Table 1G were phosphorothioate bonds. The cytosine in the LNA nucleoside of each of the antisense oligonucleotides shown in Table 1G was 5-methylcytosine.

TABLE 1G

Antisense oligonucleotide targeting mouse CSGaINAcT1 gene and mouse CSGaINAcT2 gene

| Name | Nucleotide sequence (5'→3') | SEQ ID NO: |
|---|---|---|
| mT1-2120-LNA(15) | TCATGCCACAGGTGG | 159 |
| mT1-2151-LNA(15) | CTCAGGGGTCAGTTC | 160 |
| mT1-2156-LNA(15) | TACTGCTCAGGGGTC | 161 |
| mT1-1915-LNA(15) | CCAGCTGCTGTCCTA | 162 |
| mT2-1623-LNA(15) | CCAGCTGCTGCTCCA | 163 |

The name of each of the antisense oligonucleotides shown in Tables 1A to 1G indicates the position of a target region in human (h) or mouse (m) CSGalNAcT1 mRNA (T1) or CSGalNAcT2 mRNA (T2), the type of a modified nucleoside, and the number of bases in length. For example, hT1-1475-LNA(15) indicates that the antisense oligonucleotide targets a region starting with the 1475-position of human CSGalNAcT1 mRNA, contains a LNA nucleoside, and is 15 bases in length. For example, hT2-1617-AmNA (15) indicates that the antisense oligonucleotide targets a region starting with the 1617-position of human CSGalNAcT2 mRNA, contains an AmNA nucleoside, and is 15 bases in length.

Example 2

(Expression Suppressive Activity of Antisense Oligonucleotides in Human YKG-1 Cells)

Human YKG-1 cells were transfected with some of the antisense oligonucleotides synthesized in Example 1, and the amounts of CSGalNAcT1 mRNA and CSGalNAcT2 mRNA were determined to examine expression suppressive activity of the antisense oligonucleotides on the CSGalNAcT1 and the CSGalNAcT2 genes in human YKG-1 cells.

Human YKG-1 cells were obtained with cell registration No: JCRB0746 from National Institutes of Biomedical Innovation, Health and Nutrition, JCRB Cell Bank. The cells were thawed in the following manner. 9 mL of a DMEM medium (DMEM (low-glucose), nacalai tesque) supplied with 10% serum (fetal bovine serum, Biowest Company) and a 1% antibiotic substance (penicillin-streptomycin mixed solution (stabilized), nacalai tesque) was added to a 50 mL centrifuge tube. The cells melted by 80% at 37° C. were added to the centrifuge tube. The cells were centrifuged at 1000 rpm at room temperature for 2 minutes using a cooling centrifugal separator (VERSATILE REFRIGERATED CENTRIFUGE, TOMY SEIKO Co., Ltd.). The supernatant was removed by suction, the cells were resuspended in a new medium (DMEM medium supplied with 10% serum and a 1% antibiotic substance as described above), and 5 to $10\times10^5$ cells were seeded in a 10 cm dish (100 mm/tissue culturing dish, IWAKI & Co., Ltd.). The cells were cultured under a 5% $CO_2$ environment at 37° C.

One day after the cells were thawed as described above, the culture supernatant was removed by suction, and 10 mL of a new medium (DMEM medium supplied with 10% serum and a 1% antibiotic substance) was added to the cells to replace the medium.

Subculture of cells was performed in the following manner. The cells were subcultured when brought into a semiconfluent state. The culture medium was removed by suction from the 10 cm dish, the cells were washed with 4 mL of PBS, 2 mL of trypsin (0.25%-trypsin/1 mM-EDTA solution, nacalai tesque) was then added to the cells, and the cells were left standing under a 5% $CO_2$ environment at 37° C. for 3 minutes. 8 mL of a new medium (DMEM medium supplied with 10% serum and a 1% antibiotic substance) was added, and pipetting was then performed to transfer the cells into a 50 mL centrifuge tube. The cells were centrifuged at 1000 rpm at room temperature for 2 minutes. The supernatant was removed by suction, 5 to 10 mL of a new medium (DMEM medium supplied with 10% serum and a 1% antibiotic substance) was added, and the cells were resuspended. The cells were counted, and 2 to $7\times10^5$ cells were seeded in a new 10 cm dish. The cells were cultured under a 5% $CO_2$ environment at 37° C.

The cells to be transfected with the antisense oligonucleotides were seeded in the following manner. The culture medium was removed by suction from the 10 cm dish with cells reaching a semiconfluent state, the cells were washed with 4 mL of PBS, 2 mL of trypsin was then added to the cells, and the cells were left standing under a 5% $CO_2$ environment at 37° C. for 3 minutes. A DMEM medium supplied with 10% FBS was added, and pipetting was performed to transfer the cells into a 50 mL centrifuge tube. The cells were centrifuged at 1000 rpm at room temperature for 2 minutes, the supernatant was then removed by suction, 5 to 10 mL of a new DMEM medium supplied with 10% FBS was added, and the cells were resuspended. The cells were counted, and 12,500 cells (in 100 μL) per well were seeded in a 96-well plate (Corning® Costar®, 96-well multiple-well flat-bottom plate with a cap (low-evaporation)). The cells were cultured under a 5% $CO_2$ environment at 37° C. for 24 hours.

By a CEM method, the cells were transfected with the antisense oligonucleotides in the following manner. To a DMEM medium supplied with 10% FBS, 900 mM calcium chloride was added in such a manner that the calcium chloride was diluted by 100 times. In this way, a calcium chloride-containing medium was obtained. 5 μL of an antisense oligonucleotide with a predetermined concentration was mixed with 45 μL of the obtained calcium chloride-containing medium to obtain a nucleic acid solution. As the antisense oligonucleotides, antisense oligonucleotides shown in Tables 2A to 2E (corresponding to the antisense oligonucleotides shown in Tables 1A to 1E), of the antisense oligonucleotides synthesized in Example 1, were used. The culture medium in the 96-well plate was removed, the cells were washed with 120 μL of PBS, and the calcium chloride-containing medium was then added in an amount of 50 μL per well. Subsequently, 50 μL of the nucleic acid solution was added to the wells (final concentration of antisense oligonucleotide: 200 nM). The cells were cultured under a 5% $CO_2$ environment at 37° C. for 24 hours. As controls, cells transfected with nucleic acid NEG#L1 and untreated cells were prepared. The nucleic acid NEG#L1 has a nucleotide sequence of 5'-GAAAACTAAAATGAG-3' (SEQ ID NO: 186). The NEG#L1 was a gapmer 15 bases in length, which consisted of a 5'-wing region consisting of 3 LNA nucleotides, a DNA gap region consisting of 9 deoxyribonucleosides, and a 3'-wing region consisting of 2 LNA nucleosides and 1 deoxyribonucleoside at the 3'-end. All the internucleoside bonds of the NEG#L1 were phosphorothioate bonds.

From the cells, cDNA was prepared in the following manner. Using Super Prep™ Cell Lysis & RT Kit for qPCR (TOYOBO CO., LTD.), RNA was extracted from the transfected cells, and reverse-transcribed to cDNA. Specifically, the cells were cultured for 24 hours, the culture supernatant in the 96-well plate was then removed, 120 μL of PBS was added to the cells, and the PBS was removed. A mixed liquid of 24.85 μL of a lysis solution and 0.15 μL of a gDNA remover was added per well, and the cells were left standing for 5 minutes (stirred for the first 30 seconds). After 5 minutes, cell lysis was confirmed under a microscope, a mixed liquid of 4.75 μL of a stop solution and 0.25 μL of a RNase inhibitor was added per well, and the cells were left standing for 2 minutes (stirred for the first 30 seconds). After 2 minutes, the cell lysate was subjected to pipetting to add 6 μL of the cell lysate to a PCR plate (96 well PCR Plate (Non-Skirted), VIOLAMO Company) containing a mixed liquid of 4 μL of a SXRT master mix and 10 μL of nuclease-free water. The plate was covered with a cap (8 strips PCR Tube Cap (Dome), VIOLAMO Company), and centrifugation was performed at 3200 rpm at 4° C. for 2 minutes. The PCR plate was set in a thermal cycler (ABI Veriti® 96 well Thermal Cycler, Thermo Fisher Scientific), and reverse transcription reaction was carried out (37° C. for 20 minutes, 50° C. for 5 minutes, 90° C. for 5 minutes, and 4° C.). The cDNA obtained by reverse transcription reaction, and the cell plate were stored at −80° C.

Using the cDNA, real-time PCR (RT-PCR) was carried out in the following manner. 2×10 μL of a master mix (ABI™ Fast SYBR™ Green Master Mix, Thermo Fisher Scientific), 1 μL of a primer set, 2 μL of the cDNA and 7 μL (gross volume: 20 μL) of Otsuka distilled water (Otsuka Pharmaceutical Factory, Inc.) were mixed, and the resulting mixture was dispensed to a real-time PCR 96-well plate (ABI, MicroAmp® Fast 96-well Reaction Plate (0.1 mL), Thermo Fisher Scientific).

The following primer sets were used. The primers were obtained from Thermo Fisher Scientific.

```
Control primer set:
50 nM hGAPDH-F
(5'-GAGTCAACGGATTTGGTCGT-3', SEQ ID NO: 170)
and

50 nM hGAPDH-R
(5'-GACAAGCTTCCCGTTCTCAG-3', SEQ ID: 171)

hCSGalNAcT1 set 1:
100 nM hT1-F1
(5'-TCAGGGAGATGTGCATTGAG-3', SEQ ID NO: 172)
and

100 nM hT1-R1
(5'-AGTTGGCAGCTTTGGAAGTG-3', SEQ ID NO: 173)

hCSGalNAcT1 set 2:
200 nM hT1-F2
(5'-GGAGACCCTGAACAGTCCTG-3', SEQ ID NO: 174)
and

200 nM hT1-R2
(5'-GCCGTTTGAATTCGTGTTTG-3', SEQ ID NO: 175)

hCSGalNAcT2 set 1:
200 nM hT2-F1
(5'-GCCATTGTTTATGCCAACCA-3', SEQ ID NO: 176)
and

200 nM hT2-R1
(5'-ATCCACCAATGGTCAGGAAA-3', SEQ ID NO: 177)
```

-continued

```
hCSGalNAcT2 set 2:
200 nM hT2-F2
(5'-TCCTAGAATCTGTCACCAGTGAG-3', SEQ ID NO: 178)
and

200 nM hT2-R2
(5'-ACATCAAGACCTCTCCCTTGTC-3', SEQ ID NO: 179)
```

The concentration of the primer shows a concentration in the PCR reaction solution (20 μL).

The control primer set is a primer set for the human GAPDH (glyceraldehyde-3-phosphate dehydrogenase) gene (housekeeping gene). The hCSGalNAcT1 set 1 and the hCSGalNAcT1 set 2 are primer sets for the human hCSGalNAcT1 gene. The hCSGalNAcT2 set 1 and the hCSGalNAcT2 set 2 are primer sets for the human hCSGalNAcT2 gene. One of the following primer sets was used in the PCR reaction solution: control primer set (for measurement of human GAPDH); hCSGalNAcT1 set 1 or hCSGalNAcT1 set 2 (for measurement of human CSGalNAcT1); and hCSGalNAcT2 set 1 or hCSGalNAcT2 set 2 (for measurement of human CSGalNAcT2).

The PCR plate was sealed (ABI, MicroAmp™ Optical Adhesive Film, Thermo Fisher Scientific). The PCR plate was centrifuged at 3200 rpm and at 4° C. for 2 minutes. The PCR plate was set in a thermal cycler (ABI StepOne Plus™ Real-Time PCR System, Thermo Fisher Scientific), and real-time PCR was performed under the temperature condition of 95° C. for 30 seconds, followed by 45 cycles of 95° C. for 3 seconds and 60° C. for 30 seconds.

The relative amount of human CSGalNAcT1 mRNA and the relative amount of human CSGalNAcT2 mRNA were calculated using a ΔΔCt method. Specifically, ΔCt was calculated by subtracting the Ct value of GAPDH from the threshold cycle (Ct) value of human CSGalNAcT1 or human CSGalNAcT2 measured with cells transfected with an antisense oligonucleotide. Further, ΔΔCt was calculated by subtracting similarly calculated ΔCt of untreated cells from the threshold cycle (Ct) value. The relative amounts of human CSGalNAcT1 mRNA and human CSGalNAcT2 mRNA were calculated from $2^{-\Delta\Delta Ct}$, respectively. Two PCR reaction solutions were prepared for each sample, and an average value and a standard deviation of the relative amounts were calculated for the respective samples.

The results are shown in FIG. 1 and Tables 2A to 2E. FIG. 1 is a plot diagram of the relative amounts of CSGalNAcT1 mRNA and the relative amounts of CSGalNAcT2 mRNA shown in Tables 2A to 2E. Further, the relative amount of CSGalNAcT1 mRNA and the relative amount of CSGalNAcT2 mRNA in the case of transfecting the cells with control nucleic acid NEG#L1 were 0.893 and 0.973, respectively. The relative amount of CSGalNAcT1 mRNA and the relative amount of CSGalNAcT2 mRNA decrease as expression suppressive activity of the antisense oligonucleotide on the CSGalNAcT1 and the CSGalNAcT2 genes increases.

TABLE 2A

| Relative amounts of human CSGalNAcT1 mRNA and human CSGalNAcT2 mRNA | | | |
|---|---|---|---|
| Name | T1 | T2 | SEQ ID NO: |
| hT1-1475-LNA(15) | 0.008 | 0.099 | 1 |
| hT1-1483-LNA(15) | 0.029 | 1.144 | 2 |
| hT1-1509-LNA(15) | 0.027 | 1.022 | 3 |
| hT1-1556-LNA(15) | 0.018 | 2.842 | 5 |
| hT1-1593-LNA(15) | 0.049 | 1.198 | 6 |

TABLE 2A-continued

| Relative amounts of human CSGalNAcT1 mRNA and human CSGalNAcT2 mRNA | | | |
|---|---|---|---|
| Name | T1 | T2 | SEQ ID NO: |
| hT1-1595-LNA(15) | 0.143 | 0.718 | 7 |
| hT1-1596-LNA(15) | 0.385 | 1.109 | 8 |
| hT1-1597-LNA(15) | 0.004 | 0.111 | 9 |
| hT1-1603-LNA(15) | 0.009 | 1.217 | 10 |
| hT1-1613-LNA(15) | 0.000 | 1.347 | 11 |
| hT1-1614-LNA(15) | 0.019 | 1.562 | 12 |
| hT1-1789-LNA(15) | 0.073 | 0.942 | 13 |
| hT1-1800-LNA(15) | 0.002 | 1.209 | 14 |
| hT1-1801-LNA(15) | 0.008 | 0.840 | 15 |
| hT1-1802-LNA(15) | 0.015 | 0.294 | 16 |
| hT1-1803-LNA(15) | 0.036 | 0.803 | 17 |
| hT1-1804-LNA(15) | 0.011 | 0.170 | 18 |
| hT1-1807-LNA(15) | 0.042 | 0.305 | 19 |
| hT1-1865-LNA(15) | 0.005 | 0.333 | 20 |
| hT1-1959-LNA(15) | 0.062 | 0.166 | 21 |
| hT1-2125-LNA(15) | 0.234 | 0.157 | 22 |
| hT1-2141-LNA(15) | 0.006 | 0.198 | 23 |
| hT1-2156-LNA(15) | 0.032 | 0.127 | 24 |
| hT1-2158-LNA(15) | 0.123 | 0.161 | 25 |
| hT1-2210-LNA(15) | 0.245 | 0.191 | 26 |
| hT1-2227-LNA(15) | 0.009 | 0.174 | 27 |
| hT1-2228-LNA(15) | 0.001 | 0.222 | 28 |
| hT1-2278-LNA(15) | 0.232 | 0.095 | 29 |
| hT1-2279-LNA(15) | 0.242 | 0.168 | 30 |
| hT1-2320-LNA(15) | 0.634 | 1.322 | 31 |
| hT1-2321-LNA(15) | 0.221 | 1.115 | 32 |
| hT1-2323-LNA(15) | 0.456 | 1.119 | 33 |
| hT1-2324-LNA(15) | 0.578 | 1.289 | 34 |
| hT1-2327-LNA(15) | 0.053 | 0.090 | 35 |
| hT1-2331-LNA(15) | 0.105 | 0.914 | 36 |
| hT1-2332-LNA(15) | 0.068 | 0.290 | 37 |
| hT1-2337-LNA(15) | 0.181 | 0.506 | 38 |
| hT1-2338-LNA(15) | 0.291 | 0.275 | 39 |
| hT1-2339-LNA(15) | 0.109 | 0.197 | 40 |
| hT1-2341-LNA(15) | 0.147 | 0.865 | 41 |
| hT1-2343-LNA(15) | 0.118 | 0.709 | 42 |
| hT1-2344-LNA(15) | 0.110 | 0.370 | 43 |
| hT1-2345-LNA(15) | 0.075 | 0.439 | 44 |
| hT1-2386-LNA(15) | 0.036 | 0.827 | 45 |
| hT1-2446-LNA(15) | 0.076 | 0.698 | 46 |
| hT1-2450-LNA(15) | 0.016 | 1.054 | 47 |
| hT1-2549-LNA(15) | 0.043 | 0.358 | 48 |

TABLE 2B

| Relative amounts of human CSGalNAcT1 mRNA and human CSGalNAcT2 mRNA | | | |
|---|---|---|---|
| Name | T1 | T2 | SEQ ID NO: |
| hT1-2481-LNA(15) | 0.100 | 0.069 | 49 |
| hT1-2482-LNA(15) | 0.046 | 0.051 | 50 |
| hT1-2483-LNA(15) | 0.027 | 0.031 | 51 |
| hT1-2514-LNA(15) | 0.027 | 0.119 | 52 |
| hT1-2515-LNA(15) | 0.215 | 0.391 | 53 |
| hT1-2516-LNA(15) | 0.120 | 0.227 | 54 |
| hT1-2517-LNA(15) | 0.249 | 0.180 | 55 |
| hT1-2518-LNA(15) | 0.226 | 0.624 | 56 |
| hT1-2519-LNA(15) | 0.100 | 0.112 | 57 |
| hT1-2520-LNA(15) | 0.069 | 0.043 | 58 |

TABLE 2C

| Relative amounts of human CSGalNAcT1 mRNA and human CSGalNAcT2 mRNA | | | |
|---|---|---|---|
| Name | T1 | T2 | SEQ ID NO: |
| hT2-787-LNA(15) | 0.123 | 0.010 | 59 |
| hT2-795-LNA(15) | 1.127 | 0.062 | 60 |

TABLE 2C-continued

| Relative amounts of human CSGalNAcT1 mRNA and human CSGalNAcT2 mRNA | | | |
|---|---|---|---|
| Name | T1 | T2 | SEQ ID NO: |
| hT2-821-LNA(15) | 1.204 | 0.498 | 61 |
| hT2-859-LNA(15) | 0.280 | 0.017 | 62 |
| hT2-868-LNA(15) | 0.079 | 0.024 | 63 |
| hT2-905-LNA(15) | 1.180 | 0.024 | 64 |
| hT2-907-LNA(15) | 0.847 | 0.139 | 65 |
| hT2-908-LNA(15) | 0.895 | 0.373 | 66 |
| hT2-909-LNA(15) | 0.258 | 0.041 | 67 |
| hT2-915-LNA(15) | 0.748 | 0.106 | 68 |
| hT2-925-LNA(15) | 0.630 | 0.032 | 69 |
| hT2-926-LNA(15) | 0.714 | 0.035 | 70 |
| hT2-1128-LNA(15) | 0.851 | 0.049 | 71 |
| hT2-1139-LNA(15) | 1.137 | 0.007 | 72 |
| hT2-1140-LNA(15) | 1.117 | 0.014 | 73 |
| hT2-1141-LNA(15) | 0.721 | 0.011 | 74 |
| hT2-1142-LNA(15) | 1.140 | 0.021 | 75 |
| hT2-1143-LNA(15) | 0.941 | 0.186 | 76 |
| hT2-1146-LNA(15) | 1.306 | 0.188 | 77 |
| hT2-1204-LNA(15) | 0.512 | 0.003 | 78 |
| hT2-1298-LNA(15) | 0.865 | 0.221 | 79 |
| hT2-1464-LNA(15) | 0.769 | 0.819 | 80 |
| hT2-1465-LNA(15) | 0.310 | 0.797 | 81 |
| hT2-1480-LNA(15) | 1.135 | 0.125 | 82 |
| hT2-1495-LNA(15) | 1.066 | 0.008 | 83 |
| hT2-1497-LNA(15) | 1.913 | 0.012 | 84 |
| hT2-1549-LNA(15) | 1.113 | 0.048 | 85 |
| hT2-1566-LNA(15) | 0.769 | 0.062 | 86 |
| hT2-1567-LNA(15) | 0.704 | 0.114 | 87 |
| hT2-1617-LNA(15) | 0.017 | 0.175 | 88 |
| hT2-1618-LNA(15) | 0.074 | 0.221 | 89 |
| hT2-1659-LNA(15) | 0.428 | 0.156 | 90 |
| hT2-1660-LNA(15) | 0.523 | 0.159 | 91 |
| hT2-1662-LNA(15) | 0.681 | 0.535 | 92 |
| hT2-1663-LNA(15) | 0.762 | 0.470 | 93 |
| hT2-1666-LNA(15) | 1.413 | 0.030 | 94 |
| hT2-1670-LNA(15) | 1.233 | 0.147 | 95 |
| hT2-1671-LNA(15) | 1.538 | 0.058 | 96 |
| hT2-1676-LNA(15) | 1.171 | 0.240 | 97 |
| hT2-1677-LNA(15) | 1.255 | 0.092 | 98 |
| hT2-1678-LNA(15) | 0.857 | 0.088 | 99 |
| hT2-1680-LNA(15) | 0.718 | 0.161 | 100 |
| hT2-1682-LNA(15) | 1.369 | 0.053 | 101 |
| hT2-1683-LNA(15) | 0.289 | 0.063 | 102 |
| hT2-1684-LNA(15) | 1.056 | 0.147 | 103 |
| hT2-1725-LNA(15) | 1.092 | 0.119 | 104 |
| hT2-1785-LNA(15) | 1.109 | 0.119 | 105 |
| hT2-1789-LNA(15) | 0.788 | 0.118 | 106 |
| hT2-1888-LNA(15) | 0.057 | 0.060 | 107 |

TABLE 2D

| Relative amounts of human CSGalNAcT1 mRNA and human CSGalNAcT2 mRNA | | | |
|---|---|---|---|
| Name | T1 | T2 | SEQ ID NO: |
| hT1-1831-LNA(15) | 0.003 | 0.847 | 108 |
| hT1-1847-LNA(15) | 0.799 | 1.049 | 109 |
| hT1-1971-LNA(15) | 0.636 | 0.975 | 110 |
| hT1-1974-LNA(15) | 0.248 | 1.068 | 111 |
| hT1-2479-LNA(15) | 0.210 | 0.521 | 115 |
| hT1-3716-LNA(15) | 0.520 | 1.027 | 116 |
| hT1-3720-LNA(15) | 0.775 | 0.914 | 119 |
| hT1-3723-LNA(15) | 0.724 | 1.023 | 120 |
| hT1-3745-LNA(15) | 0.103 | 0.985 | 121 |
| hT1-3748-LNA(15) | 0.292 | 1.049 | 122 |
| hT1-3751-LNA(15) | 0.798 | 1.123 | 123 |
| hT1-4197-LNA(15) | 0.332 | 1.104 | 125 |

TABLE 2E

| Relative amounts of human CSGalNAcT1 mRNA and human CSGalNAcT2 mRNA | | | |
|---|---|---|---|
| Name | T1 | T2 | SEQ ID NO: |
| hT2-175-LNA(15) | 0.763 | 0.047 | 131 |
| hT2-178-LNA(15) | 0.881 | 0.044 | 132 |
| hT2-222-LNA(15) | 0.850 | 0.104 | 133 |
| hT2-420-LNA(15) | 1.073 | 0.178 | 134 |
| hT2-524-LNA(15) | 1.052 | 0.564 | 135 |
| hT2-630-LNA(15) | 0.318 | 0.288 | 136 |
| hT2-639-LNA(15) | 1.015 | 0.298 | 137 |
| hT2-813-LNA(15) | 0.910 | 0.302 | 139 |
| hT2-872-LNA(15) | 1.218 | 0.122 | 140 |
| hT2-891-LNA(15) | 1.140 | 0.140 | 141 |
| hT2-941-LNA(15) | 0.650 | 0.181 | 142 |
| hT2-947-LNA(15) | 0.742 | 0.461 | 143 |
| hT2-1004-LNA(15) | 0.112 | 0.163 | 144 |
| hT2-1113-LNA(15) | 0.757 | 0.047 | 145 |
| hT2-1261-LNA(15) | 0.822 | 0.496 | 148 |
| hT2-1372-LNA(15) | 0.759 | 0.191 | 149 |
| hT2-1460-LNA(15) | 0.504 | 0.535 | 150 |
| hT2-1561-LNA(15) | 0.969 | 0.672 | 151 |
| hT2-1814-LNA(15) | 0.935 | 0.746 | 153 |
| hT2-1893-LNA(15) | 0.400 | 0.281 | 154 |

The antisense oligonucleotides synthesized in Example 1 were shown to suppress expression of one or both of the human CSGalNAcT1 gene and the human CSGalNAcT2 gene (Tables 2A to 2E). In particular, all of the antisense oligonucleotides having nucleotide sequence having no mismatch with human CSGalNAcT1 mRNA and having no mismatch with human CSGalNAcT2 mRNA were shown to significantly suppress expression of both of the human CSGalNAcT1 gene and the human CSGalNAcT2 gene (black circle in FIG. 1 and Table 2B).

Example 3

(Concentration-Dependent Expression Suppressive Activity of Antisense Oligonucleotides in Mouse 3T3N Cells)

Mouse 3T3N cells were transfected at various concentrations with some of the antisense oligonucleotides synthesized in Example 1, and the amounts of CSGalNAcT1 mRNA and CSGalNAcT2 mRNA were determined to examine concentration-dependent expression suppressive activity of the antisense oligonucleotides on the CSGalNAcT1 and the CSGalNAcT2 genes in mouse 3T3N cells.

Mouse 3T3N cells were obtained with cell registration No: JCRB0615 from National Institutes of Biomedical Innovation, Health and Nutrition, JCRB Cell Bank. In the manner described in Example 2, the cells were thawed, and media were replaced.

Subculture of cells was performed in the following manner. The cells were subcultured when brought into a semi-confluent state. The culture medium was removed by suction from the 10 cm dish, the cells were washed with 4 mL of PBS, 2 mL of 0.125% trypsin (prepared by diluting 0.25%-trypsin/1 mM-EDTA solution (nacalai tesque) with PBS by two times) was then added to the cells, and the cells were left standing under a 5% $CO_2$ environment at 37° C. for 1 minute. 8 mL of a new medium (DMEM medium supplied with 10% serum and a 1% antibiotic substance as described in Example 2) was added, and pipetting was then performed to transfer the cells into a 50 mL centrifuge tube. The cells were centrifuged at 1000 rpm at room temperature for 2 minutes. The supernatant was removed by suction, 5 to 10 mL of a new medium (DMEM medium supplied with 10% serum and a 1% antibiotic substance as described in Example 2) was added, and the cells were resuspended. The cells were counted, and 1 to $5\times10^5$ cells were seeded in a new 10 cm dish. The cells were cultured under a 5% $CO_2$ environment at 37° C.

The cells to be transfected with the antisense oligonucleotides were seeded in the following manner. The culture medium was removed by suction from the 10 cm dish with cells reaching a semiconfluent state, the cells were washed with 4 mL of PBS, 2 mL of 0.125% trypsin was then added to the cells, and the cells were left standing under a 5% $CO_2$ environment at 37° C. for 1 minute. A DMEM medium supplied with 10% FBS was added, and pipetting was performed to transfer the cells into a 50 mL centrifuge tube. The cells were centrifuged at 1000 rpm at room temperature for 2 minutes, the supernatant was then removed by suction, 5 mL of a new DMEM medium supplied with 10% FBS was added, and the cells were resuspended. The cells were counted, and 15,000 cells (in 100 μL) per well were seeded in a 96-well plate (Corning® Costar®, 96-well multiple-well flat-bottom plate with a cap (low-evaporation)). The cells were cultured under a 5% $CO_2$ environment at 37° C. for 24 hours.

By using a CEM method and a lipofection in combination, the cells were transfected with the antisense oligonucleotides in the following manner. To a DMEM medium supplied with 10% FBS, 900 mM calcium chloride was added in such a manner that the calcium chloride was diluted by 100 times. In this way, a calcium chloride-containing medium was obtained. Lipofectamine (Lipofectamine® 3000 Transfection Kit, Thermo Fisher Scientific) was added to the obtained calcium chloride-containing medium in such a manner that the lipofectamine was diluted by 91 times. In this way, a lipofectamine solution was obtained. 5 μL of an antisense oligonucleotide with a predetermined concentration was mixed with 45 μL of the obtained lipofectamine solution to obtain a nucleic acid solution. As the antisense oligonucleotides, hT1-2514-LNA(15), hT2-1617-AmNA (15), hT1-1831-LNA(15), hT1-2126-LNA(15), hT2-420-LNA(15), hT2-872-LNA(15) and hT2-891-LNA(15), of the nucleic acid synthesized in Example 1, were used. The culture medium in the 96-well plate was removed, the cells were washed with 120 μL of PBS, and the calcium chloride-containing medium was then added in an amount of 50 μL per well. Subsequently, 50 μL of the nucleic acid solution was added to the wells (final concentration of antisense oligonucleotide: 30, 60, 120 or 240 nM). The cells were cultured under a 5% $CO_2$ environment at 37° C. for 24 hours. As controls, cells transfected with nucleic acid NEG#L1 and untreated cells were prepared.

Subsequently, cDNA was prepared from the cells in the manner described in Example 2.

Real-time PCR (PT-PCR) was carried out using the cDNA. The real-time PCR was carried out in the same manner as described in Example 2 except that the following primer sets were used, and a temperature condition of 95° C. for 30 seconds, followed by 45 cycles of 95° C. for 3 seconds and 62° C. for 30 seconds was employed.

```
Control primer set:
200 nM mGAPDH-F
(5'-TGCACCACCAACTGCTTAG-3', SEQ ID NO: 180)
and

200 nM mGAPDH-R
(5'-GATGCAGGGATGATGTTC-3', SEQ ID NO: 181)
```

-continued

```
mCSGalNAcT1 set:
200 nM mT1-F1
(5'- CCAATTTCAGAAACTTCACCTTCAT-3',
SEQ ID NO: 182)
and

200 nM mT1-R1
(5'-TGTTCAGCCTACAAGTGTTGAG-3', SEQ ID NO: 183)

mCSGalNAcT2 set:
200 nMmT2-F1
(5'-TTAATATCATTGTGCCACTTGCG-3', SEQ ID NO: 184)
and

200 nM mT2-R1
(5'-TAGAATAGACTTGACTTTAGATAGTCCTT-3',
SEQ ID NO: 185)
```

The control primer set is a primer set for the mouse GAPDH (glyceraldehyde-3-phosphate dehydrogenase) gene (housekeeping gene). The mCSGalNAcT1 is a primer set for the mouse CSGalNAcT1 gene. The mCSGalNAcT2 set is a primer set for the mouse CSGalNAcT2 gene. One of the following three primer sets was used in the PCR reaction solution: control primer set (for measurement of mouse GAPDH); mCSGalNAcT1 set (for measurement of mouse CSGalNAcT1); and mCSGalNAcT2 set (for measurement of mouse CSGalNAcT2).

The relative amounts of mouse CSGalNAcT1 mRNA and mouse CSGalNAcT2 mRNA in cells transfected with the antisense oligonucleotides to those of CSGalNAcT1 mRNA and mouse CSGalNAcT2 mRNA in untreated cells were calculated by the ΔΔCt method using the Ct value obtained by the real-time PCR.

FIG. 2A shows the relative amounts of mouse CSGalNAcT1 mRNA in mouse 3T3N cells transfected with the antisense oligonucleotides. FIG. 2B shows the relative amounts of mouse CSGalNAcT2 mRNA in mouse 3T3N cells transfected with the antisense oligonucleotides. The tested antisense oligonucleotides (hT1-2514-LNA(15), hT2-1617-AmNA(15), hT1-1831-LNA(15), hT1-2126-LNA (15), hT2-420-LNA(15), hT2-872-LNA(15) and hT2-891-LNA(15)) were showed to tend to suppress expression of both of the mouse CSGalNAcT1 gene and the mouse CSGalNAcT2 gene in a concentration-dependent manner.

Example 4

(Concentration-Dependent Expression Suppressive Activity of Antisense Oligonucleotides in Human SKOV-3 Cells)

Human SKOV-3 cells were transfected with some of the antisense oligonucleotides synthesized in Example 1, and the amounts of CSGalNAcT1 mRNA and CSGalNAcT2 mRNA were determined to examine expression suppressive activity of the antisense oligonucleotides on the CSGalNAcT1 and the CSGalNAcT2 genes in human SKOV-3 cells.

Human SKOV-3 cells were obtained with catalog No: EC91091004-F0 from Summit Pharmaceuticals International Corporation. The cells were thawed in the following manner. 9 mL of a McCoy's 5A medium (GIBCO Company) supplied with 10% serum (fetal bovine serum, Biowest Company) and a 1% antibiotic substance (penicillin-streptomycin mixed solution (stabilized), nacalai tesque) was added to a 50 mL centrifuge tube. The cells melted by 80% at 37° C. were added to the centrifuge tube. The cells were centrifuged at 1000 rpm at room temperature for 3 minutes using a cooling centrifugal separator (VERSATILE REFRIGERATED CENTRIFUGE, TOMY SEIKO Co., Ltd.). The supernatant was removed by suction, the cells were resuspended in a new medium (McCoy's 5A medium supplied with 10% serum and a 1% antibiotic substance), and 3 to $10\times10^5$ cells were seeded in a 10 cm dish (100 mm/tissue culturing dish, IWAKI & Co., Ltd.). The cells were cultured under a 5% $CO_2$ environment at 37° C.

One day after the cells were thawed as described above, the culture supernatant was removed by suction, and 10 mL of a new medium (McCoy's 5A medium supplied with 10% serum and a 1% antibiotic substance) was added to the cells to replace the medium.

Subculture of cells was performed in the following manner. The cells were subcultured when brought into a semiconfluent state. The culture medium was removed by suction from the 10 cm dish, the cells were washed with 4 mL of PBS, 2 mL of trypsin (0.25%-trypsin/1 mM-EDTA solution, nacalai tesque) was then added to the cells, and the cells were left standing under a 5% $CO_2$ environment at 37° C. for 1 minute. 8 mL of a new medium (McCoy's 5A medium supplied with 10% serum and a 1% antibiotic substance) was added, and pipetting was then performed to transfer the cells into a 50 mL centrifuge tube. The cells were centrifuged at 1000 rpm at room temperature for 3 minutes. The supernatant was removed by suction, 5 to 10 mL of a new medium (McCoy's 5A medium supplied with 10% serum and a 1% antibiotic substance) was added, and the cells were resuspended. The cells were counted, and 2 to $7\times10^5$ cells were seeded in a new 10 cm dish. The cells were cultured under a 5% $CO_2$ environment at 37° C.

The cells to be transfected with the antisense oligonucleotides were seeded in the following manner. The culture medium was removed by suction from the 10 cm dish with cells reaching a semiconfluent state, the cells were washed with PBS, 2 mL of trypsin was then added to the cells, and the cells were left standing under a 5% $CO_2$ environment at 37° C. for 1 minute. A McCoy's 5A medium supplied with 10% FBS was added, and pipetting was performed to transfer the cells into a 50 mL centrifuge tube. The cells were centrifuged at 1000 rpm at room temperature for 3 minutes, the supernatant was then removed by suction, 5 to 10 mL of a new McCoy's 5A medium supplied with 10% FBS was added, and the cells were resuspended. The cells were counted, and 20,000 cells (in 500 μL) per well were seeded in a 24-well plate (24-well cell culturing microplate, IWAKI & Co., Ltd.). The cells were cultured under a 5% $CO_2$ environment at 37° C. for 24 hours.

By a CEM method, the cells were transfected with the antisense oligonucleotides in the following manner. To a McCoy's 5A medium supplied with 10% FBS, 900 mM calcium chloride was added in such a manner that the calcium chloride was diluted by 100 times. In this way, a calcium chloride-containing medium was obtained. 25 μL of an antisense oligonucleotide with a predetermined concentration was mixed with 225 μL of the obtained calcium chloride-containing medium to obtain a nucleic acid solution. As the antisense oligonucleotides, hT1-2514-LNA(15), hT1-2519-AmNA(15) and hT2-1617-AmNA(15), of the nucleic acids synthesized in Example 1, were used. The culture medium in the 24-well plate was removed, the cells were washed with 600 μL of PBS, and the calcium chloride-containing medium was then added in an amount of 250 μL per well. Subsequently, 250 μL of the nucleic acid solution was added to the wells (final concentration of antisense oligonucleotide: 100 or 200 nM). The cells were cultured under a 5% $CO_2$ environment at 37° C. for 24 hours. As controls, cells transfected with nucleic acid NEG#L1 and untreated cells were prepared.

From the cells, cDNA was prepared in the following manner. First, RNA was extracted using QIAGEN RNeasy® Mini Kit. Specifically, transfected cells were washed with 600 μL of PBS, 200 μL of trypsin was then added, and the cells were left standing under a 5% $CO_2$ environment at 37° C. for 3 minutes. 400 μL of a McCoy's 5A medium supplied with 10% FBS was added to the cells, and pipetting was then performed to collect the cells in a new 1.5 mL tube. 500 μL of a new McCoy's 5A medium supplied with 10% FBS was added to the wells, and pipetting was then performed to collect the cells in the tube. The tube was centrifuged at 1000 rpm at room temperature for 3 minutes (centrifuge 5430R, Eppendolf AG). The supernatant was removed, and 1 mL of PBS was added to the tube. The tube was centrifuged at 1000 rpm at room temperature for 3 minutes. The supernatant was removed. 20 μL of 2 M DTT was added to 980 μL of a RLT buffer was added, the resulting mixture was thoroughly mixed to obtain a mixed liquid, and 350 μL of the mixed liquid was added to the tube, and vortexed. 70% ethanol was added to the tube in an amount of equal to the amount of the mixed liquid, and pipetting was performed slowly. A spin column was put in a 2 mL collection tube, 700 μL of the solution in the tube was added into the spin column. The spin column was centrifuged at 10000 rpm at room temperature for 15 seconds, and the filtrate was discarded. 700 μL of a RW1 buffer was added into the spin column. The spin column was centrifuged at 10000 rpm at room temperature for 15 seconds, and the filtrate was discarded. 500 μL of a RPE buffer was added into the spin column. The spin column was centrifuged at 10000 rpm at room temperature for 15 seconds, and the filtrate was discarded. 500 μL of a RPE buffer was added into the spin column. The spin column was centrifuged at 10000 rpm at room temperature for 15 seconds, and the filtrate was discarded. The spin column was set in a new 2 mL collection tube. The spin column was centrifuges at 13200 rpm at room temperature for 1 minute, and the filtrate was discarded. The spin column was set in a new 1.5 mL collection tube. RNase-free water was added into a 36 μL spin column. The spin column was centrifuged at 10000 rpm at room temperature for 1 minute to elute RNA. The column was removed, and the 1.5 mL tube was transferred onto ice. 2 μL of the RNA eluate was used for spectrometry (DS-11 Spectrophotometer, DeNOVIX Inc.). Next, RNA was reverse-transcribed to cDNA using ABI High-Capacity cDNA Reverse Transcription Kit (Thermo Fisher Scientific). Specifically, 10×4 μL of an RT buffer, 1.6 μL of 100 mM dNTPs, 10×4 μL of a RT Ramdom™ primer, 2 μL of a MultiScribe™ reverse transcriptase (50 U/μL) and 28 μL of a RNA solution (containing 4 μg of RNA and subjected to volume adjustment with nuclease-free water) (total volume: 39.6 μL) were added into a new 0.5 mL tube. The tube was set in a thermal cycler (WK-0518, Wako Pure Chemical Industries, Ltd.). Reverse transcription reaction was carried out under the temperature condition of 25° C. for 10 minutes, 37° C. for 120 minutes, 85° C. for 5 minutes and 4° C. to obtain cDNA. The cDNA was stored at −80° C.

Real-time PCR (RT-PCR) was carried out using the cDNA. The real-time PCR was carried out in the same manner as described in Example 2 except for the primer concentrations and the master mix. The primer concentration was set to 200 nM for hGAPDH-F and hGAPDH-R, and 400 nM for hT1-F1, hT1-R1, hT1-F2, hT1-R2, hT2-F1, hT2-R1, hT2-F2 and hT2-R2. As the master mix, ABI™ PowerUp™ SYBR® Green Master Mix (Thermo Fisher Scientific) was used.

The relative amounts of human CSGalNAcT1 mRNA and human CSGalNAcT2 mRNA in cells transfected with the antisense oligonucleotides to those of human CSGalNAcT1 mRNA and human CSGalNAcT2 mRNA in untreated cells were calculated by the ΔΔCt method using the Ct value obtained by the real-time PCR.

FIG. 3A shows the relative amounts of human CSGalNAcT1 mRNA in human SKOV-3 cells transfected with hT1-2514-LNA(15) and hT1-2519-AmNA(15). FIG. 3B shows the relative amounts of human CSGalNAcT2 mRNA in human SKOV-3 cells transfected with hT1-2514-LNA (15) and hT1-2519-AmNA(15). FIG. 4A shows the relative amounts of human CSGalNAcT1 mRNA in human SKOV-3 cells transfected with hT2-1617-AmNA(15). FIG. 4B shows the relative amounts of human CSGalNAcT2 mRNA in human SKOV-3 cells transfected with hT2-1617-AmNA (15). The tested antisense oligonucleotides (hT1-2514-LNA (15), hT1-2519-AmNA(15) and hT2-1617-AmNA(15)) were shown to tend to suppress expression of both of the human CSGalNAcT1 gene and the human CSGalNAcT2 gene in a concentration-dependent manner.

Example 5

(Expression Suppressive Activity of Antisense Oligonucleotides in Human U251 Cells)

Human U251 cells were transfected with some of the antisense oligonucleotides synthesized in Example 1, and the amounts of CSGalNAcT1 mRNA and CSGalNAcT2 mRNA were determined to examine expression suppressive activity of the antisense oligonucleotides on the CSGalNAcT1 and the CSGalNAcT2 genes in human U251 cells.

Human YKG-1 cells were obtained with cell registration No: IFO50288 from National Institutes of Biomedical Innovation, Health and Nutrition, JCRB Cell Bank. The cells were thawed in the following manner. 9 mL of a DMEM medium (DMEM (low-glucose), nacalai tesque) supplied with 10% serum (fetal bovine serum, Biowest Company) and a 1% antibiotic substance (penicillin-streptomycin mixed solution (stabilized), nacalai tesque) was added to a 50 mL centrifuge tube. The cells melted by 80% at 37° C. were added to the centrifuge tube. The cells were centrifuged at 1000 rpm at room temperature for 3 minutes using a cooling centrifugal separator (VERSATILE REFRIGERATED CENTRIFUGE, TOMY SEIKO Co., Ltd.). The supernatant was removed by suction, the cells were resuspended in a new medium (DMEM medium supplied with 10% serum and a 1% antibiotic substance), and 3 to $10\times10^5$ cells were seeded in a 10 cm dish (100 mm/tissue culturing dish, IWAKI & Co., Ltd.). The cells were cultured under a 5% $CO_2$ environment at 37° C.

One day after the cells were thawed as described above, the culture supernatant was removed by suction, and 10 mL of a new medium (DMEM medium supplied with 10% serum and a 1% antibiotic substance) was added to the cells to replace the medium.

Subculture of cells was performed in the following manner. The cells were subcultured when brought into a semiconfluent state. The culture medium was removed by suction from the 10 cm dish, the cells were washed with 4 mL of PBS, 2 mL of trypsin (0.25%-trypsin/1 mM-EDTA solution, nacalai tesque) was then added to the cells, and the cells were left standing under a 5% $CO_2$ environment at 37° C. for 1 minute. 8 mL of a new medium (DMEM medium supplied with 10% serum and a 1% antibiotic substance) was added, and pipetting was then performed to transfer the cells into a 50 mL centrifuge tube. The cells were centrifuged at 1000 rpm at room temperature for 3 minutes. The supernatant was removed by suction, 5 to 10 mL of a new medium (DMEM medium supplied with 10% serum and a 1% antibiotic substance) was added, and the cells were resuspended. The cells were counted, and 3 to $7\times10^5$ cells were seeded in a new 10 cm dish. The cells were cultured under a 5% $CO_2$ environment at 37° C.

The cells to be transfected with the antisense oligonucleotides were seeded in the following manner. The culture medium was removed by suction from the 10 cm dish with cells reaching a semiconfluent state, the cells were washed with 4 mL of PBS, 2 mL of trypsin was then added to the cells, and the cells were left standing under a 5% $CO_2$ environment at 37° C. for 1 minute. A DMEM medium supplied with 10% FBS was added, and pipetting was performed to transfer the cells into a 50 mL centrifuge tube. The cells were centrifuged at 1000 rpm at room temperature for 3 minutes, the supernatant was then removed by suction, 5 to 10 mL of a new DMEM medium supplied with 10% FBS was added, and the cells were resuspended. The cells were counted, and 30,000 cells (in 500 μL) per well were seeded in a 24-well plate (24-well cell culturing microplate, IWAKI & Co., Ltd.). The cells were cultured under a 5% $CO_2$ environment at 37° C. for 24 hours.

By using a CEM method and a lipofection in combination, the cells were transfected with the antisense oligonucleotides in the following manner. To a DMEM medium supplied with 10% FBS, 900 mM calcium chloride was added in such a manner that the calcium chloride was diluted by 100 times. In this way, a calcium chloride-containing medium was obtained. Lipofectamine (Lipofectamine® 3000 Transfection Kit, Thermo Fisher Scientific) was added to the obtained calcium chloride-containing medium in such a manner that the lipofectamine was diluted by 91 times. In this way, a lipofectamine solution was obtained. 25 μL of an antisense oligonucleotide with a predetermined concentration was mixed with 225 μL of the obtained lipofectamine solution to obtain a nucleic acid solution. As the antisense oligonucleotides, mT1-1915-LNA(15), hT1-1831-LNA (15), hT1-2126-LNA(15), mT1-2156-LNA(15), hT1-2327-LNA(15), hT1-2479-LNA(15), hT1-2514-LNA(15), hT2-420-LNA(15), hT2-872-LNA(15), hT2-891-LNA(15), hT2-1617-AmNA(15), hT2-1839-LNA(15), hT1-2519-AmNA (15) and hT1-2519-LNA(15), of the nucleic acids synthesized in Example 1 were used. The culture medium in the 24-well plate was removed, the cells were washed with 600 μL of PBS, and the calcium chloride-containing medium was then added in an amount of 250 μL per well. Subsequently, 250 μL of the nucleic acid solution was added to the wells (final concentration of antisense oligonucleotide: 200 nM). The cells were cultured under a 5% $CO_2$ environment at 37° C. for 24 hours. As controls, cells transfected with nucleic acid NEG#L1 and untreated cells were prepared.

By the same method as described in Example 4, cDNA was prepared from the cells, and real-time PCR was carried out. The relative amounts of human CSGalNAcT1 mRNA and human CSGalNAcT2 mRNA in cells transfected with the antisense oligonucleotides to those of human CSGalNAcT1 mRNA and human CSGalNAcT2 mRNA in untreated cells were calculated by the M Ct method using the Ct value obtained by the real-time PCR.

FIG. 5A shows the relative amounts of human CSGalNAcT1 mRNA in human U251 cells transfected with the antisense oligonucleotides. FIG. 5B shows the relative amounts of human CSGalNAcT2 mRNA in human U251 cells transfected with the antisense oligonucleotides. The tested antisense oligonucleotides (mT1-1915-LNA(15), hT1-1831-LNA(15), hT1-2126-LNA(15), mT1-2156-LNA (15), hT1-2327-LNA(15), hT1-2479-LNA(15), hT1-2514-LNA(15), hT2-420-LNA(15), hT2-872-LNA(15), hT2-891-LNA(15), hT2-1617-AmNA(15), hT2-1839-LNA(15), hT1-2519-AmNA(15) and hT1-2519-LNA(15)) were shown to suppress expression of both of the human CSGalNAcT1 gene and the human CSGalNAcT2 gene.

Example 6

(Concentration-Dependent Expression Suppressive Activity of Antisense Oligonucleotides in Human U251 Cells)

Human U251 cells were transfected with some of the antisense oligonucleotides synthesized in Example 1, and the amounts of CSGalNAcT1 mRNA and CSGalNAcT2 mRNA were determined to examine concentration-dependent expression suppressive activity of the antisense oligonucleotides on the CSGalNAcT1 and the CSGalNAcT2 genes in human U251 cells.

In the same manner as described in Example 5 except for the concentrations and types of antisense oligonucleotides with which cells were transfected, human U251 cells were transfected with the antisense oligonucleotides, cDNA was prepared from the cells, and real-time PCR was carried out. The relative amounts of human CSGalNAcT1 mRNA and human CSGalNAcT2 mRNA in cells transfected with the antisense oligonucleotides to those of human CSGalNAcT1 mRNA and human CSGalNAcT2 mRNA in untreated cells were calculated by the ΔΔCt method using the Ct value obtained by the real-time PCR. The final concentration of the antisense oligonucleotide which the cells were transfected was 50, 100 or 200 nM. As the antisense oligonucleotides, hT1-2126-LNA(15), hT1-2327-LNA(15), hT1-2514-LNA(15), hT2-891-LNA(15), hT2-1617-AmNA(15), hT2-1839-LNA(15) and hT1-2519-LNA(15), of the nucleic acids synthesized in Example 1 were used.

FIG. 6A shows the relative amounts of human CSGalNAcT1 mRNA in human U251 cells transfected with the antisense oligonucleotides. FIG. 6B shows the relative amounts of human CSGalNAcT2 mRNA in human U251 cells transfected with the antisense oligonucleotides. The tested antisense oligonucleotides (hT1-2126-LNA(15), hT1-2327-LNA(15), hT1-2514-LNA(15), hT2-891-LNA(15), hT2-1617-AmNA(15), hT2-1839-LNA(15) and hT1-2519-LNA(15)) were shown to tend to suppress expression of both of the human CSGalNAcT1 gene and the human CSGalNAcT2 gene.

Example 7

(Effect of Antisense Oligonucleotides on the Amounts of Chondroitin Sulfate and Heparan Sulfate)

Human YKG-1 cells and human U251 cells were transfected with some of the antisense oligonucleotides synthesized in Example 1, and the amounts of chondroitin sulfate and heparan sulfate in the cells were determined by the In Cell ELISA assay to examine the effects of the antisense oligonucleotides on the amounts of chondroitin sulfate and heparan sulfate.

YKG-1 cells (derived from human glioblast) and U251 cells (derived from human astrocytoma, obtained with catalog No: EC09063001-F0 from Summit Pharmaceuticals International Corporation) were cultured in a 10 cm-dish until reaching a 80%-confluent state. By a method similar to the combination of a CEM method and a lipofection method as described in Example 5, a calcium chloride solution was added to a medium, and using lipofectamine (Lipofectamine® 3000 Transfection Kit, Thermo Fisher Scientific), YKG-1 cells and U251 cells were transfected with antisense oligonucleotides at a final concentration of 100 nM. As the antisense oligonucleotides, hT1-1804-LNA(15), hT1-2514-LNA(15), hT1-2519-LNA(15), hT2-1617-LNA (15), hT1-2126-LNA(15), hT2-891-LNA(15), hT2-941-LNA(15) and hT2-1893-LNA(15) were used. As controls, cells transfected with nucleic acid NEG#L1 and untreated cells were prepared.

The cells were released 68 hours after transfection using trypsin, and suspended in 4 mL of a medium. The cells were partially stained with trypan blue (Gibco Company), and the number of living cells was counted using a disposable hemocytometer C-Chip. The cells were seeded in a 96-well cell culture plate (BD Falcon Company, product No: 353072) in such a manner that the number of cells per well was $1\times10^4$ (in 200 μl). For each type of cells, cells were seeded in 24 to 32 wells. The cells were cultured under a 5% $CO_2$ environment at 37° C. for 1 day.

PBST (0.05% Tween 20 in PBS) was prepared by adding 20 μl of Tween 20 to 1×40 mL of PBS (in 50 mL conical tube). The cells were cultured, 200 μl (per well) of PBST was then added to the wells, the PBST was immediately removed, and this operation was performed once again. Subsequently, 200 μl (per well) of PBST was added to the wells, and after 5 minutes, the cells were washed. The washing was performed twice more.

100 μl (per well) of 4% PFA/PBS was added to the wells, and incubation was performed at room temperature for 20 minutes to fix the cells. The 4% PFA/PBS was prepared in the following manner. 0.48 g of PFA (paraformaldehyde powder, nacalai tesque, code No: 26126-25) was added into the 15 mL conical tube, 9 mL of sterilized water and 2.9 μl of 4 N NaOH were then added to the tube, and a cap of the tube was hermetically sealed with paraffin. The tube was immersed in hot water, and vigorously stirred to dissolve PFA. The tube was placed on ice, 1.2 mL of 10×PBS was added, and the solution was then diluted to 12 mL with sterilized water to obtain 4% PFA/PBS. The 4% PFA/PBS was stored while being shielded from light (storable for 1 week).

200 μl (per well) of PBST was added to the wells, the PBST was immediately removed, and this operation was performed once again. Subsequently, 200 μl (per well) of PBST was added to the wells, and after 5 minutes, the cells were washed. The washing was performed twice more.

200 μl (per well) of 3% BSA/PBS was added to the wells, and incubation was performed at room temperature for 1 hour to block the cells. The 3% BSA/PBS was prepared by adding 0.6 g of BSA (albumin (derived from bovine serum), Cohn Fraction (pH 7.0), Wako Pure Chemical Industries, Ltd., catalog No: 017-23294) to 1×20 mL of PBS (in 50 mL conical tube), and dissolving the BSA. The 3% BSA/PBS was stored at 4° C.

200 μl (per well) of PBST was added to the wells, and after 5 minutes, the cells were washed. The washing was performed twice more.

100 μl (per well) of a solution of a primary antibody (chondroitin sulfate detecting antibody or heparan sulfate detecting antibody) was added to the wells, or 100 μl (per well) of 3% BSA/PBS was added to the wells as a negative control (antibody(−)), and incubation was performed at 4° C. overnight, or at room temperature for 1 to 2 hours. For ensuring that the plate was not dried during the incubation, the plate was hermetically sealed with a parafilm, and put in a tight box, and KimWipes wetted with MQ water (ultrapure water) was placed in the box. As a primary antibody for detecting chondroitin sulfate, a mouse anti-chondroitin sulfate (CS) antibody (CS-56) (1.9 mg/mL, Abcam Company, catalog No: ab11570) was used. As a primary antibody for detecting heparan sulfate, an anti-heparan sulfate antibody 3G10 (Seikagaku Corporation) was used. The primary antibodies were diluted with 100 μl of 3% BSA/PBS by 1,000 times (per well) at the time of use.

After the incubation with the primary antibody, 200 μl (per well) of PBST was added to the wells, the PBST was immediately removed, and this operation was performed once again. Subsequently, 200 μl (per well) of PBST was added to the wells, and after 5 minutes, the cells were washed. The washing was performed twice more.

100 μl (per well) of a secondary antibody solution was added to the wells, and incubation was performed for 1 hour. For ensuring that the plate was not dried during the incubation, the plate was put in a tight box, and KimWipes wetted with MQ water was placed in the box. Further, during the incubation, the plate was shielded from light. As a secondary antibody, goat anti-mouse IgG+IgM (H+L)-AP (1 mg/mL, human absorbed, KPL, Inc., catalog No: 751-1809) was used. The secondary antibody was diluted with 100 μl of 3% BSA/PBS by 2,000 times (per well) at the time of use.

200 μl of TBST was added to each of the wells, and after 5 minutes, the cells were washed. The washing was performed twice more. Subsequently, 200 μl of TBS was added to each of the wells, and after 5 minutes, the cells were washed. The washing was performed twice more.

A pNPP solution was prepared in the following manner. A 2× pNPP buffer (0.1 M carbonate buffer solution (pH 9.8), 1 mM $MgCl_2$) was prepared using a 0.2 M carbonate buffer solution (pH 9.8) prepared using sodium carbonate and sodium hydrogen carbonate, and 0.5 M $MgCl_2.6H_2O$. p-Nitrophenyl phosphate disodium salt hexahydrate (pNPP) (Wako Pure Chemical Industries, Ltd., code No: 147-02343) was dissolved in MQ water at a concentration of 40 mg/mL. At the time of use, 0.5 mL of 40 mg/mL pNPP, 5 mL of the 2×pNPP buffer and 4.5 mL of MQ water were mixed to prepare 10 mL of the pNPP solution (50 wells of the pNPP solution). 200 μl (per well) of the pNPP solution was added to the cells, and after 30 minutes, the absorbance was measured by iMark™ Plate Reader (Bio-Rad Laboratories, Inc.) using an excitation wavelength of 405 nm. Alkali phosphatase bonded to the secondary antibody converts p-nitrophenylphosphate into p-nitrophenol. In the method, the absorbance of the product: p-nitrophenol was measured.

The relative amount of chondroitin sulfate or heparin sulfate was expressed as a ratio of the absorbance at 405 nm to the absorbance in untreated control cells. For each group, the experiment was conducted twice, and an average value was calculated.

FIG. 7A shows the relative amounts of chondroitin sulfate and heparan sulfate in YKG-1 cells transfected with the antisense oligonucleotides. FIG. 7B shows the relative amounts of chondroitin sulfate and heparan sulfate in U251 cells transfected with the antisense oligonucleotides.

The antisense oligonucleotides hT1-1804-LNA(15), hT1-2514-LNA(15), hT1-2519-LNA(15), hT2-1617-LNA(15), hT1-2126-LNA(15), hT2-891-LNA(15), hT2-941-LNA(15) and hT2-1893-LNA(15) were shown to tend to reduce the amount of chondroitin sulfate. However, these antisense oligonucleotides hardly reduced the amount of heparan sulfate. This showed that these antisense oligonucleotides specifically reduced the amount of chondroitin sulfate.

Further, the antisense oligonucleotides which had markedly reduced the amount of chondroitin sulfate (for example, hT1-2514-LNA(15), hT1-2519-LNA(15) and hT2-1617-LNA(15)) increased the amount of heparan sulfate on the contrary, and this result is consistent with the previous report that there was an increase in expression of a heparan sulfate synthetase at affected sites of spinal cord injury model mice treated with siRNA against CSGalNAcT1 (Takeuchi, K., et al., 2013, described above).

Example 8

(Effects of Antisense Oligonucleotides on the Amount of Heparan Sulfate)

The antisense oligonucleotide (hT1-2126-LNA(15)) synthesized in Example 1 was introduced into C6 cells (derived from rat glioma) and U251 cells (derived from human astrocytoma), and the amount of heparan sulfate in the cells was determined by the In Cell ELISA assay to examine the effects of the antisense oligonucleotides on the amount of heparan sulfate.

The C6 cells (derived from rat glioma) were obtained with cell registration No: JCRB9096 from National Institutes of Biomedical Innovation, Health and Nutrition, JCRB Cell Bank. By the same method as described in Example 6, the C6 cells or U251 cells were transfected with the antisense oligonucleotide (hT1-2126-LNA(15)), and the absorbance of p-nitrophenol (405 nm) was measured by the In Cell ELISA assay using a primary antibody for detecting heparan sulfate. As a control, the absorbance of p-nitrophenol (405 nm) was similarly measured in untreated cells by the In Cell ELISA assay. Further, the cells were treated with xyloside, and the absorbance of p-nitrophenol (405 nm) was similarly measured by the In Cell ELISA assay. For each group, the experiment was conducted five times, and an average value and a standard error were calculated.

The xyloside was obtained from Sigma-Aldrich, Inc. The xyloside treatment was performed at 50 μM for 24 hours. Xyloside is known to reduce the amount of heparan sulfate in cells.

Figure 8:
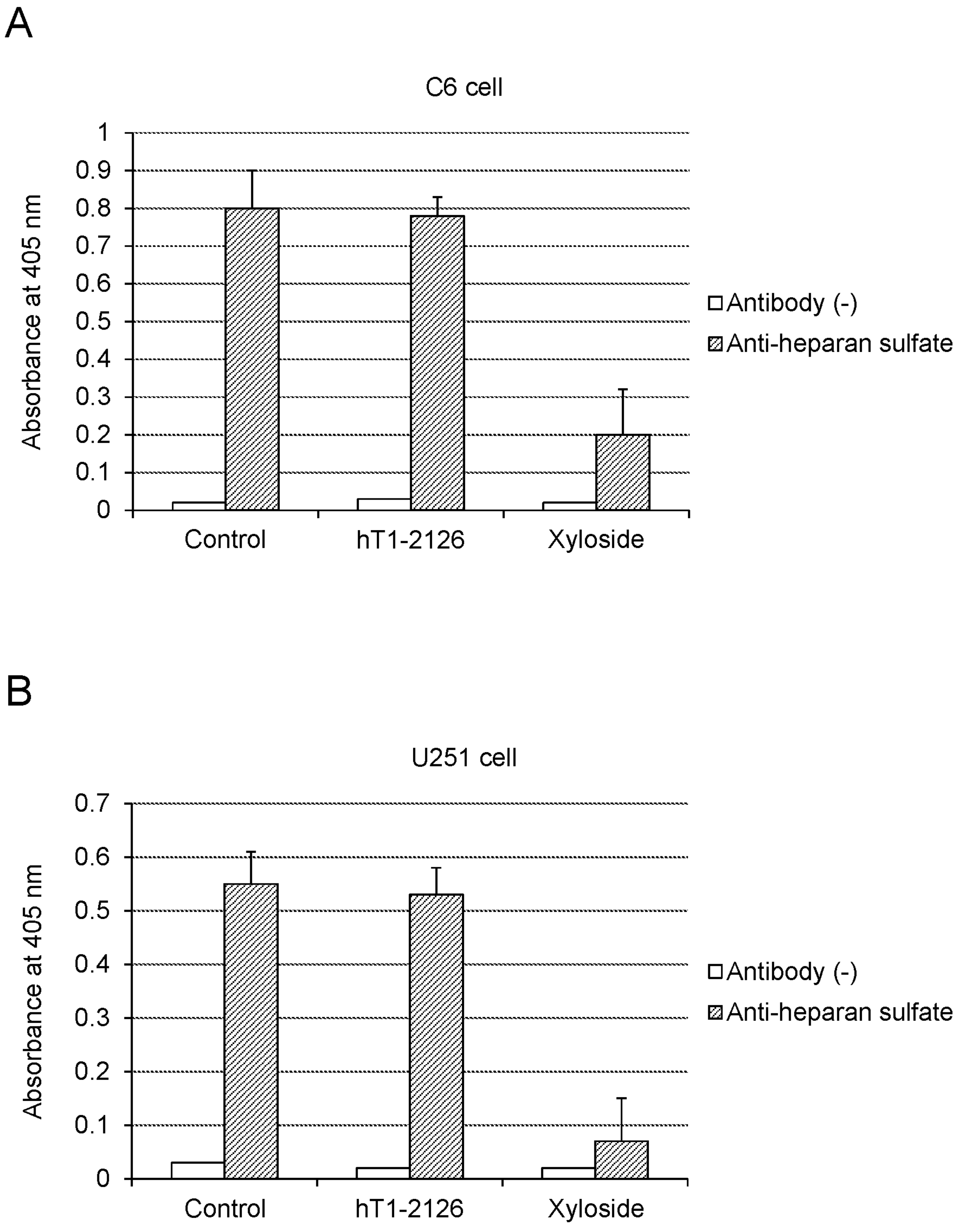
FIG. 8 is a graph showing the effects of antisense oligonucleotides on the amount of heparan sulfate.

FIG. 8A shows absorbances (405 nm) in rat C6 cells. FIG. 8B shows absorbances (405 nm) in human U251 cells. The absorbance is correlated with the amount of heparan sulfate. It was confirmed that the amount of heparan sulfate was reduced by the xyloside treatment in comparison with the control.

It was shown that in rat C6 cells and human U251 cells, transfection with the antisense oligonucleotide (hT1-2126-LNA(15)) had little effect on the amount of heparan sulfate.

Example 9

(Effects of Antisense Oligonucleotides on Scar Formation)

The amount of in vitro scar formation was determined to examine the effects of the antisense oligonucleotides on scar formation. The present inventors developed an in vitro scar formation system in which fibrous scars are formed by mixing fibroblasts and glia cells, and culturing the resulting mixture in a medium containing growth factors (TGFβ and PDGF). Scars formed as a result of restoration of tissues after injury of the spinal cord are generally considered to inhibit regeneration of nerves. Thus, recovery from spinal cord injury can be promoted by suppressing formation of the scars.

U251 cells (glia cells, derived from human astrocytoma) were obtained with cell registration No: IFO50288 from National Institutes of Biomedical Innovation, Health and Nutrition, JCRB Cell Bank. HT1080 cells (fibroblasts, derived from human fibrosarcoma) were obtained with cell registration No: JCRB9113 from National Institutes of Biomedical Innovation, Health and Nutrition, JCRB Cell Bank.

$5\times10^4$ U251 cells and $5\times10^4$ HT1080 cells were suspended and mixed in 50 μl of a medium (RPMI1640 medium, Wako Pure Chemical Industries, Ltd.). The cell mixed liquid was seeded in a 96-well flat-bottom dish (PLL-coated, Nunc Company), and cultured in a RPMI1640 medium supplied with 15% FCS (Hyclone Laboratories, Inc.).

On the following day, the medium was replaced by a medium supplied with TGFβ and PDGF (RPMI1640 medium supplied with 5% FCS (Hyclone Laboratories, Inc.), 10 ng/ml TGFβ and 5 ng/ml PDGF (prepared at the time of use). As the TGFβ (transforming growth factor β), TGF-β1 (human, recombinant, produced in HEK293 cells) available with product code: 100-21 from Funakoshi Co., Ltd., or LAP/TGF-β1 (human, recombinant, produced in Sf21 cells) available with product code: 246-LP-025 from Funakoshi Co., Ltd. was used. As the PDGF (growth factor derived from platelet), PDGF-B (human, recombinant) available with code No: 166-19743 or PDGF-AA (human, recombinant) available with code No: 169-19733 from Wako Pure Chemical Industries, Ltd., or PDGF-BB (recombinant human platelet-derived growth factor BB) available with product No: NIB 47083000 from Oriental Yeast Co., Ltd. was used.

In replacement of the medium, by a method similar to the combination of a CEM method and a lipofection method as described in Example 5, a calcium chloride solution was added to a medium, and using lipofectamine (Lipofectamine® 3000 Transfection Kit, Thermo Fisher Scientific), the cells were transfected with the antisense oligonucleotides at a final concentration of 100 nM. As the antisense oligonucleotides, hT1-2327-LNA(15), hT1-2514-LNA(15), hT1-2519-LNA(15), hT2-1617-LNA(15), hT1-2126-LNA(15), hT2-891-LNA(15) and hT2-1893-LNA(15) synthesized in Example 1 were used. As controls, cells transfected with nucleic acid NEG#L1 and untreated cells were prepared.

The cells were incubated in a $CO_2$ incubator at 37° C.

Using a living cell analysis system IncuCyte® (Essen Bioscience K.K.), the number of scars and the scar area (total area) were measured in accordance with the maker's manual 72 hours after administration of the antisense oligonucleotide. The scar area was expressed as the number of image pixels. The experiment was conducted twice, and average values of the numbers of scars and the scar areas (total areas) were calculated.

The present inventors have confirmed that when LY-36497 (inhibitor against action of TGFβ, Sigma-Aldrich) is used, scar formation is reduced.

Figure 9:
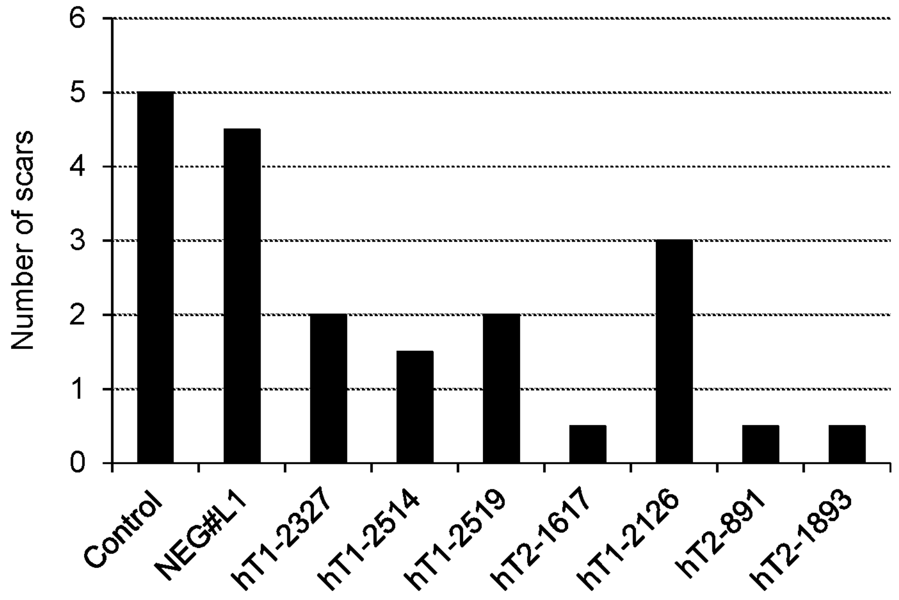
FIG. 9 is a graph showing the effects of antisense oligonucleotides on scar formation.
Figure 9:
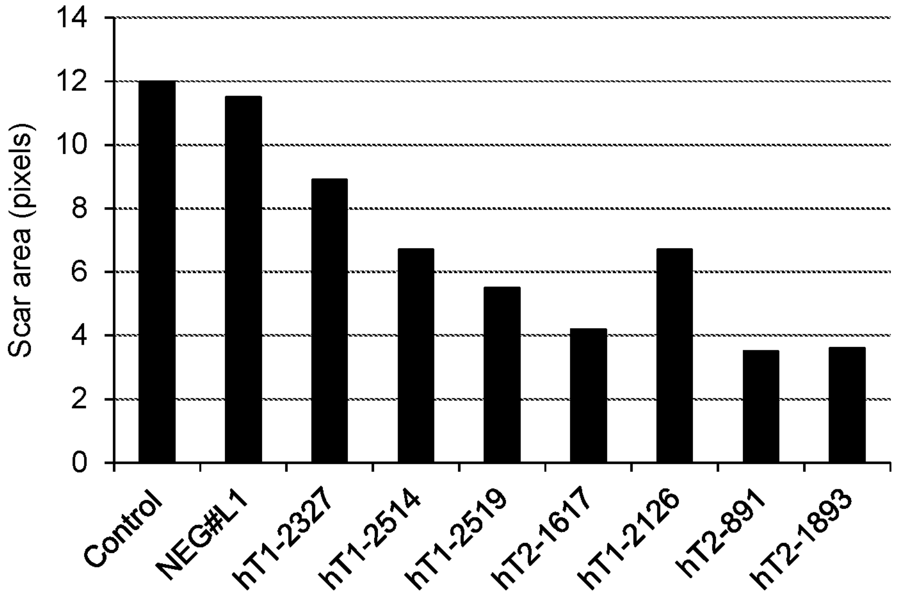

FIG. 9A shows the numbers of scars in the cells transfected with the antisense oligonucleotides. FIG. 9B shows the scar areas in the cells transfected with the antisense oligonucleotides. The antisense oligonucleotides hT1-2327-LNA(15), hT1-2514-LNA(15), hT1-2519-LNA(15), hT2-1617-LNA(15), hT1-2126-LNA(15), hT2-891-LNA(15) and hT2-1893-LNA(15) were shown to reduce the number of scars and the scar area. Thus, it was shown that these antisense oligonucleotides were able to promote recovery from spinal cord injury by suppressing formation of scars.

Example 10

(Preparation of Spinal Cord Injury Model Mice and Administration of Antisense Oligonucleotides)

Mice of C57BL/6J strain (wild type) were purchased from CLEA Japan, Inc., bred, and subjected to experiments. 8 to 10 week-old male mice were subjected to the experiments in principle.

In deeply anesthetized mice, the dorsal part of the tenth vertebra (Th10) was removed surgically. Using a spinal cord injury model producing device (Infinite Horizon Impactor, Precision Systems and Instrumentation LLC, Lexington, N.Y.), mice were caused to have spinal cord injury by application of a 70 k-dyne stable impact force. For pseudo-operation mice as controls, only removal of the Th10 vertebra was performed, and the wound was sutured.

The antisense oligonucleotide (hT1-2126-LNA(15)) or chondroitinase ABC (ChABC) was administered to the mice caused to have spinal cord injury. The antisense oligonucleotide hT1-2126-LNA(15) has no mismatch with the 2067-2081-position region of mouse CSGalNAcT1 mRNA (SEQ ID NO: 166), and can target this region. The chondroitinase ABC was obtained from Seikagaku Corporation. Chondroitinase ABC treatment is known to promote recovery from spinal cord (Takeuchi, K., et al., Chondroitin sulphate N-acetylgal actosaminyltransferase-1 inhibits recovery from neural injury. Nature Communication, 2013, 4: 2740).

A silk sponge was placed on the vertebra dorsal part as an site of injury, and using an osmotic pump for small animals (Osmotic Mini-Pump (Model 2006 (volume of 200 μL for long-term use)), Alzet Company), the antisense oligonucleotide (100 nM) or chondroitinase ABC (20 μM) was continuously administered to the sponge. The administration was performed at a rate of 0.5 μl per hour for 2 weeks. Further, as negative controls, a group of spinal cord injury mice given a negative control nucleic acid (NEG#L1) were prepared.

T1KO mice (CSGalNAcT1 knockout mice) were previously prepared by homologous recombination using the embryotic stem cell strain RENKA derived from the C57BL/6N strain (Watanabe, T., et al., Chondroitin sulfate N-acetylgalactosaminyltransferase-1 is required for normal cartilage development. Biochem. J., 2010, 432: 47-55). It is known that in T1KO mice, recovery from spinal cord injury is promoted (Takeuchi, K., et al., 2013, described above). T1KO mice were caused to have spinal cord injury by the same method as described above, and the antisense oligonucleotide (hT1-2126-LNA(15)) or negative control nucleic acid was continuously administered to the site of injury.

Example 11

(Effects of Antisense Oligonucleotides on Hindlimb Motor Function in Spinal Cord Injury Model Mice)

Mice were caused to have spinal cord injury and treated with chemical agents in the manner described in Example 10, and the mice were then analyzed for the hindlimb motor function once a week up to six weeks.

The hindlimb motor function analysis was performed by BMS open field scoring (Basso, D. M., et al., Basso Mouse Scale for locomotion detects differences in recovery after injury of the spinal cord in five common mouse strains. J Neurotrauma, 2006, 23(5): 635-59.). At least two or three evaluators rated six mice for each group. The BMS provides an overall index of the motor ability, and determines the motor function recovery period and motor characteristics. The BMS is a test on a 9-point scale, where hindlimb paralysis corresponds to 0 point, and the normal motor corresponds to 9 points. The BMS score is such that the motion of each joint of the hindlimb, weight support, the step, cooperativity of forelimbs and hindlimbs, stability of the trunk, the position of the tail in walking, and so on are quantitatively graded. For each group, an average value and a standard error of the scores of six mice were calculated.

Figure 10:
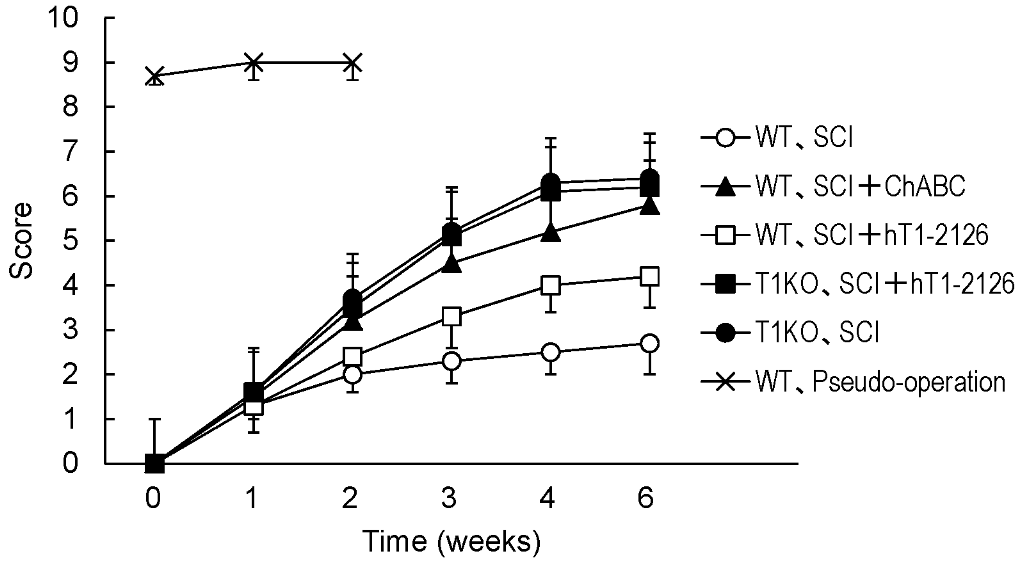
FIG. 10 is a graph showing the effects of antisense oligonucleotides on the hindlimb motor function in spinal cord injury model mice.

FIG. 10 shows the results of hindlimb motor function analysis for a group of wild-type mice caused to have spinal cord injury and given no pharmaceutical agent (WT, SCI), a group of wild-type mice caused to have spinal cord injury and given the chondroitinase ABC (WT, SCI+ChABC), a group of wild-type mice caused to have spinal cord injury and given the antisense oligonucleotide (hT1-2126-LNA (15)) (WT, SCI+hT1-2126), a group of T1KO mice caused to have spinal cord injury and given the antisense oligonucleotide (hT1-2126-LNA(15)) (T1KO, SCI+hT1-2126), a group of T1KO mice caused to have spinal cord injury and given no pharmaceutical agent (T1KO, SCI), and wild-type mice subjected to pseudo-operation. A higher score indicates a higher motor function.

It was shown that in the wild-type mice caused to have spinal cord injury and given the antisense oligonucleotide, recovery of the hindlimb motor function was promoted in comparison with the wild-type mice caused to have spinal cord injury and given no pharmaceutical agent.

It was confirmed that in the T1KO mice caused to have spinal cord injury and the wild-type mice caused to have spinal cord injury and given chondroitinase ABC, recovery of the hindlimb motor function was promoted in comparison with the wild-type mice caused to have spinal cord injury as described above (Takeuchi, K., et al., 2013, described above).

Further, it was shown that when the antisense oligonucleotide was administered to the T1KO mice caused to have spinal cord injury, the hindlimb motor function was recovered to the same degree as in the T1KO mice caused to have spinal cord injury and given no pharmaceutical agent. This showed that the antisense oligonucleotide did not have side effects such as off-target effect.

Example 12

(Effects of Antisense Oligonucleotides on the Amount of Sugar Chains in Spinal Cord Injury Model Mice)

The amount of sugar chains in spinal cord injury mice given the antisense oligonucleotide as described in Example 10 was determined to examine the effects of the antisense oligonucleotides on the amount of sugar chains in spinal cord injury model mice.

Three weeks after injury of the spinal cord, deeply anesthetized mice were rapidly killed by carbon dioxide gas without giving pains, and the spinal cord was excised to a length of 3 mm with the injury site at the center. Further, the cerebral cortex part was excised from wild-type mice and T1KO mice caused to have spinal cord injury and given no pharmaceutical agent.

The amount of sugar chains in the excised tissues (spinal cord and cerebral cortex part) was determined in the following manner. The tissues were put in a tube, and washed twice with 1 mL of phosphate buffer physiological saline (PBS). Subsequently, 0.5 mL of PBS was added to the tube, and the tissues were homogenized with BioMasher. 200 μL of a chondroitinase ABC reaction solution (10 mU chondroitinase ABC, 50 mM Tris-HCl pH 8.0, and 60 mM $CH_3COONa$) was added to the tube, and incubation was performed at 37° C. for 2 hours. The 100 μL of solution in the tube was dispensed to each of two tubes, and heated at 95° C. for 5 minutes. The solution in the tube was dried (for 3 hours or less) using a vacuum concentrator (Speed-Vac, Thermo Fisher Scientific). Subsequently, 25 μL of a solution of 0.35 M 2-aminobenzamide (fluorescent reagent for labeling sugar chains), 1.0 M $NaCNBH_4$ and 30% acetic acid in dimethyl sulfoxide (DMSO) was added to the tube. The tube was incubated at 65° C. for 2 hours to fluorescently label sugar chains. Subsequently, 150 μL of purified water was added to 50 μL of the reaction solution, and the resulting mixture was transferred into a glass centrifuge tube. 500 μL of chloroform (for fluorometric analysis) was added to the centrifuge tube, and the resulting mixture was stirred with a vortex mixer. The centrifuge tube was centrifuged at 1,500 rpm for 1 minute. The lower layer (chloroform) after the centrifugation was removed, so that the excess of the fluorescent reagent was removed. The removal of the fluorescent reagent with chloroform was repeated five times. Finally, the upper layer (aqueous layer) was put in a centrifugal ultrafiltration filter (Centricut Mini, 0.45 μm filter), and centrifuged at 7,000 rpm for 5 minutes to obtain a solution. The obtained solution was analyzed by anion exchange high performance liquid chromatography (HPLC). As columns, PA-G (4.6 mm×150 mm) and a guard column (4.0 mm×10 mm) (YMC Co., Ltd.) were used. The flow rate was 0.5 mL/min. As a solvent, 16 mM $NaH_2PO_4.2H_2O$ and 1 M $NaH_2PO_4.2H_2O$ were used at a concentration gradient such that 16 mM $NaH_2PO_4.2H_2O$ was used for 10 minutes, followed by increasing the concentration from 16 mM to 0.53 M over 60 minutes. Detection was performed with excitation light having a wavelength 330 nm and luminescence having a wavelength of 420 nm. In this way, the amount of sugar chains was determined for 2 to 4 mice of each group, an average value and a standard error were calculated.

Figure 11:
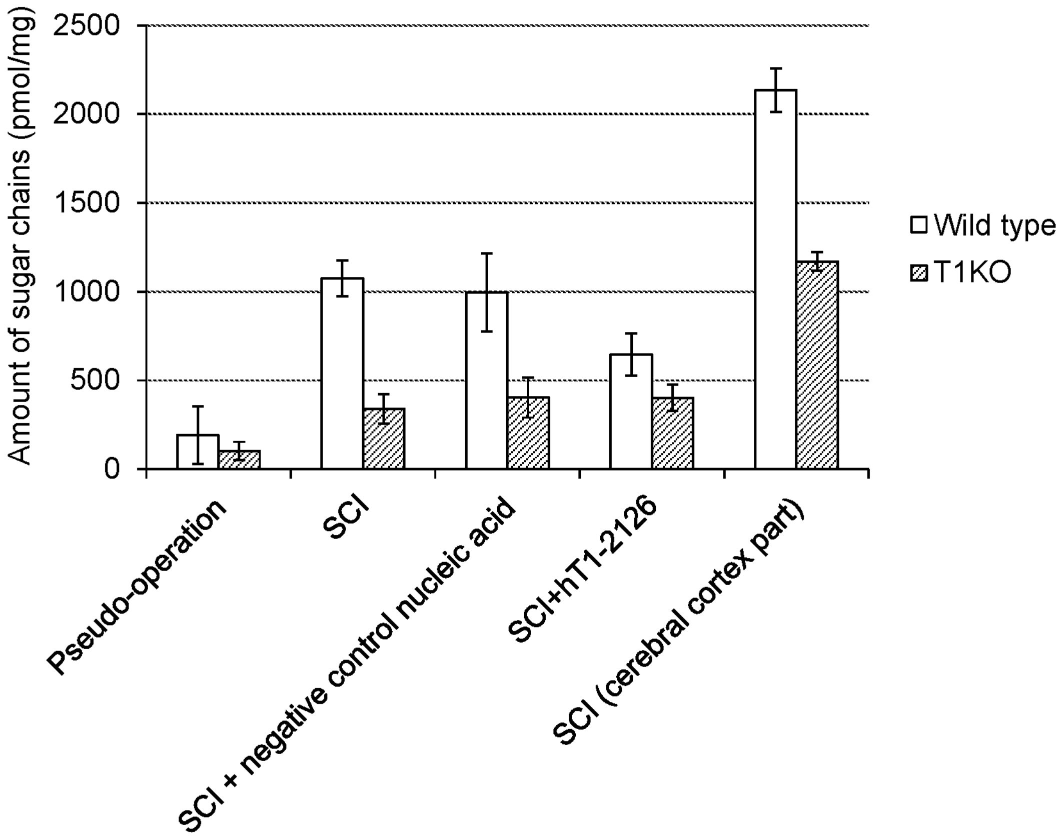
FIG. 11 is a graph showing the effects of antisense oligonucleotides on the amount of sugar chains in in spinal cord injury model mice.

FIG. 11 shows the amounts of sugar chains in the spinal cord in a group subjected to pseudo-operation, the spinal cord in a group caused to have spinal cord injury and given no pharmaceutical agent (SCI), the spinal cord in a group caused to have spinal cord injury and given a negative control nucleic acid (SCI+negative control nucleic acid), the spinal cord in a group caused to have spinal cord injury and given the antisense oligonucleotide (hT1-2126-LNA(15)) (SCI+hT1-2126) and the cerebral cortex part in a group caused to have spinal cord injury and given no pharmaceutical agent for the wild-type mice and the T1KO mice.

It is known that the amount of sugar chains in the cerebral cortex part is not significantly affected by spinal cord injury, and is larger than the amount of sugar chains in the spinal cord. Thus, the amount of sugar chains in the cerebral cortex part was determined as a positive control. It was confirmed that in the cerebral cortex part, it was possible to detect sugar chains for the wild-type mice and the T1KO mice.

It was shown that in the wild-type mice, when the mice were caused to have spinal cord injury, the amount of sugar chains in the spinal cord increased. On the other hand, it was shown that when the antisense oligonucleotide was administered to the wild-type mice caused to have spinal cord injury, the degree of increase in the amount of sugar chains was lower in comparison with the group which had not been treated with the pharmaceutical agent. This showed that when ministered in vivo, the antisense oligonucleotide of the present invention reduced the amount of chondroitin sulfate, and reduced the amount of sugar chains.

It was shown that in the T1KO mice, the amount of sugar chains in the spinal cord mildly increased when the mice caused to have spinal injury. However, it was shown that even when the antisense oligonucleotide was administered to the T1KO mice caused to have spinal cord injury, the degree of increase in the amount of sugar chains was comparable to that in the group which had not been treated with the pharmaceutical agent. This revealed that the antisense oligonucleotide did not have side effects such as off-target effect.

Example 13

(Effects of Intraspinally Administered Antisense Oligonucleotides on Hindlimb Motor Function in Spinal Cord Injury Model Rats)

The antisense oligonucleotide synthesized in Example 1 was intraspinally administered to spinal cord injury model rats, and recovery of the hindlimb motor function was examined.

Rats (Wistar; 12-week or older; CLEA Japan, Inc.) were subjected to experiments. The rats were caused to have spinal cord injury in the same manner as described in Example 10 except that a 200 k-Dyne impact force was applied. Pseudo-operation rats were prepared in the same manner as described in Example 10.

After injury of the spinal cord, on the same day, the antisense oligonucleotide (hT1-2514-LNA(15) or hT2-1617-AmNA(15)) synthesized in Example 1, or the control nucleic acid NEC#L1 (see Example 2) was intraspinally administered to the rats. The administration was performed by intraspinally injecting a nucleic acid solution (containing Pontamine dye) with a concentration of 100 μg/μl (total volume: 10 μl) to the rats at a rate of 1 μl per 30 seconds to 1 minute. Introduction of the pharmaceutical agent was confirmed with the Pontamine dye.

The hindlimb motor functions of the rats were evaluated on the basis of the BBB score (Basso, D. M., et al., A sensitive and reliable locomotor rating scale for open field testing in rats. J Neurotrauma, 1995, 12(1): 1-21, and Basso, D. M., et al., Graded histological and locomotor outcomes after spinal cord contusion using the NYU weight-drop device versus transection. Experimental Neurology, 1996, 139(2): 244-256). The BBB score is such that the amount of motion of the hindlimb of an animal, cooperativity of forelimbs and hindlimbs, the state of the tail, and so on are visually observed, and quantitatively graded on a 21-point scale. Two or three observers independently performed evaluation based on the BBB score once a week after injury of the spinal cord and administration of the pharmaceutical agent. An average value and a standard error of scores for 9 rats were calculated for each group. Statistical calibration was performed by the ANOVA and post-hoc test (*P<0.01, with respect to control).

Figure 12:
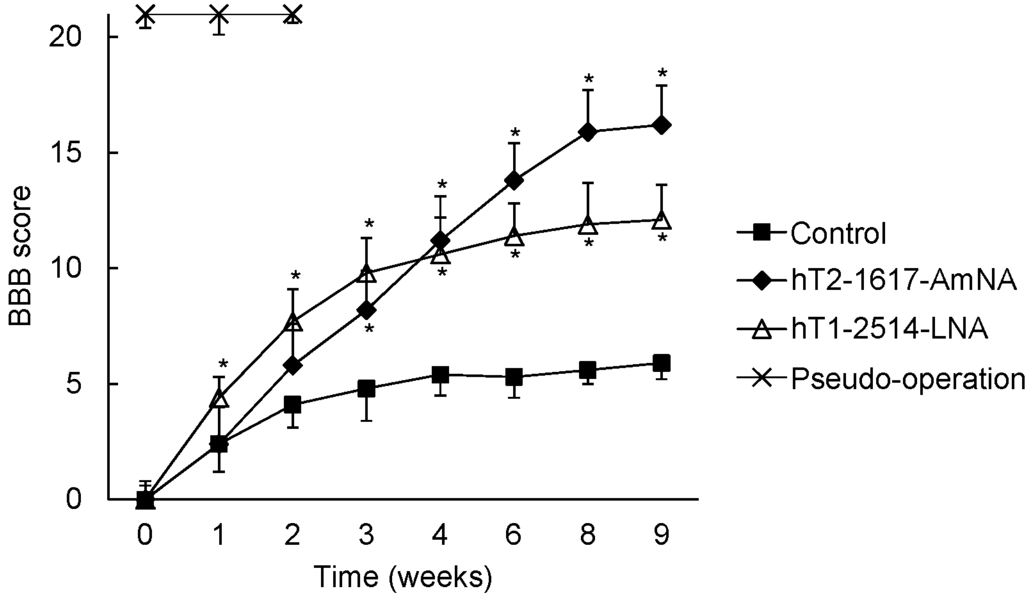
FIG. 12 is a graph showing the effects of antisense oligonucleotides on the hindlimb motor function in spinal cord injury model rats.

FIG. 12 shows the results of hindlimb motor function analysis for a group given the control nucleic acid, a group given the antisense oligonucleotide hT1-2514-LNA(15), a group given the antisense oligonucleotide hT2-1617-AmNA (15), and pseudo-operation rats. A higher BBB score indicates a higher motor function.

It was shown that by administration of the antisense oligonucleotide (hT1-2514-LNA(15) or hT2-1617-AmNA (15)), recovery of the hindlimb motor function in the rats caused to have spinal cord injury was more significantly promoted in comparison with the control nucleic acid.

Example 14

(Effects of Antisense Oligonucleotide Locally Administered to Injury Site on Hindlimb Motor Function in Spinal Cord Injury Model Mice)

The antisense oligonucleotide synthesized in Example 1 was locally administered to spinal cord injury model mice at the injury site, and recovery of the hindlimb motor function was examined.

Mice (C57BL/6j; 16-week or older) were subjected to experiments. The mice were caused to have spinal cord injury in the same manner as described in Example 10 except that a 100 k-Dyne impact was applied. Pseudo-operation mice were prepared in the same manner as described in Example 10.

After injury of the spinal cord, on the same day, the antisense oligonucleotide (hT1-2514-LNA(15) or hT2-1617-AmNA(15)) synthesized in Example 1, or the control nucleic acid NEC#L1 (see Example 2) was locally administered (administered with gelatin sponge) to the mice. The administration was performed in the following manner: a nucleic acid solution with a concentration of 500 μg/μl was mixed with atelocollagen (AteloGene®, KOKEN Co., Ltd.) (total volume: 20 μl), the mixed solution was adsorbed to a fibroin sponge, and the sponge was retained at the spinal cord injury region.

The hindlimb motor functions of the mice were evaluated on the basis of the BMS score as described in Example 11. An average value and a standard error of scores for 12 mice were calculated for each group. Statistical calibration was performed by the ANOVA and post-hoc test (*P<0.01, with respect to control).

Figure 13:
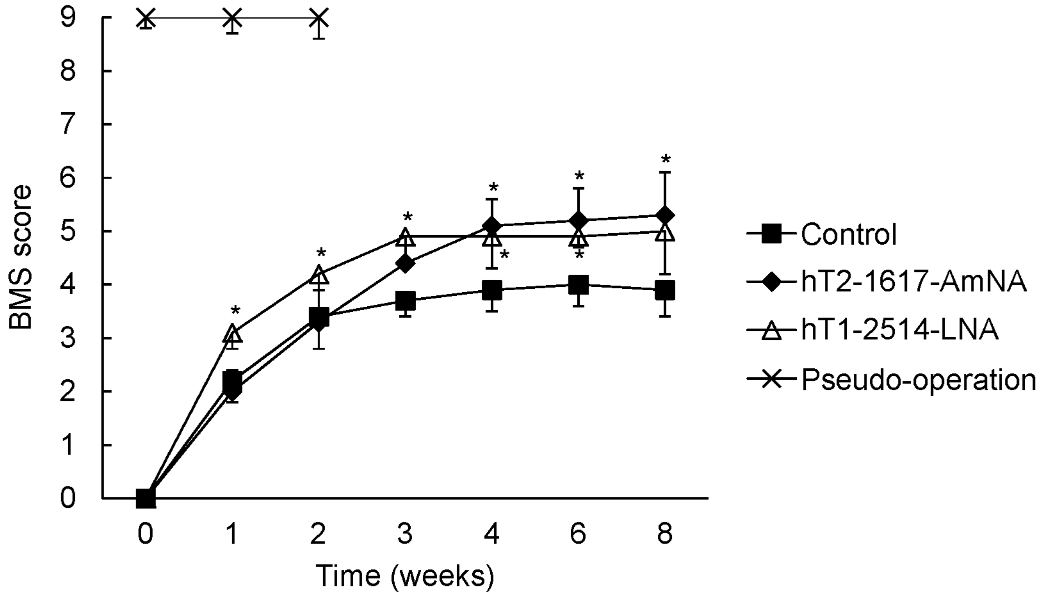
FIG. 13 is a graph showing the effects of antisense oligonucleotides on the hindlimb motor function in spinal cord injury model mice.

FIG. 13 shows the results of hindlimb motor function analysis for a group given the control nucleic acid, a group given the antisense oligonucleotide hT1-2514-LNA(15), a group given the antisense oligonucleotide hT2-1617-AmNA (15), and pseudo-operation mice. A higher BMS score indicates a higher motor function.

It was shown that by administration of the antisense oligonucleotide (hT1-2514-LNA(15) or hT2-1617-AmNA (15)), recovery of the hindlimb motor function in the mice caused to have spinal cord injury was more significantly promoted in comparison with the control nucleic acid.

All the publications, patents and patent applications cited herein are incorporated herein by reference in their entirety.

The invention claimed is:

1. An antisense oligonucleotide comprising at least one modified nucleotide, wherein the antisense oligonucleotide suppresses expression of one or both of the chondroitin sulfate N-acetylgalactosaminyltransferase-1 (CSGalNAcT1) gene and the chondroitin sulfate N-acetylgalactosaminyltransferase-2 (CSGalNAcT2) gene, wherein the antisense oligonucleotide consists of the nucleotide sequence set forth in SEQ ID NO: 113.

2. The antisense oligonucleotide according to claim 1, wherein the antisense oligonucleotide suppresses expression of one or both of the CSGalNAcT1 gene and the CSGalNAcT2 gene by 20% or more.

3. The antisense oligonucleotide according to claim 1, wherein the modified nucleotide comprises a bicyclic sugar.

4. The antisense oligonucleotide according to claim 1, wherein at least one internucleoside bond is a phosphorothioate bond.

5. The antisense oligonucleotide according to claim 1, wherein the modified nucleotide comprises 5-methylcytosine.

6. The antisense oligonucleotide according to claim 1, wherein the antisense oligonucleotide is a gapmer.

7. A pharmaceutical composition for treating a disease or a condition related to an increase in chondroitin sulfate, the pharmaceutical composition comprising the antisense oligonucleotide according to claim 1.

8. The pharmaceutical composition according to claim 7, wherein the disease or the condition is spinal cord injury.

9. A method for treating a disease or a condition related to an increase in chondroitin sulfate, comprising administering to a subject an antisense oligonucleotide comprising at least one modified nucleotide, wherein the antisense oligonucleotide consists of a nucleotide sequence of SEQ ID NO: 113.

10. The method according to claim 9, wherein the antisense oligonucleotide consists of a nucleotide sequence selected from the group consisting of SEQ ID NOs: 49-107, SEQ ID NOs: 131-137, SEQ ID NOs: 139-145, SEQ ID NOs: 148-151, SEQ ID NO: 153, and SEQ ID NO: 154.

11. The method according to claim 9, wherein the antisense oligonucleotide suppresses expression of one or both of the CSGalNAcT1 gene and the CSGalNAcT2 gene by 20% or more.

12. The method according to claim 9, wherein the modified nucleotide comprises a bicyclic sugar.

13. The method according to claim 9, wherein at least one internucleoside bond is a phosphorothioate bond.

14. The method according to claim 9, wherein the modified nucleotide comprises 5-methylcytosine.

15. The method according to claim 9, wherein the antisense oligonucleotide is a gapmer.

* * * * *

SEQUENCE LISTING

```
<160> NUMBER OF SEQ ID NOS: 186

<210> SEQ ID NO 1
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 1
```

tctgtggcca gcttg 15

<210> SEQ ID NO 2
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 2
ctgcatactc tgtgg 15

<210> SEQ ID NO 3
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 3
tagagtaaag ctatc 15

<210> SEQ ID NO 4
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 4
tggcgggtaa ggcca 15

<210> SEQ ID NO 5
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 5
tcctcggggt ggcgg 15

<210> SEQ ID NO 6
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 6
caccaactca tcccg 15

<210> SEQ ID NO 7
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 7
tccaccaact catcc 15

<210> SEQ ID NO 8
<211> LENGTH: 15
<212> TYPE: DNA

<213> ORGANISM: Artificial
<220> FEATURE:
<223> OTHER INFORMATION: Synthetic Oligonucleotide

<400> SEQUENCE: 8
ttccaccaac tcatc 15

<210> SEQ ID NO 9
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 9
cttccaccaa ctcat 15

<210> SEQ ID NO 10
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 10
caatggcttc cacca 15

<210> SEQ ID NO 11
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 11
aaggctgatt caatg 15

<210> SEQ ID NO 12
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 12
caaggctgat tcaat 15

<210> SEQ ID NO 13
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 13
ggccgaatgg tcgaa 15

<210> SEQ ID NO 14
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 14
tttcatgatg gggcc 15

<210> SEQ ID NO 15
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 15
ctttcatgat ggggc 15

<210> SEQ ID NO 16
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 16
actttcatga tgggg 15

<210> SEQ ID NO 17
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 17
cactttcatg atggg 15

<210> SEQ ID NO 18
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 18
tcactttcat gatgg 15

<210> SEQ ID NO 19
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 19
ttttcacttt catga 15

<210> SEQ ID NO 20
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 20
ctttttgcta gaggc 15

<210> SEQ ID NO 21
<211> LENGTH: 15
<212> TYPE: DNA
<213> ORGANISM: Artificial
<220> FEATURE:

-continued

<223> OTHER INFORMATION: Synthetic Oligonucleotide

<400> SEQUENCE: 21
tttcccaaag taaac 15

<210> SEQ ID NO 22
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 22
catcacagaa aaaga 15

<210> SEQ ID NO 23
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 23
gtgaagtaga tgtcc 15

<210> SEQ ID NO 24
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 24
ttgaggaatt cagat 15

<210> SEQ ID NO 25
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 25
tattgaggaa ttcag 15

<210> SEQ ID NO 26
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 26
aaaagaactg gataa 15

<210> SEQ ID NO 27
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 27
caggattgta ctgac 15

<210> SEQ ID NO 28
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 28
ccaggattgt actga 15

<210> SEQ ID NO 29
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 29
ccagctgctg ttcca 15

<210> SEQ ID NO 30
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 30
accagctgct gttcc 15

<210> SEQ ID NO 31
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 31
caaatccaaa gtctc 15

<210> SEQ ID NO 32
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 32
ccaaatccaa agtct 15

<210> SEQ ID NO 33
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 33
tcccaaatcc aaagt 15

<210> SEQ ID NO 34
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 34
atcccaaatc caaag 15

<210> SEQ ID NO 35
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 35
gtcatcccaa atcca 15

<210> SEQ ID NO 36
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 36
acacgtcatc ccaaa 15

<210> SEQ ID NO 37
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 37
gacacgtcat cccaa 15

<210> SEQ ID NO 38
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 38
atactgacac gtcat 15

<210> SEQ ID NO 39
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 39
gatactgaca cgtca 15

<210> SEQ ID NO 40
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 40
cgatactgac acgtc 15

<210> SEQ ID NO 41
<211> LENGTH: 15

<212> TYPE: DNA
<213> ORGANISM: Artificial
<220> FEATURE:
<223> OTHER INFORMATION: Synthetic Oligonucleotide

<400> SEQUENCE: 41
accgatactg acacg 15

<210> SEQ ID NO 42
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 42
tgaccgatac tgaca 15

<210> SEQ ID NO 43
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 43
ctgaccgata ctgac 15

<210> SEQ ID NO 44
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 44
tctgaccgat actga 15

<210> SEQ ID NO 45
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 45
agcctttgat gtcca 15

<210> SEQ ID NO 46
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 46
gtaccactat gaggt 15

<210> SEQ ID NO 47
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 47
gtccgtacca ctatg 15

<210> SEQ ID NO 48
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 48
ttcatggcct tggac 15

<210> SEQ ID NO 49
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 49
atgccagagg tggaa 15

<210> SEQ ID NO 50
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 50
catgccagag gtgga 15

<210> SEQ ID NO 51
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 51
tcatgccaga ggtgg 15

<210> SEQ ID NO 52
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 52
ctcgggggtc agctc 15

<210> SEQ ID NO 53
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 53
gctcgggggt cagct 15

<210> SEQ ID NO 54
<211> LENGTH: 15
<212> TYPE: DNA
<213> ORGANISM: Artificial

<220> FEATURE:
<223> OTHER INFORMATION: Synthetic Oligonucleotide

<400> SEQUENCE: 54
tgctcggggg tcagc 15

<210> SEQ ID NO 55
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 55
ctgctcgggg gtcag 15

<210> SEQ ID NO 56
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 56
actgctcggg ggtca 15

<210> SEQ ID NO 57
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 57
tactgctcgg gggtc 15

<210> SEQ ID NO 58
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 58
gtactgctcg ggggt 15

<210> SEQ ID NO 59
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 59
tcactgggta gtttg 15

<210> SEQ ID NO 60
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 60
ccccatactc actgg 15

<210> SEQ ID NO 61
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 61
taaggtaaaa ctttc 15

<210> SEQ ID NO 62
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 62
tggcgagtga gaccc 15

<210> SEQ ID NO 63
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 63
tcttcaggat ggcga 15

<210> SEQ ID NO 64
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 64
caccaattca tctcg 15

<210> SEQ ID NO 65
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 65
tccaccaatt catct 15

<210> SEQ ID NO 66
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 66
ttccaccaat tcatc 15

<210> SEQ ID NO 67
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 67
cttccaccaa ttcat 15

<210> SEQ ID NO 68
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 68
caataacttc cacca 15

<210> SEQ ID NO 69
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 69
aagcccgctt caata 15

<210> SEQ ID NO 70
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 70
caagcccgct tcaat 15

<210> SEQ ID NO 71
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 71
gtccaaaagg gcgga 15

<210> SEQ ID NO 72
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 72
tttcatgaga ggtcc 15

<210> SEQ ID NO 73
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 73
ctttcatgag aggtc 15

<210> SEQ ID NO 74

<211> LENGTH: 15
<212> TYPE: DNA
<213> ORGANISM: Artificial
<220> FEATURE:
<223> OTHER INFORMATION: Synthetic Oligonucleotide

<400> SEQUENCE: 74
actttcatga gaggt 15

<210> SEQ ID NO 75
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 75
cactttcatg agagg 15

<210> SEQ ID NO 76
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 76
tcactttcat gagag 15

<210> SEQ ID NO 77
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 77
tcttcacttt catga 15

<210> SEQ ID NO 78
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 78
ctttcagcaa gtggc 15

<210> SEQ ID NO 79
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 79
tttaccaaaa tacac 15

<210> SEQ ID NO 80
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 80
catcacagaa aaaca 15

<210> SEQ ID NO 81
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 81
acatcacaga aaaac 15

<210> SEQ ID NO 82
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 82
gagaaataga tatca 15

<210> SEQ ID NO 83
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 83
ttaaggaatt cggct 15

<210> SEQ ID NO 84
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 84
tgttaaggaa ttcgg 15

<210> SEQ ID NO 85
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 85
aacaccacag ggtaa 15

<210> SEQ ID NO 86
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 86
caggattgta aagac 15

<210> SEQ ID NO 87
<211> LENGTH: 15
<212> TYPE: DNA

<213> ORGANISM: Artificial
<220> FEATURE:
<223> OTHER INFORMATION: Synthetic Oligonucleotide

<400> SEQUENCE: 87
gcaggattgt aaaga 15

<210> SEQ ID NO 88
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 88
ccagctgctg ctcca 15

<210> SEQ ID NO 89
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 89
accagctgct gctcc 15

<210> SEQ ID NO 90
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 90
caaagccaaa atctc 15

<210> SEQ ID NO 91
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 91
ccaaagccaa aatct 15

<210> SEQ ID NO 92
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 92
ttccaaagcc aaaat 15

<210> SEQ ID NO 93
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 93
attccaaagc caaaa 15

<210> SEQ ID NO 94
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 94
gtcattccaa agcca 15

<210> SEQ ID NO 95
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 95
acaagtcatt ccaaa 15

<210> SEQ ID NO 96
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 96
gacaagtcat tccaa 15

<210> SEQ ID NO 97
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 97
atactgacaa gtcat 15

<210> SEQ ID NO 98
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 98
gatactgaca agtca 15

<210> SEQ ID NO 99
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 99
cgatactgac aagtc 15

<210> SEQ ID NO 100
<211> LENGTH: 15
<212> TYPE: DNA
<213> ORGANISM: Artificial
<220> FEATURE:

<223> OTHER INFORMATION: Synthetic Oligonucleotide

<400> SEQUENCE: 100
aacgatactg acaag 15

<210> SEQ ID NO 101
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 101
tgaacgatac tgaca 15

<210> SEQ ID NO 102
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 102
ctgaacgata ctgac 15

<210> SEQ ID NO 103
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 103
tctgaacgat actga 15

<210> SEQ ID NO 104
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 104
aacctttcac ttcca 15

<210> SEQ ID NO 105
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 105
gaatcacaat gaggt 15

<210> SEQ ID NO 106
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 106
gtccgaatca caatg 15

<210> SEQ ID NO 107
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 107
ttcatggctt tagac 15

<210> SEQ ID NO 108
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 108
tgttggccat gttga 15

<210> SEQ ID NO 109
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 109
ataacattga taagc 15

<210> SEQ ID NO 110
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 110
atttatttct tcttt 15

<210> SEQ ID NO 111
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 111
ttcatttatt tcttc 15

<210> SEQ ID NO 112
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 112
tttcactttc atgat 15

<210> SEQ ID NO 113
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 113
acatcacaga aaaag 15

<210> SEQ ID NO 114
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 114
ccccagcctt tgatg 15

<210> SEQ ID NO 115
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 115
gccagaggtg gaaga 15

<210> SEQ ID NO 116
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 116
ggtttattta aacag 15

<210> SEQ ID NO 117
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 117
tggtttattt aaaca 15

<210> SEQ ID NO 118
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 118
tttggtttat ttaaa 15

<210> SEQ ID NO 119
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 119
ctttggttta tttaa 15

<210> SEQ ID NO 120
<211> LENGTH: 15

<212> TYPE: DNA
<213> ORGANISM: Artificial
<220> FEATURE:
<223> OTHER INFORMATION: Synthetic Oligonucleotide

<400> SEQUENCE: 120
atactttggt ttatt 15

<210> SEQ ID NO 121
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 121
gagattgttt ggttc 15

<210> SEQ ID NO 122
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 122
aaagagattg tttgg 15

<210> SEQ ID NO 123
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 123
tgaaaagaga ttgtt 15

<210> SEQ ID NO 124
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 124
ttttgaaaag agatt 15

<210> SEQ ID NO 125
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 125
tttcataaac tacca 15

<210> SEQ ID NO 126
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 126
aaatttcata aacta 15

<210> SEQ ID NO 127
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 127
attaaatttc ataaa 15

<210> SEQ ID NO 128
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 128
ttaattaaat ttcat 15

<210> SEQ ID NO 129
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 129
tgttttaatt aaatt 15

<210> SEQ ID NO 130
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 130
ctgtgtttta attaa 15

<210> SEQ ID NO 131
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 131
tgttaccatg atatc 15

<210> SEQ ID NO 132
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 132
tattgttacc atgat 15

<210> SEQ ID NO 133
<211> LENGTH: 15
<212> TYPE: DNA
<213> ORGANISM: Artificial

<220> FEATURE:
<223> OTHER INFORMATION: Synthetic Oligonucleotide

<400> SEQUENCE: 133
agtcatgact acttg 15

<210> SEQ ID NO 134
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 134
caaggcccaa cagca 15

<210> SEQ ID NO 135
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 135
tttaccataa ttttc 15

<210> SEQ ID NO 136
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 136
tcatttcttg taatt 15

<210> SEQ ID NO 137
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 137
tcttctcact cattt 15

<210> SEQ ID NO 138
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 138
gaagaaactc taaaa 15

<210> SEQ ID NO 139
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 139
aactttcaaa gggaa 15

<210> SEQ ID NO 140
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 140
cttttcttca ggatg 15

<210> SEQ ID NO 141
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 141
gtttgtcttt tctaa 15

<210> SEQ ID NO 142
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 142
attattaatg acctc 15

<210> SEQ ID NO 143
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 143
atcaggatta ttaat 15

<210> SEQ ID NO 144
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 144
attaaatatc agttt 15

<210> SEQ ID NO 145
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 145
agagggtcac atgtc 15

<210> SEQ ID NO 146
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 146
atattaataa ttgat 15

<210> SEQ ID NO 147
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 147
caatgatatt aataa 15

<210> SEQ ID NO 148
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 148
tcttgatgaa tacaa 15

<210> SEQ ID NO 149
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 149
accaaggtgt aattg 15

<210> SEQ ID NO 150
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 150
acagaaaaac atcaa 15

<210> SEQ ID NO 151
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 151
ttgtaaagac tgaac 15

<210> SEQ ID NO 152
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 152
taaagatgaa catct 15

<210> SEQ ID NO 153

<211> LENGTH: 15
<212> TYPE: DNA
<213> ORGANISM: Artificial
<220> FEATURE:
<223> OTHER INFORMATION: Synthetic Oligonucleotide

<400> SEQUENCE: 153
gaggtggaaa agacc 15

<210> SEQ ID NO 154
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 154
cctcattcat ggctt 15

<210> SEQ ID NO 155
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 155
ccagctgctg ctcca 15

<210> SEQ ID NO 156
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 156
tactgctcgg gggtc 15

<210> SEQ ID NO 157
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 157
tgttggccat gttga 15

<210> SEQ ID NO 158
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 158
ctcgggggtc agctc 15

<210> SEQ ID NO 159
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 159
tcatgccaca ggtgg 15

<210> SEQ ID NO 160
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 160
ctcaggggtc agttc 15

<210> SEQ ID NO 161
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 161
tactgctcag gggtc 15

<210> SEQ ID NO 162
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 162
ccagctgctg tccta 15

<210> SEQ ID NO 163
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 163
ccagctgctg ctcca 15

<210> SEQ ID NO 164
<211> LENGTH: 4299
<212> TYPE: DNA
<213> ORGANISM: Homo sapiens

<400> SEQUENCE: 164
gttctccctg gggagcggga ggctccaggc gcggctgggg cgctgtgggc agatgcgctc 60
ggtcctcacc agcggcgttg tgcggcgaac cctgcggtgc ttcgggaagg cggtcgttcc 120
tccctgctcc caccgttttc cagcgtgtgc gctcttacct tctctgggga aaaaaggaaa 180
ttttttattt tttaacattt catttcatga aaccgttttt tttaagtggt ggcgctgaac 240
acagtccttg cagagggggg cagcactttc cctcctgacc ccaacctgga aaccccagtg 300
tgacttcagc gctgtcagag cattggaagc agagctgcga gttaggaagc ggctcgctgg 360
cagctgggca cgtttctttc ctgcgagatc ggcttttttg atttgctctt tttcacatga 420
aaatgttcag cttcattttt agacaccttt agacatggtt atcactgttt aaagccttga 480
ttttttttta aacaaatagt ttgcatttta ttcattgaaa cagggagaga acaaatacca 540
tcctgctttt tgggctgcct tcctatttca aggaaagacg ccaaggtaat tttgacccag 600

-continued

```
aggagcaatg atgtagccac ctcctaacct tcccttcttg aacccccaga cataaaggga    660
gcagtaggca taaaatgtgg ggagctgacc atctgccggt ccggtcctga ccttccacta    720
gtagtgagac caatccagct cttgctgctg ctgtggcttt gtgaggaggt cccctcttgc    780
tgttggctgc acatcaggaa ggctgtgatg ggaatgaagg tgaaaacttg gagatttcac    840
ttcagtcatt gcttctgcct gcaagatcat cctttaaaag tagagaagct gctctgtgtg    900
gtggttaact ccaagaggca gaactcgttc tagaaggaaa tggatgcaag cagctccggg    960
ggccccaaac gcatgcttcc tgtggtctag cccagggaag cccttccgtg gggggccccgg  1020
ctttgaggga tgccaccggt tctggacgca tggctgattc ctgaatgatg atggttcgcc   1080
gggggctgct tgcgtggatt tcccgggtgg tggttttgct ggtgctcctc tgctgtgcta   1140
tctctgtcct gtacatgttg gcctgcaccc caaaaggtga cgaggagcag ctggcactgc   1200
ccagggccaa cagccccacg gggaaggagg ggtaccaggc cgtccttcag gagtgggagg   1260
agcagcaccg caactacgtg agcagcctga agcggcagat cgcacagctc aaggaggagc   1320
tgcaggagag gagtgagcag ctcaggaatg ggcagtacca agccagcgat gctgctggcc   1380
tgggtctgga caggagcccc ccagagaaaa cccaggccga cctcctggcc ttcctgcact   1440
cgcaggtgga caaggcagag gtgaatgctg gcgtcaagct ggccacagag tatgcagcag   1500
tgcctttcga tagctttact ctacagaagg tgtaccagct ggagactggc cttacccgcc   1560
accccgagga gaagcctgtg aggaaggaca agcgggatga gttggtggaa gccattgaat   1620
cagccttgga gaccctgaac agtcctgcag agaacagccc caatcaccgt ccttacacgg   1680
cctctgattt catagaaggg atctaccgaa cagaaaggga caaagggaca ttgtatgagc   1740
tcaccttcaa aggggaccac aaacacgaat tcaaacggct catcttattt cgaccattcg   1800
gccccatcat gaaagtgaaa aatgaaaagc tcaacatggc caacacgctt atcaatgtta   1860
tcgtgcctct agcaaaaagg gtggacaagt tccggcagtt catgcagaat ttcagggaga   1920
tgtgcattga gcaggatggg agagtccatc tcactgttgt ttactttggg aaagaagaaa   1980
taaatgaagt caaaggaata cttgaaaaca cttccaaagc tgccaacttc aggaacttta   2040
ccttcatcca gctgaatgga gaattttctc ggggaaaggg acttgatgtt ggagcccgct   2100
tctggaaggg aagcaacgtc cttctctttt tctgtgatgt ggacatctac ttcacatctg   2160
aattcctcaa tacgtgtagg ctgaatacac agccagggaa gaaggtattt tatccagttc   2220
ttttcagtca gtacaatcct ggcataatat acggccacca tgatgcagtc cctcccttgg   2280
aacagcagct ggtcataaag aaggaaactg gattttggag agactttgga tttgggatga   2340
cgtgtcagta tcggtcagac ttcatcaata taggtgggtt tgatctggac atcaaaggct   2400
ggggcggaga ggatgtgcac ctttatcgca agtatctcca cagcaacctc atagtggtac   2460
ggacgcctgt gcgaggactc ttccacctct ggcatgagaa gcgctgcatg gacgagctga   2520
cccccgagca gtacaagatg tgcatgcagt ccaaggccat gaacgaggca tcccacggcc   2580
agctgggcat gctggtgttc aggcacgaga tagaggctca ccttcgcaaa cagaaacaga   2640
agacaagtag caaaaaaaca tgaactccca gagaaggatt gtgggagaca ctttttcttt   2700
ccttttgcaa ttactgaaag tggctgcaac agagaaaaga cttccataaa ggacgacaaa   2760
agaattggac tgatgggtca gagatgagaa agcctccgat ttctctctgt tgggcttttt   2820
acaacagaaa tcaaaatctc cgctttgcct gcaaaagtaa cccagttgca ccctgtgaag   2880
tgtctgacaa aggcagaatg cttgtgagat tataagccta atggtgtgga ggttttgatg   2940
gtgtttacaa cacactgaga cctgttgttt tgtgtgctca ttgaaatatt catgatttaa   3000
```

```
gagcagtttt gtaaaaaatt cattagcatg aaaggcaagc atatttctcc tcatatgaat   3060
gagcctatca gcagggctct agtttctagg aatgctaaaa tatcagaagg caggagagga   3120
gataggctta ttatgatact agtgagtaca ttaagtaaaa taaaatggac cagaaaagaa   3180
aagaaaccat aaatatcgtg tcatattttc cccaagatta accaaaaata atctgcttat   3240
ctttttggtt gtccttttaa ctgtctccgt ttttttcttt tatttaaaaa tgcacttttt   3300
ttcccttgtg agttatagtc tgcttattta attaccactt tgcaagcctt acaagagagc   3360
acaagttggc ctacattttt atattttta agaagatact ttgagatgca ttatgagaac   3420
tttcagttca aagcatcaaa ttgatgccat atccaaggac atgccaaatg ctgattctgt   3480
caggcactga atgtcaggca ttgagacata gggaaggaat ggtttgtact aatacagacg   3540
tacagatact ttctctgaag agtattttcg aagaggagca actgaacact ggaggaaaag   3600
aaaatgacac tttctgcttt acagaaaagg aaactcattc agactggtga tatcgtgatg   3660
tacctaaaag tcagaaacca cattttctcc tcagaagtag ggaccgcttt cttacctgtt   3720
taaataaacc aaagtatacc gtgtgaacca aacaatctct tttcaaaaca gggtgctcct   3780
cctggcttct ggcttccata agaagaaatg gagaaaaaaa tatatatata tatattgtga   3840
aagatcaatc catctgccag aatctagtgg gatggaagtt tttgctacat gttatccacc   3900
ccaggccagg tggaagtaac tgaattattt tttaaattaa gcagttctac tcgatcacca   3960
agatgcttct gaaaattgca ttttattacc atttcaaact attttttaaa aataaataca   4020
gttaacatag agtggtttct tcattcatgt gaaaattatt agccagcacc agatgcatga   4080
gctaattatc tctttgagtc cttgcttctg tttgctcaca gtaaactcat tgtttaaaag   4140
cttcaagaac attcaagctg ttggtgtgtt aaaaaatgca ttgtattgat ttgtactggt   4200
agtttatgaa atttaattaa aacacaggcc atgaatggaa ggtggtattg cacagctaat   4260
aaaatatgat ttgtggatat gaaaaaaaaa aaaaaaaaa                          4299
```

<210> SEQ ID NO 165
<211> LENGTH: 3782
<212> TYPE: DNA
<213> ORGANISM: Homo sapiens

<400> SEQUENCE: 165

```
ctctcaggcg cggcggcgcg cccgggggtg ggtggctgag gcggcggcgg gcccaaggcg     60
tgaggcgccg cccgggtgtc cccgcggcgc aggaggcggt ggagcgcaga gcgggcgagc    120
gcgaaaaatc actaccaata taatggattt tatatatcag attgctttat tctggatatc    180
atggtaacaa tacagaaagt atacataatt tcccatttct gcaagtagtc atgactgctg    240
aagaaagaaa aacttaaagc tacggcagaa ttattttatg gaaattctga ttttgttttt    300
aatttttgat aactttttac taaaggtatg aacacacaaa gagcttattt tgttaggcaa    360
atacacatta ataagaatgc ctagaagagg actgattctt cacacccgga cccactggtt    420
gctgttgggc cttgctttgc tctgcagttt ggtattattt atgtacctcc tggaatgtgc    480
cccccagact gatggaaatg catctcttcc tggtgttgtt ggggaaaatt atggtaaaga    540
gtattatcaa gccctcctac aggaacaaga agaacattat cagaccaggg caaccagtct    600
gaaacgccaa attgcccaac taaaacaaga attacaagaa atgagtgaga agatgcggtc    660
actgcaagaa agaaggaatg taggggctaa tggcataggc tatcagagca acaaagagca    720
agcacctagt gatcttttag agtttcttca ttcccaaatt gacaaagctg aagttagcat    780
```

-continued

```
aggggccaaa ctacccagtg agtatggggt cattcccttt gaaagtttta ccttaatgaa    840
agtatttcaa ttggaaatgg gtctcactcg ccatcctgaa gaaaagccag ttagaaaaga    900
caaacgagat gaattggtgg aagttattga agcgggcttg gaggtcatta ataatcctga    960
tgaagatgat gaacaagaag atgaggaggg tccccttgga gagaaactga tatttaatga   1020
aaatgacttc gtagaaggtt attatcgcac tgagagagat aagggcacac agtatgaact   1080
ctttttaag aaagcagacc ttacggaata tagacatgtg accctcttcc gcccttttgg    1140
acctctcatg aaagtgaaga gtgagatgat tgacatcact agatcaatta ttaatatcat   1200
tgtgccactt gctgaaagaa ctgaagcatt tgtacaattt atgcagaact tcagggatgt   1260
ttgtattcat caagacaaga agattcatct cacagtggtg tattttggta aagaaggact   1320
gtctaaagtc aagtctatcc tagaatctgt caccagtgag tctaattttc acaattacac   1380
cttggtctca ttgaatgaag aatttaatcg tggacgagga ctaaatgtgg gtgcccgagc   1440
ttgggacaag ggagaggtct tgatgttttt ctgtgatgtt gatatctatt tctcagccga   1500
attccttaac agctgccggt taaatgctga gccaggtaag aaggtgtttt accctgtggt   1560
gttcagtctt tacaatcctg ccattgttta tgccaaccag gaagtgccac cacctgtgga   1620
gcagcagctg gttcacaaaa aggattctgg cttttggcga gattttggct ttggaatgac   1680
ttgtcagtat cgttcagatt tcctgaccat tggtggattt gacatggaag tgaaaggttg   1740
ggtggagaa gatgttcatc tttatcgaaa atacttacat ggtgacctca ttgtgattcg    1800
gactccggtt cctggtcttt tccacctctg gcatgaaaag cgctgtgctg atgagctgac   1860
cccgagcag taccgcatgt gcatccagtc taaagccatg aatgaggcct ctcactccca    1920
cctgggaatg ctggtcttca gggaggaaat agagacgcat cttcataaac aggcatacag   1980
gacaaacagt gaagctgttg gttgaaatca taattaatgc gttactgtat gaaccacaaa   2040
acagcactat ttatttagcc ttacttctac ttccagatgc agtgcctctt ttggagaaga   2100
catgtttatt tttcatgttc tttctgacat tactttagca attcaacttg atgtgagaag   2160
aaaaaacaaa tgtttcaaca caaaatctct gttttgtgag aatactgcac tatggaataa   2220
ttgacaaatt gaaatctcat atttgtccca aaagttgttt tgagttagtt ctacctggtg   2280
cccatgttct gattgtgtgt gggattgcat ggtgtcctga ttgcatctag gtggagcgga   2340
tggaatgtgc tgggccactg ttgggtggag agcagcacat tcttacagag gagatggagc   2400
gttatgagca tagtatgtgg ataggtatct tcacctgccc gcccctgagt cagcctcctt   2460
gacttgatag cttgaagaat ccttttccac tgaaatagag gataattaat tgacacatct   2520
gaaatcccca atcaatcaat caagagaaag gtagaactaa aaactcctta acttactgtt   2580
gcttacaccc ctgaaagtct gtttttaagc aaatgggtaa tagtagaaaa taggttagaa   2640
tctatggctt gattaaaaat atgttattac attatcatgt tcaggattag gattagtagt   2700
cagttgctgt aaactatttt gaacaaacag aaaagaacac ggaaacattt ttaacagagc   2760
atttaattat gttggaatac aggatcctag ctctgtctgg gaacattagt ttatttgagc   2820
cagctctatc agggtcttcc catggtggtt cagaatagat gagcatagca tggttttgtt   2880
tgtttttgct ttcaattttc taatttggca tggatccata tgtatttact atcctttttc   2940
taatatatta atatatgcta catttgtatt tgcattacta taatactttg agttgaaaaa   3000
gagtttcatt gtggagagaa aaagcaaatg gtatgccaca agatcactct gatttgagaa   3060
aagggaggag gggaagatag tctgaatgga aatctgaaat acggaatgtt ttagagaaat   3120
atgtcacttg catatagaat gttttaattg aggtataaat taatgagaca aagtgaaaaa   3180
```

gaaattatat tcagatagga ctgcactaca ttatttgtca cacatggatc tgttaccatc 3240
aggtcaattc ctagtatgca taaatttttt aaccctttta aaagagacct atgttgaaaa 3300
cccctgaaaa ttcactgaag aaaaatcatt actctttttc tcagtaaatc atatcatctg 3360
aaatattaca aatttcaaat ttctaggtgc tatattaatt caatattaca ataactctta 3420
cctaattatt cttacaagtt ttaagttgtg gtagtttagt gatttttttta aaagatgtgt 3480 gaaatgttct ctgcaaaata attcaggcca ctgtctcctt ttatatatta ttataattat 3540
ttattatgaa gaccagtgaa ttacgatatt taaagtgaga gaacttaatt atttgcaaag 3600
gtaagttaca gcttgttttt tgagagaatc aaatgagttt acttttgttc ctgttgtttt 3660
taactagctt taagtttaaa gatggaagct aagcaatgga aatgctatac gtttttgaca 3720
tttattaaat ggtaccaata aagtatttta ttaccaaaag ttaaatgaaa aaaaaaaaaa 3780
aa 3782

<210> SEQ ID NO 166
<211> LENGTH: 4247
<212> TYPE: DNA
<213> ORGANISM: Mus musculus

<400> SEQUENCE: 166
ggctgttgga actggaggtg gagccgagcc cagggccgcc tcgcaggagg gaaagttcag 60
cggcagcagg ggagcagcgt agccgaggga tccggctccg ctgtctgcag tgttgcctgg 120
ggagctattg catcatacct ggagggacca gtgcagcagc tatggaccag agaaggaagt 180
aggcggaaaa ggaggacacc atagcctgcc tgtgtagacc tgggagggtg aggagctgag 240
gccgaagctc cttctgtctt ggtcttcttg gaaggtcggt ctacacattc aactctcttc 300
ttgctgcatt tcgtgacacc acagccttgg ggactttcaa ttgcctccca gtggctagag 360
aacatttgca gctttcaaaa ccgctccttg cttatcgagc agaacacccg gtggcaacag 420
agaaggttcc ttgaacatgc atgacagatt ggagagttgc catgtggatc tacagtcctc 480
agtgtgagaa gctttaaaca atcatttctg tggctggaat cttcaaatga tctacttttt 540
attgcctctg gagcataacc agtggtggcg ctgagctgaa cacggtgcta gcagaagggg 600
gcggtacttt ccctctggac cctgacttgg aagccaagtg caactccagc gcagtcacca 660
ccagaagcag atgtgcgagc ggaacagctg tgcgcctttc tttctgccga ggttccctct 720
catcttcagc atatcagaaa ggctatgatg ggaacgaatg aaggaacttg gaggctccac 780
ttgactgact gtttctgtct agaaaatctt cccttggaag caagagagcc gtctcatgta 840
atggctgact tctaaagaca ggccatgttc tagaaggaaa taggtgaaat tggttctggg 900
aacttcagtg gcactgtggt ctaaccagaa aagcccgtgt tgggggccct tctggtgccc 960
tgggatgttg catactctgg acctggatgc atggcctgca cctgagtgag aatggtccgc 1020
cgcgggctgc tggggtggat ttctcgggta gtgattctgc tggtgctgct ctgttgtgcc 1080
atctctgtcc tctacatgtt agcctgcact ccaaaaggcg accaggagca gttgggactg 1140
ccacgggcca atggacccac aggcaaagat ggctaccaag cggtgctgca ggagcgcgag 1200
gaacagcatc gtaactatgt gaatagcctt aaacgacaga tagctcagct aaaggatgaa 1260
ctgcaggcac gcagtgagca gttccgcagt gggcaggacc aggccagcga tgccaccagc 1320
ctgcgctcag gctgggaccg tgagcccaaa gcccaggccg atctgctggc cttcctgcgt 1380
ggacaggtgg acaaggccga ggtacatgcc ggtgtcaagc tggccacgga gtatgctgct 1440

-continued

```
gtgccttttg atagcttcac tctgcagaaa gtataccagc tggagactgg cctgacccgc   1500
caccctgagg agaagccagt gaggaaagac aagcgcgatg agctggtaga agccatcgaa   1560
tcggccctgg agagtctaaa cagccctgtg gagagcagcc cacaccagcg tccttacaca   1620
gctgcagact tcatagaagg gatttaccga accgaaaggg ataaaggcac tttgtatgag   1680
ctgaccttca aaggggacca caagcatgaa ttccagcgac ttgtcctatt tcgacctttt   1740
ggccccatca tgaaagtgaa aaaggaaaaa ctcaacctgg ccaacacgct tatcaatgtt   1800
attgtgcccc tagcgaggag ggtggacaag ttccggcact tcatgcagaa cttcagggag   1860
atgtgcatcc aacaggatgg gagagttcat ctcaccgttg tttattttgg gaaagaagaa   1920
atgaatgaag tcaaaggaat acttgaaaac acttcaaaag ctgccaattt cagaaacttc   1980
accttcatcc aactgaatgg agaattctcc cggggaaagg gactggatgt tggagcccgc   2040
ttctggaagg gaagtaacgt cctgctcttt ttctgtgatg tagacatcta cttcacctcg   2100
gagttcctca acacttgtag gctgaacaca cagccaggga agaaggtatt ttatccggtt   2160
ctgttcagtc agtataaccc cggcgtaatc tacggccatc acgatgcagt ccctccgcta   2220
ggacagcagc tggtcataaa gaaggaaaca ggattttgga gggactttgg atttgggatg   2280
acatgtcagt accggtcaga cttcatcaac ataggtggat ttgacctgga catcaaaggc   2340
tggggtggtg aagatgtgca cctgtaccgg aaatatctcc atagcaacct catagtggtc   2400
cgcacacctg tacggggact tttccacctg tggcatgaaa agcactgtat ggatgaactg   2460
acccctgagc agtacaagat gtgcatgcaa tcaaaggcta tgaatgaagc atcccatggg   2520
cagctgggga tgcttgtctt ccggcatgaa atagaggctc atcttcgcaa acagaagcag   2580
aaagccagca gtaaaaagac atgatctcct aggcacagat tagcatagac atttaatttt   2640
ttttgccttt ggcagttgct gaagaagtag atgcaacaaa gagcaacaaa gtatctgact   2700
ggtgagggag agatgaaaga agagtctcat cccgggattc tgttggctcc gtgtatggtg   2760
acgctgactg tgttttcagc aaatgatctc tctggttcct gctcactgaa atattcacaa   2820
cctcagacca gttttgtaga acgtttacta gaatgagatg caaacacatt gaattggtta   2880
catcagaggg ctttggtact accaggacta ccaaagtctc agaccaagca gaggatctat   2940
gtgagaaatg gagatctctg acattagcgt cctccaggag atagtgagca aaatcaaagg   3000
gccctggaaa cacaccatgg aaactgtaat ttccccagta ttaaccaaaa aaacaaaaaa   3060
acaaaaccac caccaccaac aacaaaaaac cctctctttc ccattattgt ttagtcatct   3120
ttattctaaa aatgcacttt tgtttttgct tctgagtgtt atgcttattt aattacccat   3180
ttgcaagcct tagtaggaac atattgtagt atatacaatt ctatgatttt ttaaaaaaga   3240
ttttatttta gtttttgttg tttttgttga tttgtctact tgagacagtc ttgtcacaga   3300
gcccgagata aacttgaaat tatgatcctc ctgcctctga agcctgagtg ctgagattaa   3360
aggtgggtgc caccacagct ggcaagaaga tacatgcaga ggagtgggag gaaatcctct   3420
agttgcaagc tcctggagat ctgatctaag gactggccaa tctcagacca cgctaaggct   3480
atgtgtgggg ttggggagag aaaggtatca agaaactatc taagactgtc caaagaggaa   3540
caatcaaaca ctggagaaag aaaaagacac tttcctcttc acaaaaagga cactaagaag   3600
cccttggtat atttactaga gaacataatt tctcctctgg agaagtgggg accactttct   3660
tacctgtttg aataaaccaa agttatgaac caaacaatca cttttcaaaa cagggtgctc   3720
ttcttggtct ctggtttgca taagaagaaa acgcaggaaa tatatatcta aatatatatt   3780
ttgaaagacc aatccgttaa tctagtgaga cggaagattt tgctacattt ccattcactc   3840
```

```
ctggctatgt gggagcaact tatttttaaa ataagcaatg ttactgattg ctgggacgtt   3900

tctgaagcat tttcttataa ctccaaattc ttttttttta aataataaaa tctgattaac   3960

attgagtggt ttctacatcc atatgcaaac tatttattta ttagccagca ccggatgcat   4020

gagctgatca tctctcctgt ctctgtgcct tctgtctgcc cacagtgaac tcattgttga   4080

aatgcttcaa gaacactcaa gctgtgtgtt ataaaaaaaa aaaaaggaaa aagagcattg   4140

tattgatttg tactggtagt ttataaaatt taattaaaac acaagacatg aatggaaggt   4200

ggcattgcac agctaataaa atctgtgaat ttgatttctt tccgtaa                 4247
```

<210> SEQ ID NO 167
<211> LENGTH: 3676
<212> TYPE: DNA
<213> ORGANISM: Mus musculus

<400> SEQUENCE: 167

```
tttcctcgcg cgcgccggaa gtggcggtgc tccgcggcgg cgcgccgggc cggccccgcg     60

cagggcgctg gccaggtgtg caggtcccca gaggcggcga cgctgagcgg cgggcgcgaa    120

aagtcaccac ccagataatg gattttatag atcagattgc ttagtgtgga tatcatggta    180

acaatacagg aagtattgtt aatttctcac ttctaccaag tagtcatgac tactgaagaa    240

agaatctttt aaaactacaa cagagtgcac ttgggtacct cttatggaaa ttctaatttt    300

gtttttaact tttggtaatt ttttactaaa gtcatgaaca agcagagggc ttgtcctgtc    360

aggcaaacac actctagtga gaatgtctag aagaggatcg attctgcaca gccggaccca    420

gtggctgctg ttgggccttg ctttgctctt cagtttagta ttatttatgt acctcctgga    480

atgtgccccc cagactgatg gaaatgcttc tcttcctggt gttgttagag aaaattatgg    540

taaagaatat taccaggccc tcctgcagga gcaagaagaa cattaccaaa ccagggcaac    600

cagtctgaaa cgccagattg cccagctaaa gcaagaatta caagatatga gtgagaagat    660

gagagccttg caagagagaa agaagctagg ggctaacggc gtaggctatc ctggcaacag    720

agagcaggca cccagtgacc tcttagagtt tcttcactcc cagatcgata gagctgaagt    780

tagcgtgggg gccaaactcc ccagtgagta tggagtcgtt ccctttgaaa gttttacttt    840

aatgaaagta tttcagttgg aaatgggtct cactcgccat cctgaagaaa agccagttag    900

aaaagacaaa cgagacgaac tggtagaagt tattgaagct ggcgtggagg tcattaataa    960

tcctgatgaa gatgatgcac aggaagatga ggagggtccc cttggagaga aactgatatt   1020

taatgaaaat gacttcatag aaggctatta tcgcactgag agagataaag gcacgcagta   1080

tgaactgttt tttaagaaag cagaccttat ggagtacaga catgtgaccc tcttccgccc   1140

ttttggacct ctcatgaaag tgaagaatga actgatcgac attacaagat cagttattaa   1200

tatcattgtg ccacttgcgg agaggacaga ggcgttttca cagtttatgc agaacttcag   1260

agatgtttgt attcatcaag acaagaggat tcatctcacc gttgtgtatt ttgggaaaga   1320

aggactatct aaagtcaagt ctattctaga atctgtctca agtgagtctg attttcacaa   1380

ttacaccttg gtctcgttgg acgaagaatt taatcgtgga cgaggactaa atgtgggtgc   1440

ccgagcttgg gacaagggag aggtcttgat gtttttctgt gatgttgata tatatttctc   1500

agctgaattc cttaacagct gccggttaaa tgctgagcca ggtaaaaagg tgttttaccc   1560

tgtggtgttc agtctttaca accctgccat tgtctatgcc aaccaggacg tgccgccccc   1620

tgtggagcag cagctggttc ataaaaagga ctctggtttt tggagagact ttggctttgg   1680
```

-continued

```
gatgacctgt caatatcaat cggatttcct gagtgtcggt ggattcgaca tggaagtaaa   1740

aggctggggt ggagaagatg ttcatcttta ccgaaaatac ctacacggtg atcttattgt   1800

gattcggact ccagttcccg gtcttttcca cctctggcat gagaaacatt gtgcagatga   1860

gctgacccct gagcagtacc gaatgtgcat ccaatccaaa gccatgaatg aggcctccca   1920

ctctcacctg ggaatgatgg ttttcaggga ggagatagag atgcatcttc gcaaacaggc   1980

atacagaaca aacagcgaga ctgctgggta acagtcaacg tgggagagtc ggaagcacaa   2040

accagcactg ttaattcagc cttaattcca actctagatt atgtgcctct tccagagaaa   2100

aacttttctt ttccatgttc tttctgaaat gtttttgtag ctcaacttga tgtaagaaga   2160

aaacgcaggt gtcttgatgt atagcctgcc ttgtgagagt actatagtat gaaacagttg   2220

acaaaatgaa attttatatt tgtccccaaa atcgtttgaa ttagattctg cctggtacct   2280

gtgttctgat tggtcctgga gtatacgagg ctaatgttga gttggtcagc acactcctac   2340

agggaacaga acactggttg gtcgaaatgt tcaggcagat atgcctgctg accactaagt   2400

caatcatttg acttcagtct ttagatgaaa gctttcattg atcacatgta gaatattttt   2460

tttcacagaa aataattaac atatctaaaa tctacagtcc atcacaaagg cataagtcaa   2520

aacccttag tttcatgttg ctttcccttt gaatatgttt ttaagcaaat ggatatagta   2580

gatatagttt agaatttatg gtttgattat aaataaaata tattgttatg ttaccaatgt   2640

tcaaaattca tagtcaaatt gtagtagatt gttttgaaca ttttattata ttggaatgca   2700

ggacagtagc tgtgtttggg aacgtctttt tatataagcc agaggcatag aagatatgaa   2760

cgttatagca tggttttgta tggcttttgt tttgcactgt cttgtttagc atgggcacat   2820

atatatttat tttctatatg ctaattttgc cataattgtg tttgcatttg tattatactt   2880

tcagttgaaa gagttttatt gaaaaaaaat taaatgcatt atataataag accacccttg   2940

atttgagaaa agggaaggaa ggaaaagtga cctgataaaa atataaatta tggagtactt   3000

taaaaaaatg tacagattga atgctacttt aattgaaatg taaattatat taatgagaca   3060

agatgaataa gaaattatat tccagtagaa ctgtactata atatttatca cacatggata   3120

ttttatcatt gggtcattta ctagatccag aaattggaga taaaataaag gcatgcatag   3180

ttttttaac ccctgacttt taaagggacc tgctatttct atataaccca tgagaactca   3240

gaaaaagtca ttatttttgt tcagtaaatc ataccatctc aaaagttaca aatgccaaat   3300

ttctaggtgc taatgtgaat ccgattcaat aataactagt tgctgagggt tctacccggc   3360

atatcgttga ggtatttttt aagatgtata aagtgctttc tgcagaataa gcagagccag   3420

tatctccttt gtacacactt atttattgta aagaccagtg accatggtat ttaaaattag   3480

ggtacttaat gattttcaaa ggtgatttca gcttggtttt gagataatca aatgattttt   3540

actttaactc ctattttttt aaactagctt ttatttgaag atggaagcta agcaatgaaa   3600

gcattactat attttttaca ttaagtggta ccaataaagt attttgttac caaaagctaa   3660

aaaaaaaaaa aaaaaa                                                   3676
```

<210> SEQ ID NO 168
<211> LENGTH: 2314
<212> TYPE: DNA
<213> ORGANISM: Rattus norvegicus

<400> SEQUENCE: 168

```
atggtccgac gcgggctggt ggggtggatt tcccgggtag tgattctgct ggtgctgctc     60

tgttgtgcca tctctgttct ctacatgtta gcctgcaccc caaaaggcga ccaagagcag    120
```

-continued

```
ctgggactgc cacgggccaa cggccccaca ggcaaagatg gctaccaagc ggtgctacag    180
gagcgtgagg aacagcatcg caactatgtg aatagtctta agcgacagat cgcgcagctc    240
aaggatgaac tgcaggcacg cagtgagcag ctccgcagtg ggcaggacca ggccagcgat    300
gccaccagcc tgcggtcagg ctgggaccct gaacccaaag cccaggctga tatactggcc    360
ttcctgcgtg ggcaggtgga caaggctgag gtccacgccg gtgtcaagct ggccaccgaa    420
tatgctgctg tgccttttga tagcttcact ctgcagaaag tataccagct ggagactggt    480
ctgacccgcc accctgagga gaaaccagtg aggaaggaca agcgagatga gctagtggaa    540
gctatcgaat cagccctgga gagtctaaac agccctgtgg aaagcagccc acaccagcgc    600
ccttacacgg ctgcagactt catagaaggg atctaccgaa cagaaaggga taaaggcact    660
ttgtatgagc tgaccttcaa aggggaccat aagcatgaat tccaacgact tgtcctattt    720
cgaccttttg gccccatcat gaaagtgaag aaggaaaagc tcaacatggc caacacactt    780
atcaacgtta tcgtgcccct agcgaggagg gtggacaagt tccggcactt catgcagaac    840
ttcagggaga tgtgcatcca acaagatggg agagttcatc ttaccgttgt ttattttggg    900
aaagaagaaa tgaatgaagt caaaggaata cttgaaaaca cttccaaggc tgccaatttt    960
agaaacttca ccttcatcca gctgaatgga gagttctccc ggggaaaggg actggatgtt   1020
ggagcccgct tctggaaggg aagtaatgtc gtgctctttt tctgtgatgt ggacatctac   1080
ttcacctctg agttcctcaa cacatgtagg ctgaacacac agccagggaa gaaggtattt   1140
tatccggttc ttttcagtca gtataaccct ggcataatct acggccatca tgatgctgtc   1200
cctgccctag aacagcagct ggtcataaag aaggaaacag gattttggag ggactttgga   1260
ttcggaatga cttgtcagta ccggtcagac ttcatcaaca taggtggatt tgacctggac   1320
atcaaaggct ggggcggtga agatgtgcac ctgtaccgga aatatctcca tagcaacctc   1380
atagtgatac gcacgcctgt acggggactt ttccaccttt ggcatgagaa gcactgtatg   1440
gatgaactga cccctgagca gtacaggatg tgcatgcaat caaaggctat gaatgaagca   1500
tcccacgggc agctgggaat gcttgtcttc cggcatgaaa tagaggctca ccttcgcaaa   1560
cagaagctca aagccagcag taaaaagaca tgacctccta ggtaaagatt agccaagacg   1620
tttaaatttt gtgcctttgg cagttactga agaagtagat gcaacaaggt atagacttcc   1680
acaaagggca acagagaatc tgactgatga gtgacagatg aatgaagagt ctcgggtttc   1740
tgttggctct gtgtatgctg gtgactctga ctgtgtttac agccaaatga gctctctggt   1800
ccctgctccc tgaaatagtc acaaccggtt tcagaaaacc agaaggagct gcaagcccac   1860
tgacttctct tctttggatt ggttacatca gagggctttg gtactactag gactaccaaa   1920
ggctcagatg gagctctcgg acggagcaga ggacctgtgt gaaaagtgga gctctgacat   1980
tagtgtcctc caccagaccg tgagcaaaat caaagggacc tggaaacaaa ccatccaaac   2040
tgtcatttcc ctagtattaa ctgaaaaaca aacaaacaaa caaacaaaaa ccctaaaaaa   2100
caaaaaaaag acaaaaacaa aaacaaaaaa caaagccaac aacaactaca acaaaaaccc   2160
ctctctttcc cattattgtt tagtcatctc tgttctaaaa atgcactttt tttgcttctg   2220
agcattatgc ttatttaatt acccatttcc aagccttagt aggagtacat tgtagtacac   2280
acatttttat gatttttta aagatttgtt ttta                                 2314
```

<210> SEQ ID NO 169
<211> LENGTH: 3636
<212> TYPE: DNA

<213> ORGANISM: Rattus norvegicus

<400> SEQUENCE: 169

```
catttcctcg cgcgcgccgg aagtggcggt gctccgcggc ggcgcgcggg gccagccagc     60
gcagggcgct ggccaggtgt acagctcccc agaggcggca gcgctgagcg gcgagcgcga    120
acagtcacca cccagataat ggattatata gaccagattg cgtagtgtgg atatcatggt    180
aacaatacag gaagtataaa tttctcactt ctgcaagtag tcatgactac tgaagaagga    240
atcttttaaa atgacagcag agctcatttg ggtacctctc atggaaatcc taattttgtt    300
tttaactttt ggtaactttt cgctgaagtc atgaacaagc aaagagcttg ccttgttagg    360
caaacacaca ctagtgagaa tgtctagaag aggaccgatt cttcacagcc ggacccagtg    420
gctgctggtg ggccttgctt tgcttttcag tctagtatta tttatgtacc tcctggaatg    480
tgccccccag actgatggaa atgcttctct ccctggtgtg gttagagaaa attatggtaa    540
agaatattac caagccctcc tgcaggagca agaagaacat taccaaacca gggcaaccag    600
tttgaaacgc cagattgccc agctaaagca agaactacaa gatatgagtg agaagatgag    660
agccttgcaa gagaggaaga agctaggggc taacggcata ggctatcagg gcaacagaga    720
gcagacaccc agcgacctct tagagtttct tcattcccag atcgacagag ctgaagtcag    780
catagggggcc aaactaccca gtgagtatgg agtcgttccc tttgaaagtt ttactttaat    840
gaaagtattt cagttggaaa tgggtctcac gcgccatcct gaagaaaagc cagttagaaa    900
agacaaacga gatgaattgg tagaagttat tgaagctggc ttggaggtca ttaataatcc    960
tgatgaagat gatgaacagg aagatgagga gggcccccttt ggagagaaac tgatatttaa   1020
tgaaaatgac ttcatagaag gctattaccg cactgagaga gataaaggca cgcactatga   1080
gctgtttttt aagaaggcag accttatgga atacaggcat gtgaccctct tccgcccttt   1140
cggacctctc atgaaagtga agagcgagct gattgacatt acaagatcgg ttattaatat   1200
cattgtgccg cttgctgaga ggacagaagc cttttcacag tttatgcaga acttcagaga   1260
tgtttgtatt catcaagaca agagaattca tctcaccgtt gtgtattttg ggaaagaagg   1320
actatctaca gtcaagtcta ttctagaatc tgtctcaagt gagtctaatt ttcacaatta   1380
caccttggtc tcattgaacg aagaatttaa tcgtggacga ggactaaatg tgggtgcccg   1440
aacttgggac aagggagagg tcttgatgtt tttctgtgat gttgatatat atttctcagc   1500
tgaattcctt aacagctgcc ggttaaatgc tgagccaggt aaaaaagtgt tttaccccgt   1560
ggtgttcagt ctttacaacc ctgccatcgt ctatgccaac caggaagtgc cacctcccgt   1620
ggagcagcag ctggttcata aaaaggactc tggtttttgg agagattttg gctttgggat   1680
gacgtgtcaa tatcaatcag attttctgag tgtcggtgga ttcgacatgg aagtaaaagg   1740
ctggggtgga gaagatgttc atctttaccg aaagtactta catggtgatc ttattgtgat   1800
tcggactcca gttcctggcc ttttccacct ctggcatgag aaacactgtg cggacgagct   1860
gacccctgag caataccgaa tgtgcatcca atccaaagcc atgaacgagg cctctcactc   1920
ccacctggga atgatggtct tcagggagga aatagagatg cacctccgca aacaggcgta   1980
cagaaccaac agcgaggccg ctgggtgaca ggcagcgcat gggagtctga gccacaagcc   2040
agcactgttt attcagcctt aactccaact ctagattctg tgcctcttcc agagaaggct   2100
ttgcccatgt tctttctgaa ataatctgta gctcaacttg atgtaagaag aaaatgcagg   2160
cgtcttgatg gaaagcctgc gctgtgaagg tactgtggta tgcaccagtt gacaaagtga   2220
aattgatatt tgtccccaaa tcgtttgaat tagactctgc ctggtacctg tattctgatt   2280
```

ggtcgtggat gtgcgcaagg ctgatgttgg gttggctagc accctcctcc agggtacaga 2340
gtattggctg gtcatggtgt tcaggtggct atcacctgct gaccactaag ccagtcactc 2400
gacttgagtc tttaaatgaa gcttttattg atcatatgta gaaaattttt cacagagaat 2460
aattaacata tctgaaacct gcagtccttc atgaaggcat aaatctaaac cccttagttt 2520
tatgttgctt tacctctaaa tatattttta agcaaatgga tatagtacat ttaatttaga 2580
atttatggtt tgattataaa taaaatatat tgttatgtta ccaatgttca gaatgcatag 2640
tcaaactgtc atagattgtt ttgagcattt tattatattg gaatgcagga aagtagctgt 2700
gtttggaaca tcattttata taagccagat gtatcagaac cttcctgaag agacacagaa 2760
gatatgaaca ttatagcatg gttttgtatg cttttgtttg cactgtcttg tttagcatag 2820
ctacatatat atttattttc tagtatgtta atttttgcca caaatttgct agcatttgta 2880
ttatacttcc agttgaaaga gttttattga aaaaaaaacc aatttaatgt gttatataat 2940
aagatcaccc ttgatttaag aaaagtaatc tgataaaaat atgaattatg gagtacttta 3000
aaaaacatgt acagattaat gctattttaa ttgaaatgta aattatttta atgagacaag 3060
atgaataaga aattatgttc cggtagaact gtactataat atttatcaca catggatatt 3120
ttatcatccg gccatcactt gatcaggaac tggcactatg gcgagggcgg gcttgctttc 3180
atagcccttg actcttacag ggctatttgt atatagccca tgcgaactcg gaaagtcact 3240
gtttggttca gtaaatcagc cacctcagac gtgacaaatg ccaaatctct aggtgctaag 3300
gtgagtccac tccaatggta gctaactgct gagggctccg ggagtgcgag gtgttttaag 3360
atgtataaag tgctctctgc agaataagca gagccaatgt ctcctttgta cacacttatt 3420
tattgtaaag agcagtgacc atggtattta aagttagggt acttagtgat ttataaaggt 3480
ggtttcagct tggttttgag ataatcaaat gatttttact ttaactccta ttttttttaaa 3540 actagctttt atttgaagat gggagctaag atttgaaagc attactatat tttttacatt 3600
aagtggtacc aataaagtat tttgttacca aaagcc 3636

<210> SEQ ID NO 170
<211> LENGTH: 20
<212> TYPE: DNA
<213> ORGANISM: Artificial
<220> FEATURE:
<223> OTHER INFORMATION: Primer

<400> SEQUENCE: 170
gagtcaacgg atttggtcgt 20

<210> SEQ ID NO 171
<211> LENGTH: 20
<212> TYPE: DNA
<213> ORGANISM: Artificial
<220> FEATURE:
<223> OTHER INFORMATION: Primer

<400> SEQUENCE: 171
gacaagcttc ccgttctcag 20

<210> SEQ ID NO 172
<211> LENGTH: 20
<212> TYPE: DNA
<213> ORGANISM: Artificial
<220> FEATURE:
<223> OTHER INFORMATION: Primer

<400> SEQUENCE: 172
tcagggagat gtgcattgag 20

<210> SEQ ID NO 173
<211> LENGTH: 20
<212> TYPE: DNA
<213> ORGANISM: Artificial
<220> FEATURE:
<223> OTHER INFORMATION: Primer

<400> SEQUENCE: 173
agttggcagc tttggaagtg 20

<210> SEQ ID NO 174
<211> LENGTH: 20
<212> TYPE: DNA
<213> ORGANISM: Artificial
<220> FEATURE:
<223> OTHER INFORMATION: Primer

<400> SEQUENCE: 174
ggagaccctg aacagtcctg 20

<210> SEQ ID NO 175
<211> LENGTH: 20
<212> TYPE: DNA
<213> ORGANISM: Artificial
<220> FEATURE:
<223> OTHER INFORMATION: Primer

<400> SEQUENCE: 175
gccgtttgaa ttcgtgtttg 20

<210> SEQ ID NO 176
<211> LENGTH: 20
<212> TYPE: DNA
<213> ORGANISM: Artificial
<220> FEATURE:
<223> OTHER INFORMATION: Primer

<400> SEQUENCE: 176
gccattgttt atgccaacca 20

<210> SEQ ID NO 177
<211> LENGTH: 20
<212> TYPE: DNA
<213> ORGANISM: Artificial
<220> FEATURE:
<223> OTHER INFORMATION: Primer

<400> SEQUENCE: 177
atccaccaat ggtcaggaaa 20

<210> SEQ ID NO 178
<211> LENGTH: 23
<212> TYPE: DNA
<213> ORGANISM: Artificial
<220> FEATURE:
<223> OTHER INFORMATION: Primer

<400> SEQUENCE: 178
tcctagaatc tgtcaccagt gag 23

<210> SEQ ID NO 179
<211> LENGTH: 22

<212> TYPE: DNA
<213> ORGANISM: Artificial
<220> FEATURE:
<223> OTHER INFORMATION: Primer

<400> SEQUENCE: 179
acatcaagac ctctcccttg tc 22

<210> SEQ ID NO 180
<211> LENGTH: 19
<212> TYPE: DNA
<213> ORGANISM: Artificial
<220> FEATURE:
<223> OTHER INFORMATION: Primer

<400> SEQUENCE: 180
tgcaccacca actgcttag 19

<210> SEQ ID NO 181
<211> LENGTH: 18
<212> TYPE: DNA
<213> ORGANISM: Artificial
<220> FEATURE:
<223> OTHER INFORMATION: Primer

<400> SEQUENCE: 181
gatgcaggga tgatgttc 18

<210> SEQ ID NO 182
<211> LENGTH: 25
<212> TYPE: DNA
<213> ORGANISM: Artificial
<220> FEATURE:
<223> OTHER INFORMATION: Primer

<400> SEQUENCE: 182
ccaatttcag aaacttcacc ttcat 25

<210> SEQ ID NO 183
<211> LENGTH: 22
<212> TYPE: DNA
<213> ORGANISM: Artificial
<220> FEATURE:
<223> OTHER INFORMATION: Primer

<400> SEQUENCE: 183
tgttcagcct acaagtgttg ag 22

<210> SEQ ID NO 184
<211> LENGTH: 23
<212> TYPE: DNA
<213> ORGANISM: Artificial
<220> FEATURE:
<223> OTHER INFORMATION: Primer

<400> SEQUENCE: 184
ttaatatcat tgtgccactt gcg 23

<210> SEQ ID NO 185
<211> LENGTH: 29
<212> TYPE: DNA
<213> ORGANISM: Artificial
<220> FEATURE:
<223> OTHER INFORMATION: Primer

<400> SEQUENCE: 185

-continued

```
tagaatagac ttgactttag atagtcctt                                  29


<210> SEQ ID NO 186
<211> LENGTH: 15
<212> TYPE: DNA
<213> ORGANISM: Artificial
<220> FEATURE:
<223> OTHER INFORMATION: Synthetic Oligonucleotide

<400> SEQUENCE: 186

gaaaactaaa atgag                                                 15
```